(12) United States Patent
Coull et al.

(10) Patent No.: US 7,745,126 B2
(45) Date of Patent: Jun. 29, 2010

(54) METHODS, KITS AND COMPOSITIONS PERTAINING TO COMBINATION OLIGOMERS AND LIBRARIES FOR THEIR PREPARATION

(75) Inventors: James M. Coull, Westford, MA (US);
Mark J. Fiandaca, Princeton, MA (US);
Mark D. Kristjanson, Auburndale, MA (US); Jens J. Hyldig-Nielsen, Moss Beach, CA (US); Theresa S. Creasey, Bedford, MA (US)

(73) Assignee: Boston Probes, Inc., Bedford, MA (US)

( * ) Notice: Subject to any disclaimer, the term of this patent is extended or adjusted under 35 U.S.C. 154(b) by 621 days.

(21) Appl. No.: 11/616,141

(22) Filed: Dec. 26, 2006

(65) Prior Publication Data

US 2008/0085837 A1    Apr. 10, 2008

Related U.S. Application Data

(62) Division of application No. 10/096,125, filed on Mar. 9, 2002, now Pat. No. 7,256,275.

(60) Provisional application No. 60/274,547, filed on Mar. 9, 2001.

(51) Int. Cl.
*C12Q 1/68* (2006.01)
*C07H 21/00* (2006.01)
*C07H 21/02* (2006.01)
*C07H 21/04* (2006.01)

(52) U.S. Cl. .................... 435/6; 536/23.1; 536/24.3; 536/25.3; 536/26.6

(58) Field of Classification Search .................. 435/6; 536/23.1, 24.3, 25.3, 26.6
See application file for complete search history.

(56) References Cited

U.S. PATENT DOCUMENTS

| 4,683,202 | A | 7/1987 | Mullis .................... 435/91 |
| 5,188,934 | A | 2/1993 | Menchen et al. ............. 435/6 |
| 5,252,293 | A | 10/1993 | Drbal et al. ................ 422/101 |
| 5,366,860 | A | 11/1994 | Bergot et al. ................ 435/6 |
| 5,527,675 | A | 6/1996 | Coull et al. .................. 435/6 |
| 5,539,082 | A | 7/1996 | Nielsen et al. ............ 530/300 |
| 5,539,083 | A | 7/1996 | Cook et al. ................ 530/333 |
| 5,612,458 | A | 3/1997 | Hyldig-Nielsen et al. ......... 530/388.21 |
| 5,623,049 | A | 4/1997 | Löbberding et al. ......... 530/300 |

(Continued)

FOREIGN PATENT DOCUMENTS

DE    3943522    2/1991

(Continued)

OTHER PUBLICATIONS

Buhler, C. et al, Template switching between PNA and RNA oligonucleotides. Nature, 376, 578-581, (1995).

(Continued)

*Primary Examiner*—Jezia Riley
(74) *Attorney, Agent, or Firm*—Townsend and Townsend and Crew LLP

(57) ABSTRACT

This invention pertains to the field of combination oligomers, including the block synthesis of combination oligomers in the absence of a template, as well as related methods, kits, libraries and other compositions.

27 Claims, 33 Drawing Sheets

No Gap; Linker bulges out, oligomer block termini are juxtaposed: Oligomer blocks hybridize to contiguous nucleobases of target sequence.

Oligomer blocks are seperated by the gap or gap base; Oligomer blocks do not hybridize to contiguous nucleobases of target sequence.

U.S. PATENT DOCUMENTS

| | | | | |
|---|---|---|---|---|
| 5,700,922 | A | 12/1997 | Cook et al. | 536/23.1 |
| 5,714,331 | A | 2/1998 | Buchardt et al. | 435/6 |
| 5,736,336 | A | 4/1998 | Buchardt et al. | 435/6 |
| 5,766,855 | A | 6/1998 | Buchardt et al. | 435/6 |
| 5,786,461 | A | 7/1998 | Buchardt et al. | 536/18.7 |
| 5,817,811 | A | 10/1998 | Breipohl et al. | 544/264 |
| 5,831,014 | A | 11/1998 | Cook et al. | 530/350 |
| 5,837,459 | A | 11/1998 | Berg et al. | 435/6 |
| 5,847,162 | A | 12/1998 | Lee et al. | 549/227 |
| 5,864,010 | A | 1/1999 | Cook et al. | 530/300 |
| 5,891,625 | A | 4/1999 | Buchardt et al. | 435/6 |
| 5,936,087 | A | 8/1999 | Benson et al. | 546/33 |
| 5,972,610 | A | 10/1999 | Buchardt et al. | 435/6 |
| 5,986,053 | A | 11/1999 | Ecker et al. | 530/350 |
| 6,008,379 | A | 12/1999 | Benson et al. | 549/224 |
| 6,020,132 | A | 2/2000 | Orum et al. | 435/6 |
| 6,020,481 | A | 2/2000 | Benson et al. | 536/26.6 |
| 6,051,719 | A | 4/2000 | Benson et al. | 548/416 |
| 6,063,569 | A | 5/2000 | Gildea et al. | 435/6 |
| 6,080,418 | A | 6/2000 | Nielsen et al. | 548/100 |
| 6,107,470 | A | 8/2000 | Nielsen et al. | 536/23.1 |
| 6,110,676 | A | 8/2000 | Coull et al. | 435/6 |
| 6,140,500 | A | 10/2000 | Yan et al. | 544/99 |
| 6,191,278 | B1 | 2/2001 | Lee et al. | 546/41 |
| 6,248,884 | B1 | 6/2001 | Lam et al. | 544/59 |
| 6,280,964 | B1 | 8/2001 | Kavanaugh et al. | 435/7.8 |
| 6,287,772 | B1 | 9/2001 | Stefano et al. | 435/6 |
| 6,297,016 | B1 | 10/2001 | Egholm et al. | 435/6 |
| 6,326,468 | B1 | 12/2001 | Canne et al. | 530/333 |
| 6,326,479 | B1 | 12/2001 | Gildea et al. | 536/23.1 |
| 6,433,134 | B1 | 8/2002 | Patron et al. | 530/300 |
| 6,469,151 | B1 | 10/2002 | Egholm et al. | 536/23.1 |
| 6,756,199 | B1 | 6/2004 | Cook et al. | 435/4 |
| 7,256,275 | B2 | 8/2007 | Coull et al. | |
| 2003/0082558 | A1 | 5/2003 | Egholm et al. | |

FOREIGN PATENT DOCUMENTS

| | | |
|---|---|---|
| EP | 237362 | 3/1987 |
| EP | 0733206 | 4/1998 |
| EP | 0857791 | 8/1998 |
| EP | 0897991 | 2/1999 |
| WO | WO9220702 | 11/1992 |
| WO | WO9220703 | 11/1992 |
| WO | WO9514706 | 6/1995 |
| WO | WO9602558 | 2/1996 |
| WO | WO9604000 | 2/1996 |
| WO | WO9640709 | 12/1996 |
| WO | WO9745539 | 12/1997 |
| WO | WO9921881 | 5/1999 |
| WO | WO9922018 | 5/1999 |
| WO | WO9937670 | 7/1999 |
| WO | WO9941273 | 8/1999 |
| WO | WO9949293 | 9/1999 |
| WO | WO9955916 | 11/1999 |
| WO | WO0131063 | 5/2001 |

OTHER PUBLICATIONS

Boston Probes press release, Bedford, MA Jun. 25, 2001.
Corey, David, Peptide nucleic acids: expanding the scope of nucleic acid recognition. Tibtech, 15, 224-229, (1997).
Dunn, J. et al., Ligation of Hexamers on Hexamer Templates to Produce Primers for Cycle Sequencing or the Polymerase Chain Reaction. Analytical Biochemistry, 228, 91-100, (1995).
Far?se, A. et al, Liquid Phase Synthesis of a Peptide Nucleic Acid Dimer. Tetrahedron Letters, 9, 1413-1416, (1996).
Fiandaca, M. et al, Pna Blocker Probes Enhance Specificity In Probe Assays. Peptide Nucleic Acids, 3.4, 129-141, (1999).
Gildea, B. et al, PNA Solubility Enhancers. Tetrahedron Letters, 39, 7255-7258, (1998).
Guo, Z. et al, Enhanced discrimination of a single nucleotide polymorphisms by artificial mismatch hybridization, Nature Biotechnology, 15, 331-335, (1997).
Kaczorowski, T. et al, Assembly of 18-Nucleotide Primers by Ligation of Three Hexamers: Sequencing of Large Genomes by Primer Walking. Analytical Biochemistry, 221, 127-135, (1994).
Koppitz, M. et al, Formation of Oligonucleotide-PNA-Chimeras by Template-Directed Ligation. J. Am. Chem. Soc., 120, 4563-4569, (1998).
Kotler, L. et al, DNA Squencing: Modular primers assembled from a library of hexamers or pentamers. Proc. Natl. Acad. Sci. USA, 90, 4241-4245, (1993).
Kotler, L. et al, DNA Sequencing: Modular Primers for Automated Walking. BioTechniques, 3, 554-558, (1994).
Kumar, V. et al, Pyrrolidine Nucleic Acids: DNA/PNA Oligomers with 2-Hydroxy/Aminomethyl-4-(thymin-1-yl)pyrrolidine-N-acetic acid. Organic Letters, 9, 1269-1272, (2001).
Lu, W. et al, Comparative Total Syntheses of Turkey Ovomucoid Third Domain by Both Stepwise Solid Phase Peptide Syntheses and Native Chemical Ligation. J. Am. Chem. Soc., 118, 8518-8523, (1996).
Lutz, M. et al, Recognition of Uncharged Polyamide-Linked Nucleic Acid Analogs by DNA Polymerases and Reverse Transcriptases. J. Am.Chem. Soc., 119, 3177-3178, (1997).
Mattes, A. et al, Sequence fidelity of a template-directed PNA-ligation reaction. Chem. Commun., 2050-2051, (2001).
Muir, T. et al, Protein Synthesis by Chemical Ligation of Unprotected Peptides In Aqueous Solution. Methods In Enzymology, 289, 266-298, (1997).
Nielsen, P. et al, Peptide Nucleic Acid. A Molecule with Two Identities. Accounts of Chemical Research, 7, 624-630, (1999).
Nielsen, P. et al, peptide Nucleic Acids: A New Dimension to Peptide Libraries and Aptamers. Methods In Enzymology, 267, 426-433, (1996).
Nilsson, P. et al, Quantitative Investigation of the Modular Primer Effect for DNA and Peptide Nucleic Hexamers. Analytical Biochemistry, 269, 155-161, (1999).
PerSeptive Biosystems 1997-1998 Synthesis Products Catalog. p. 45.
PerSeptive Biosystems Promotional Literature. Bio ConSepts. vol. 4, No. 3. Publication #NL612 (1996).
PerSeptive Biosystems Promotional Literature. Practical PNA. vol. 1, Iss. 2. PNA Oligomers as hybridization probes. Publication #PN003 (1995).
PerSeptive Biosystems Promotional Literature. Practical PNA, Review. Peptide Nucleic Acids (PNA): Expanding the role of synthetic DNA analogs. Publication #PN001 (1995).
Roll, C., et al, Conformations of Nicked and Gapped DNA Structures by NMR and Molecular Dynamic Simulations In Water. Biochemistry, 37, 4059-4070, (1998).
Schmidt, J. et al, Enantiomeric Cross-Inhibition In the Synthesis of Oligonucleotides on a Nonchiral Template. J. Am. Chem. Soc., 119, 1494-1495, (1997).
Schmidt, J. et al, Information transfer from DNA to peptide nucleic acids by template-directed syntheses. Nucleic Acids Research, 23, 4792-4796, (1997).
Schmidt, J. et al, Information transfer from peptide nucleic acids to RNA by template-directed syntheses. Nucleic Acids Research, 23, 4797-4802, (1997).
Seela, F. et al, The $N^8$-(2'-deoxyribofuranoside) of 8-aza-7-deazaadenine: a universal nucleoside forming specific hydrogen bonds with the four canonical DNA constituents. Nucleic Acids Research, 17, 3224-3232, (2000).
Xu, Y. et al, Nonenzymatic autoligation In direct three-color detection of RNA and DNA point mutations. Nature Biotechnology, 19, 148-152, (2001).
Altmann, K., et al, Polyamide Based Nucleic Acid Analogs- Synthesis of ?-Amino Acids with Nucleic Acid Bases Bearing Side Chains. Bioorganic & Medicinal Chemistry Letters, 9, 1119-1122, (1997).
Cantin, M. et al, Synthesis of the Monomeric Building Blocks of Z-Olefinic PNA (Z-OPA) Containing the Bases Adenine and Thymine. Tett. Letters, 24, 4211-4214 (1997).

Ciapetti, P. et al, Synthesis of N-Fmoc-α-AMino Acids Carrying the Four DNA Nucleobases In the Side Chain. Tetrahedron, 53, 1167-1176 (1997).

Diederichsen, Ulf, Alanyl-PNA Homoduplex: A-T Pairing With The N7-Regiosomer Of Adenine. Bioorganic & Medicianal Chemistry Letters, 8, 165-168, (1998).

Diederichse, Ulf, Alanyl-PNA Oligomers: A New System for Intercalation. Bioorganic & Medicinal Chemistry Letters, 7, 1743-1746 (1997).

Diederichse, U. et al, ?-Homoalanyl PNAs:Synthesis and Indication of Higher Ordered Structures. Angew. Chem Int. Ed, 3, 302-305, (1998).

Diederichsen, Ulf, Self-Pairing PNA With Alternating Alanyl/Homoalanyl Backbone. Tetrahedron Letters, 4, 475-478 (1996).

Egholm, M. et al, PNA Hybridizes to complementary oligonucleotides obeying the Watson-Crick hydrogen-bonding rules. Nature, 365, 566-568 (1993).

Fujii, M. et al, Nucleic Acid Analog Peptide (NAAP)2. Syntheses And Properties Of Novel DNA Analog Peptides Containing Nucleobase Linked ?-Aminoalanine. Bioorganic & Medicinal Letters, 5, 637-640 (1997).

Gilliland, G. et al, Analysis of cytokine mRNA and DNA: Detection and quantitation by competitive polymerase chain reaction. Proc. Natl. Acad. Sci., 87, 2725-2729 (1990).

Green, E. et al, Sequence-tagged Site (STS) Content Mapping of Human Chromosomes: Theoretical Considerations and Early Experiences. PCR Methods and Applications, 1, 77-90, (1991).

Howarth, N., et al, PNA: A Novel Peptide Nucleic Acid Analogue of DNA. J. Org. Chem, 62, 5441-5450 (1997).

Jordan, S., et al, New Hetero-Oligomeric peptide Nucleic Acids With Improved Binding Properties To Complementary DNA. Bioorganic & Medicinal Chemistry Letters, 6, 687-690 (1997).

Krotz, A., et al, Synthesis of "Retro-Inverso" Peptide Nucleic Acids: 2. Oligomerization and Stability. Tetrahedron Letters, 38, 6941-6944 (1995).

Lagriffoule, P., et al, Peptide Nucleic Acids with a Conformationally Constrained Chiral Cyslohexyl-Derived Backbone. Chem. Eur. J., 6, 912-919 (1997).

Lagriffoule, P., et al, The Synthesis, Co-oligomerization And Hybridization Of A Thymine-Thymine Heterodimer Containing PNA. Bioorganic Medicinal Chemistry Letters, 8, 1081-1082 (1994).

Lowe, G., et al, Amino Acids Bearing Nucleobases For The Synthesis Of Novel Peptide Nucleic Acids. J. Chem. Soc., 1, 539-546 (1997).

Lowe, G. et al, Dipetides Bearing Nucleobases For The Synthesis Of Novel Peptide Nucleic Acids. J. Chem. Soc., 1, 547-554 (1997).

Lowe, G. et al, Solid-phase synthesis of novel peptide nucleic acids. J Chem. Soc. 1, 555-560 (1997).

Lutz, M. et al, Recognition of Uncharged Polyamide-Linked Nucleic Acid Analogs by DNA Polymerases and Reverse Transcriptases. J Am. Chem. Soc., 119, 3177-3178, 1997.

Nielsen, P. Peptide Nucleic Acid. A Molecule with Two Identities. Acc. Chem. Res., 32, 624-630 (1999).

Petersen, K., et al, Synthesis and oligomerization of N?-Boc-N?-(thymin-1-ylacetyl)ornithine. Bioorganic & Medicinal Chemistry Letters, 7, 793-796 (1996).

Weiler, J. et al, Hybridisation based DNA screening on peptide nucleic acid (PNA) oligomer arrays. Nucleic Acids Research, 14, 2792-2799.

Yaron, A. et al, Intramolecularly Quenched Fluorogenic Substrates for Hydrolytic Enzymes. Analytical Biochemistry, 95, 228-235 (1979).

Igloi G., Variability In the stability of DNA-peptide nucleic acid (PNA) single-base mismatched duplexes: Real-time hybridization during affinity electrophoresis In PNA-containing gels. Proc. Natl. Acad. Sci. USA, 95, 8562-8567, (1998).

Egholm, M. et al, Efficient pH-Independent Sequence-Specific DNA Binding by Pseudoisocytosine-Containing Bis-PNA. Nucleic Acids Research, 2, 217-222 (1995).

Farese, A. et al, Liquid Phase Synthesis of a Peptide Nucleic Acid Dimer. Tetrahedron Letters, 9, 1413-1416 (1996).

Knudsen, H. et al, Antisense Properties of Duplex- and Triplex-Forming PNAs. Nucleic Acids Research, 3, 494-500 (1996).

Mardirossian, G. et al, In Vivo Hybridization of Technetium-99M-Labeled Peptide Nucleic Acid (PNA). Journal of Nuclear Medicine, Society of Nuclear Medicine, 38, 907-913 (1997).

Matysiak, S. et al, Automating Parallel Peptide Synthesis For The Production of PNA Library Arrays. BioTechniques, 31, 896-904 (2001).

Petersen, K. et al, A PNA-DNA Linker Synthesis of N-((4,4'-Dimethoxytrityloxy)Ethyl)-N-(Thymin-1-Ylacetyl) Glycine. Bioorganic & Med. Chem. Letters, 5, 1119-1124 (1995).

Uhlmann, E. et al, PNA/DNA Chimeras. Peptide Nucleic Acids: Protocols and Applications, 51-70 (1999).

Van Der Laan, AC et al, Optimization of the Binding Properties of PNA-(5') DNA Chimerae. Bioorganic & Medicinal Chemistry Letters, 8, 663-668 (1998).

Figure 1
No Gap; Linker bulges out, oligomer block termini are juxtaposed: Oligomer blocks hybridize to contiguous nucleobases of target sequence.
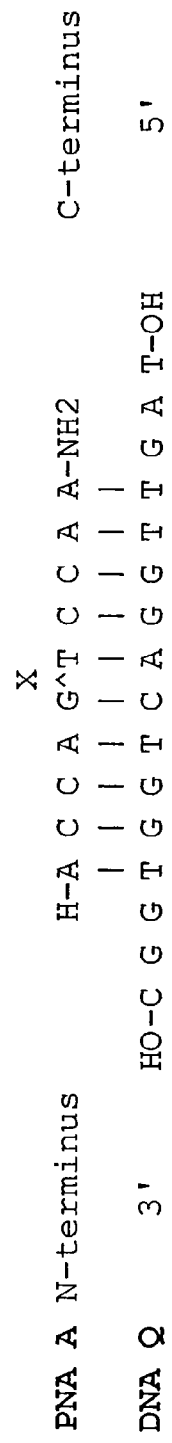
Oligomer blocks are seperated by the gap or gap base; Oligomer blocks do not hybridize to contiguous nucleobases of target sequence.
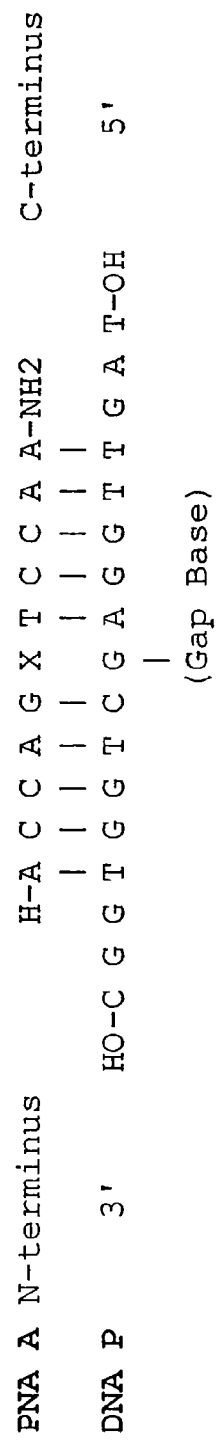

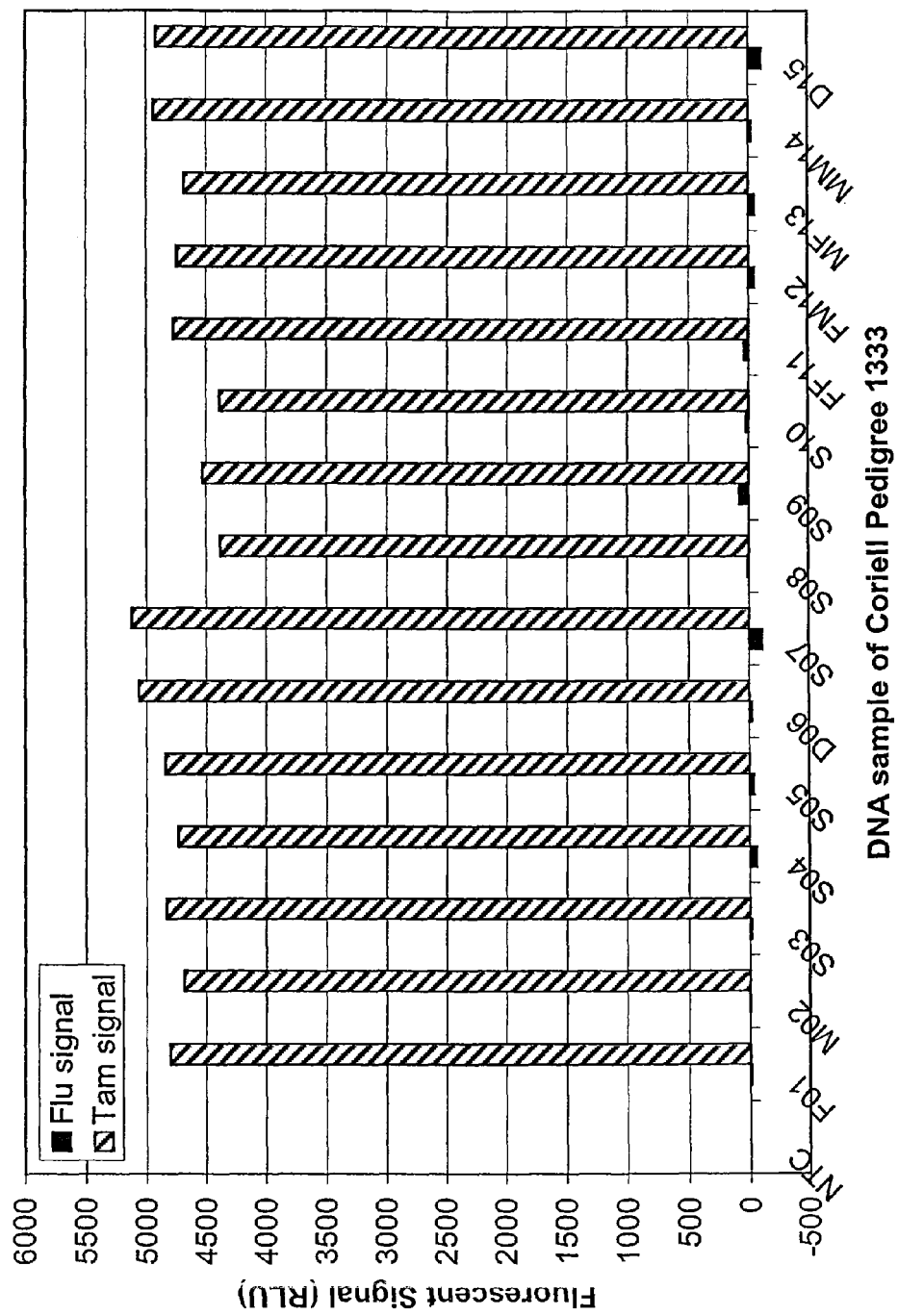

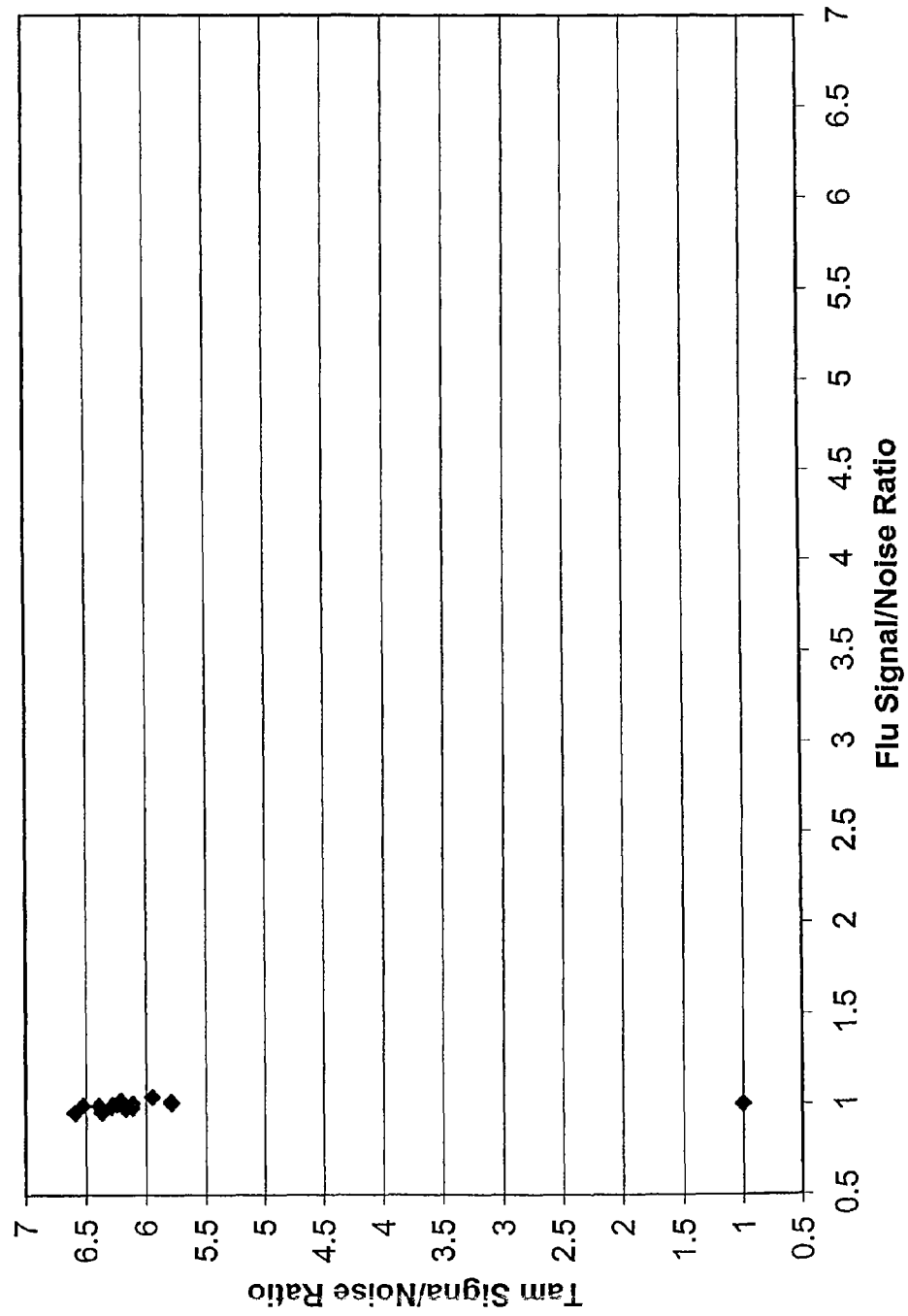
Figure 5. Allele distribution plot of SNP 6784 and Coriell Pedigree 1333.

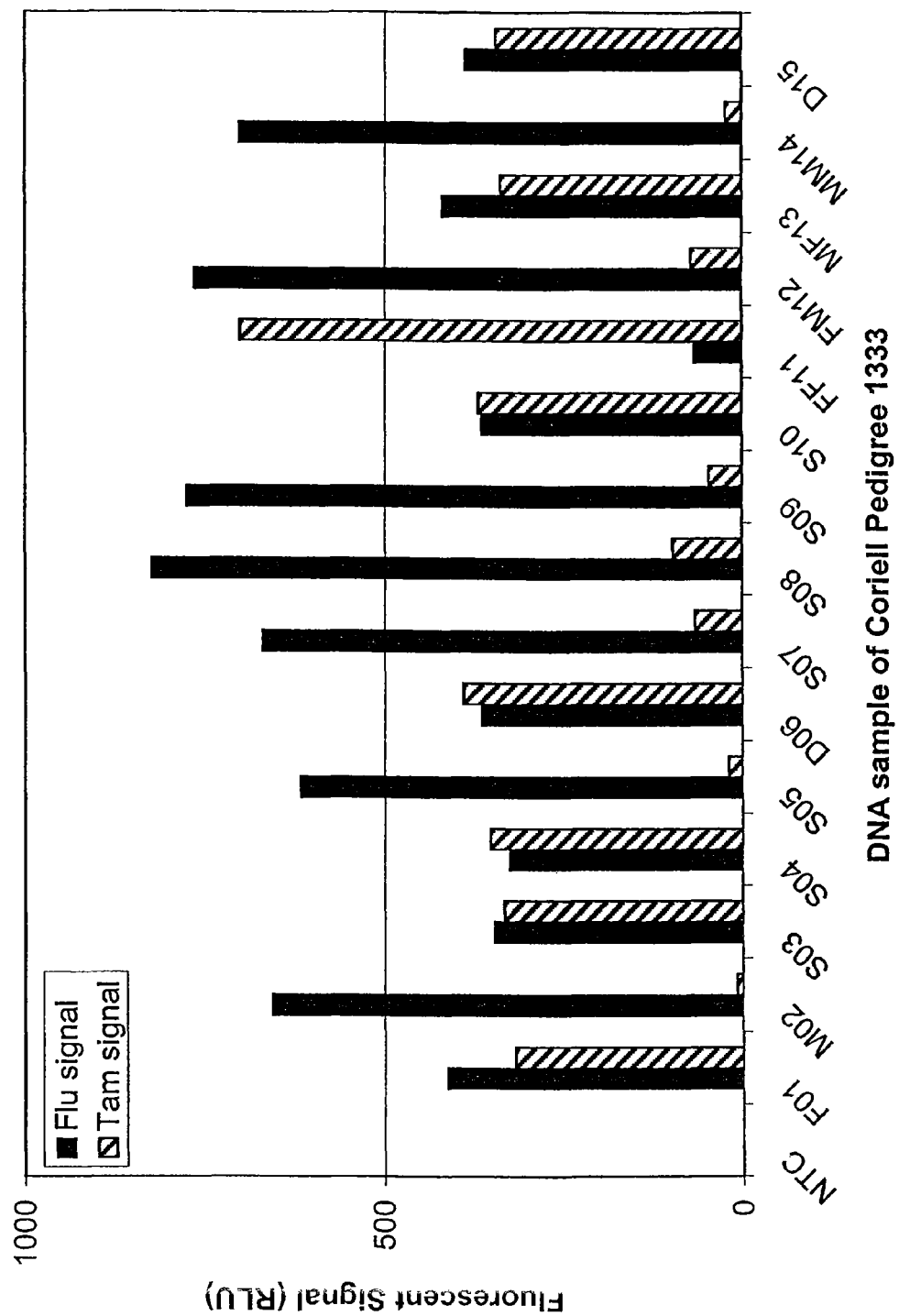

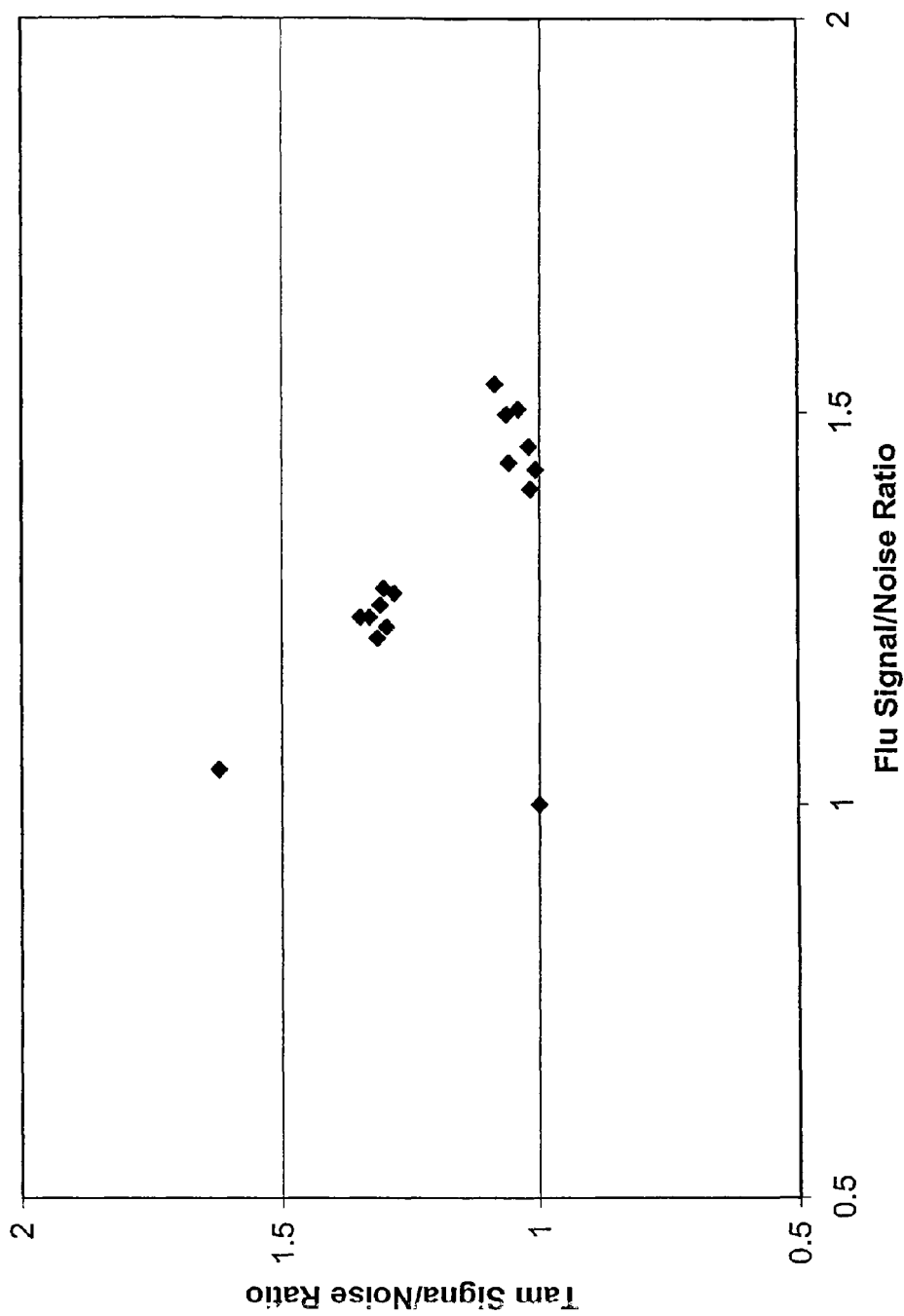

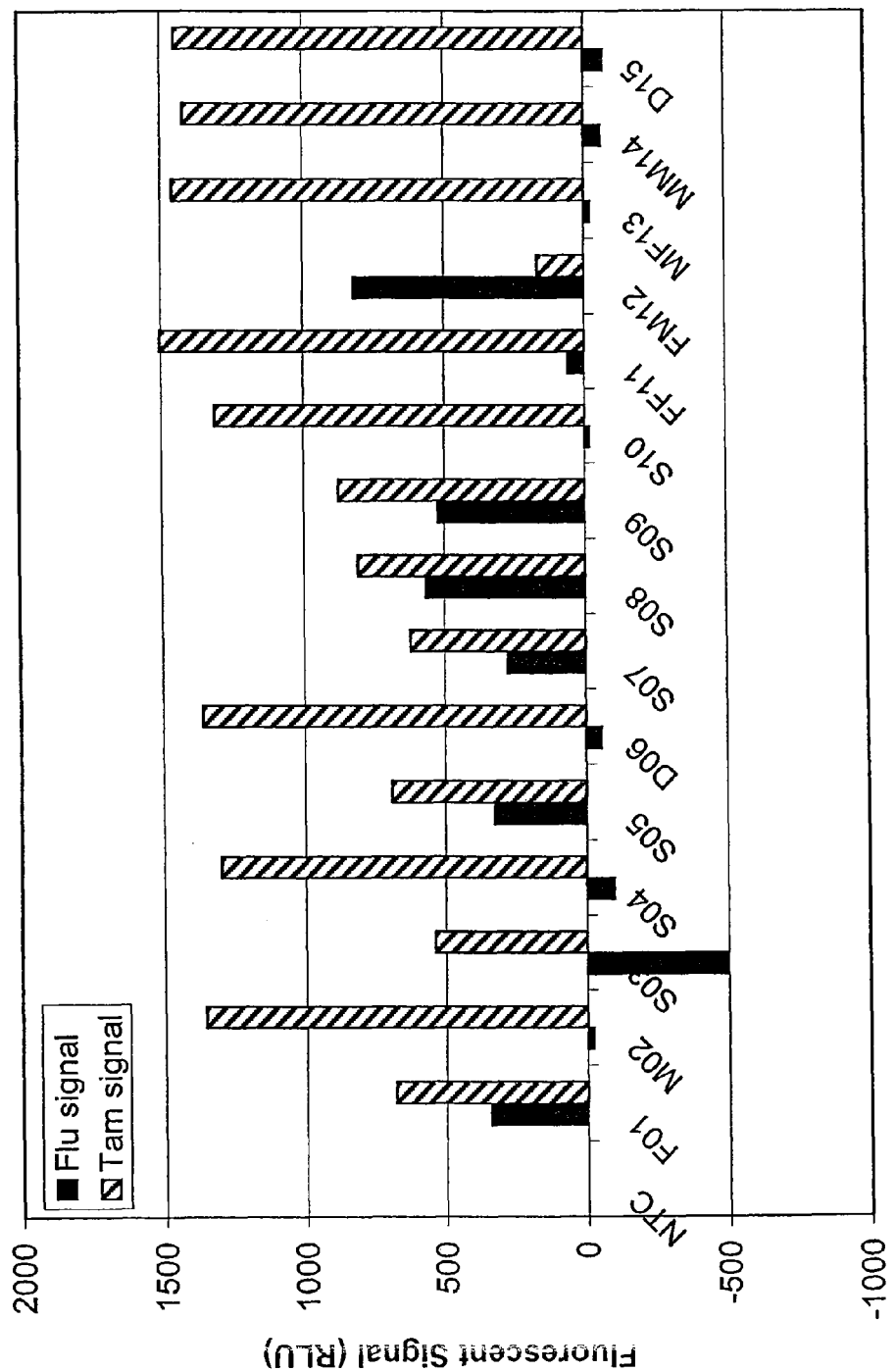

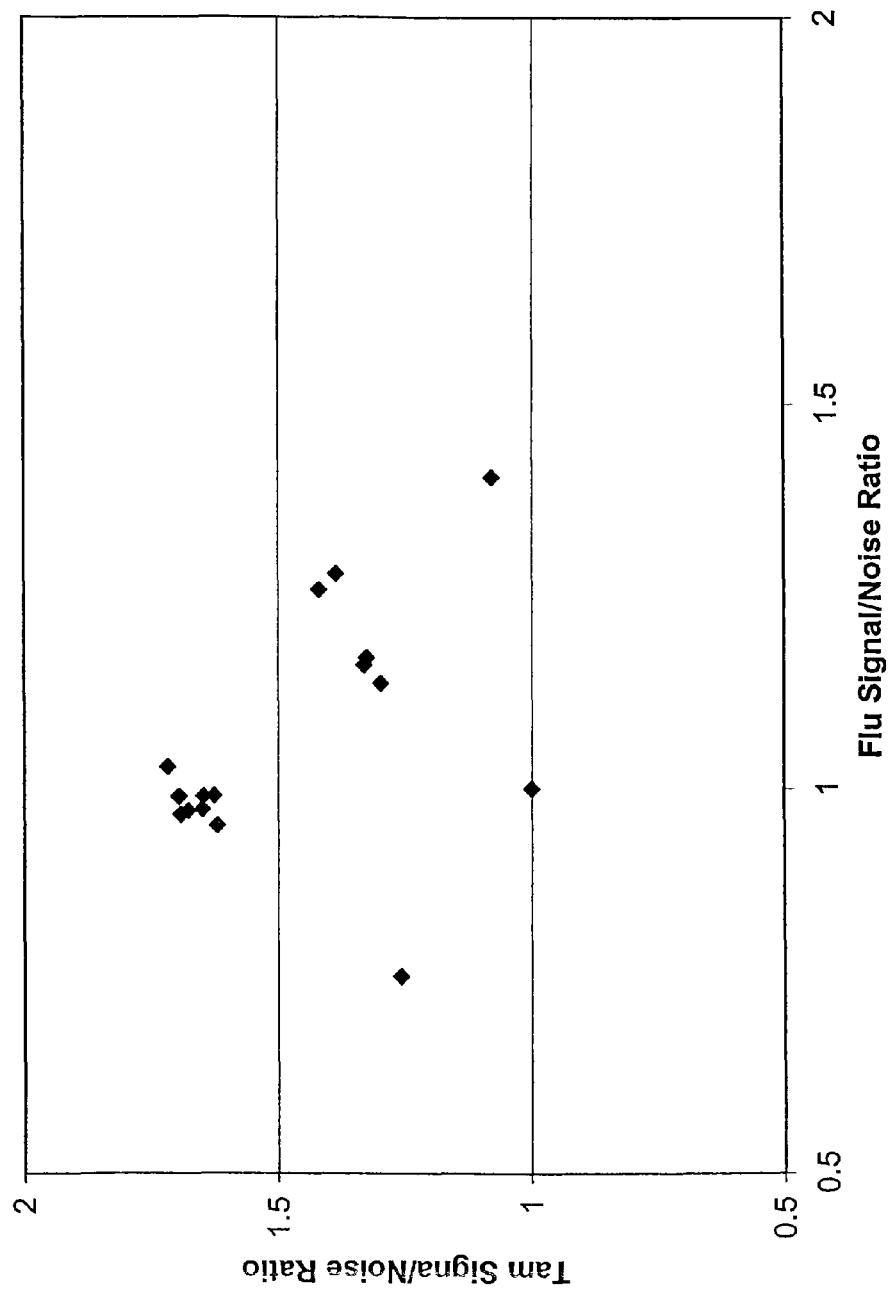
Figure 9. Allele distribution plot of SNP 6806 and Coriell Pedigree 1333.

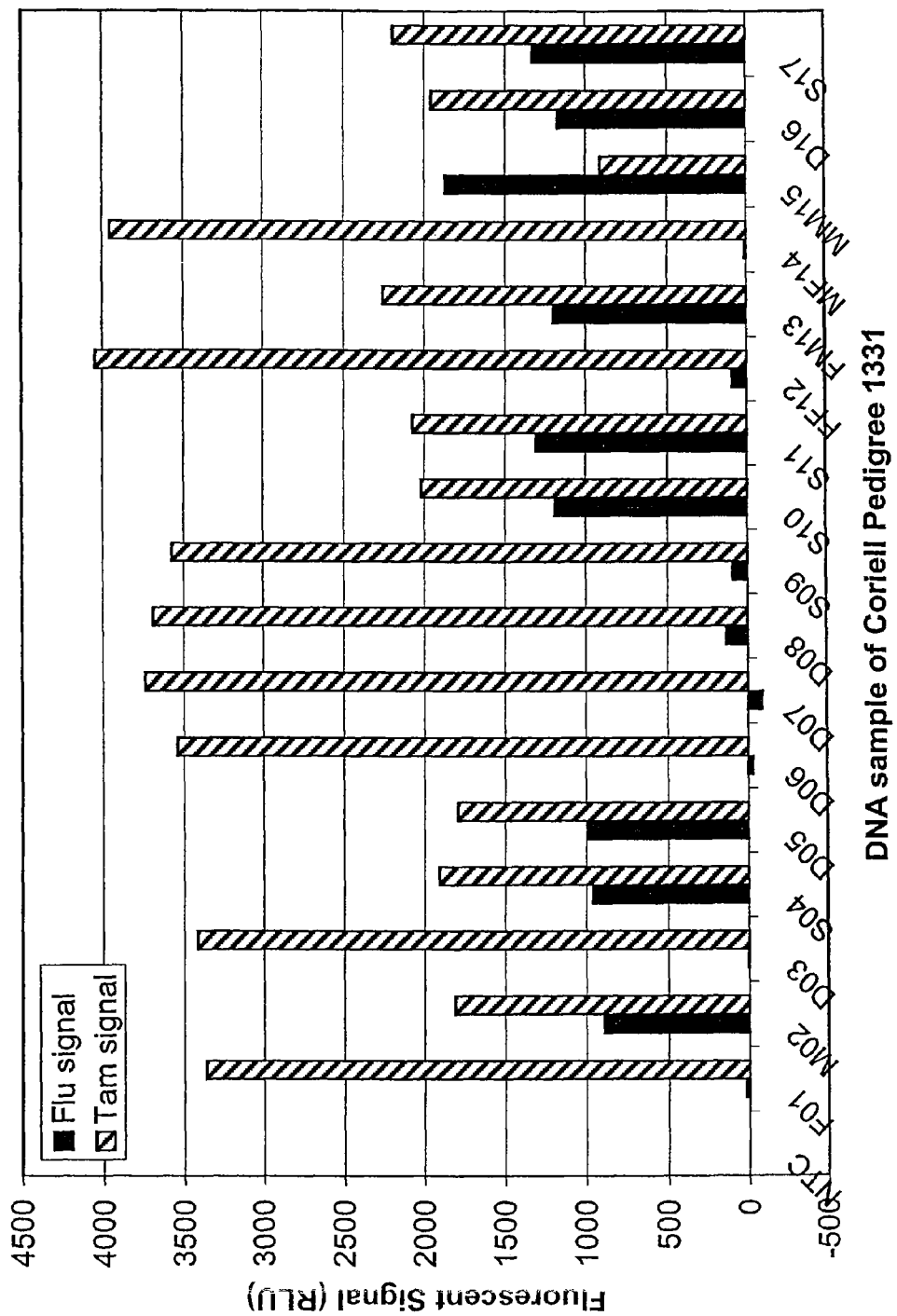
Figure 10. Bar graph of SNP 6834 and Coriell Pedigree 1331.

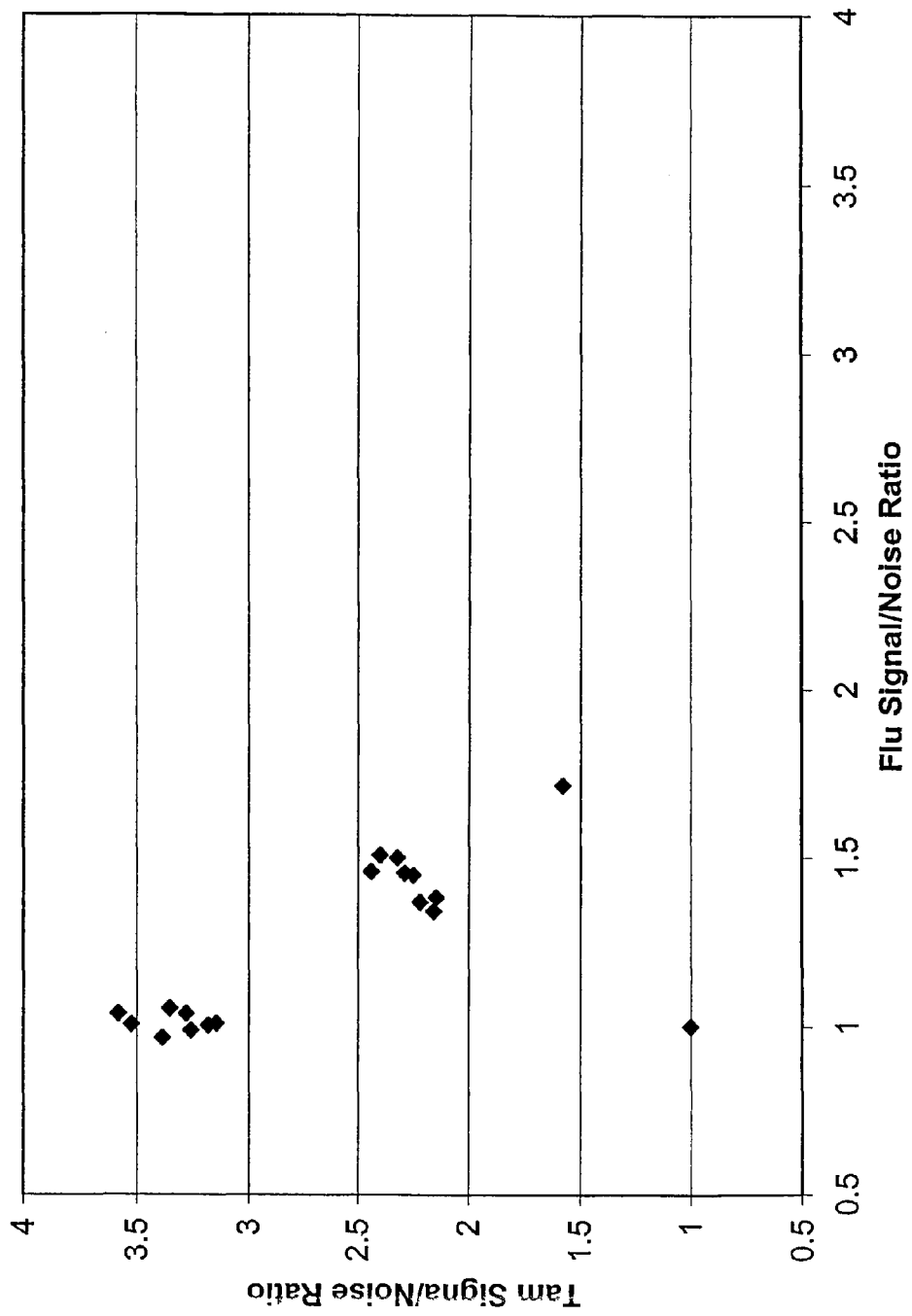
Figure 11. Allele distribution plot of SNP 6834 and Coriell Pedigree 1331.

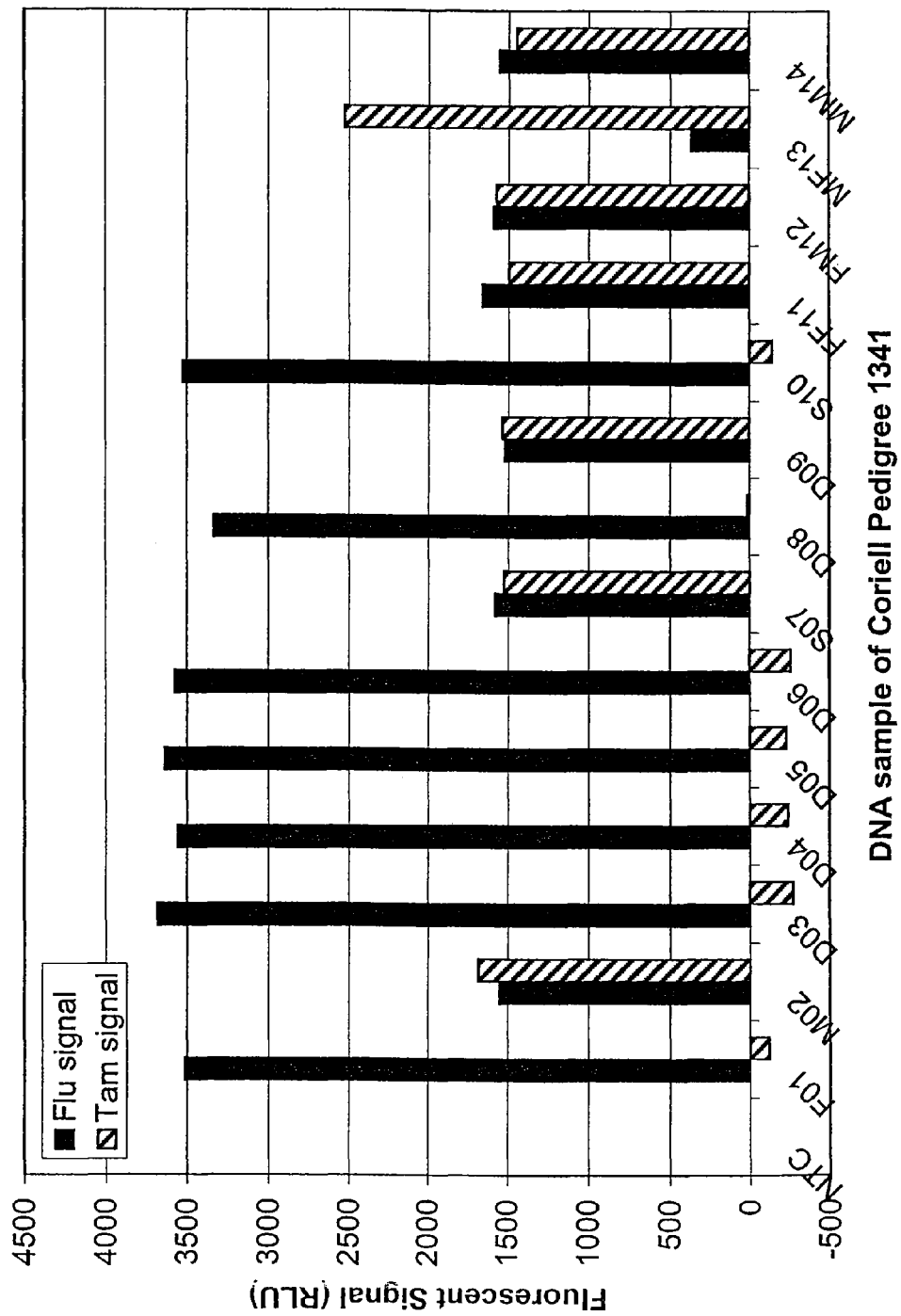

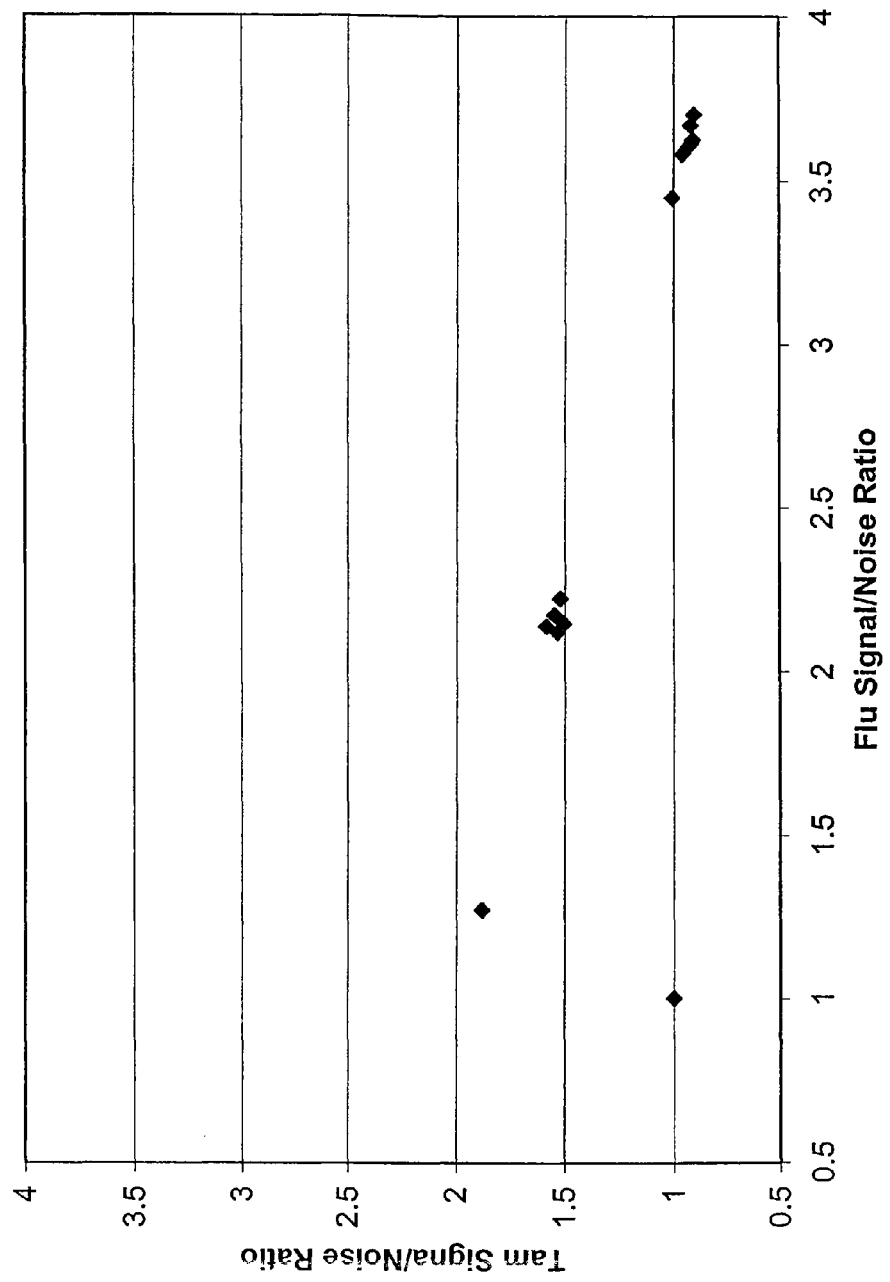
Figure 13. Allele distribution plot of SNP 6837 and Coriell Pedigree 1341.

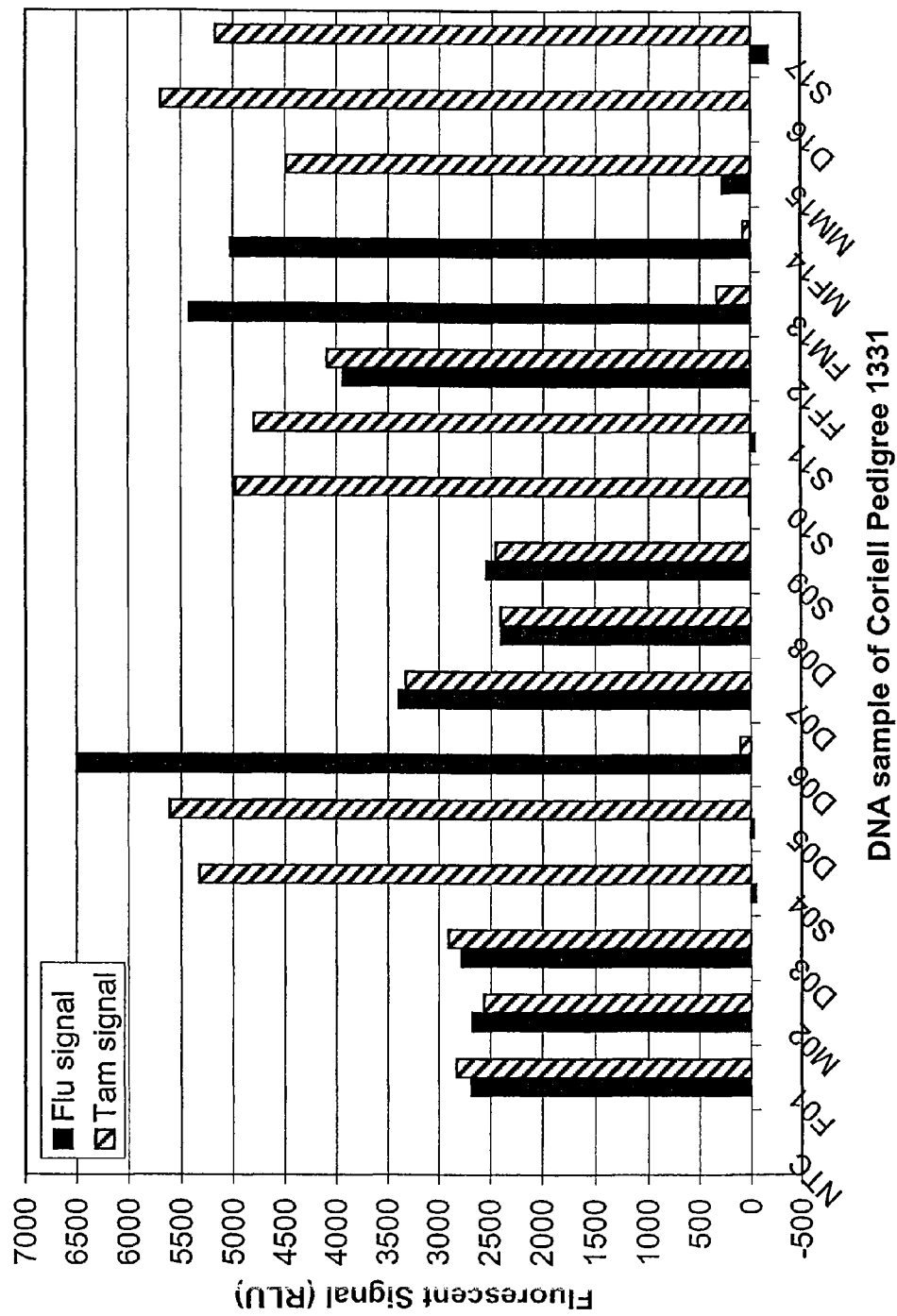

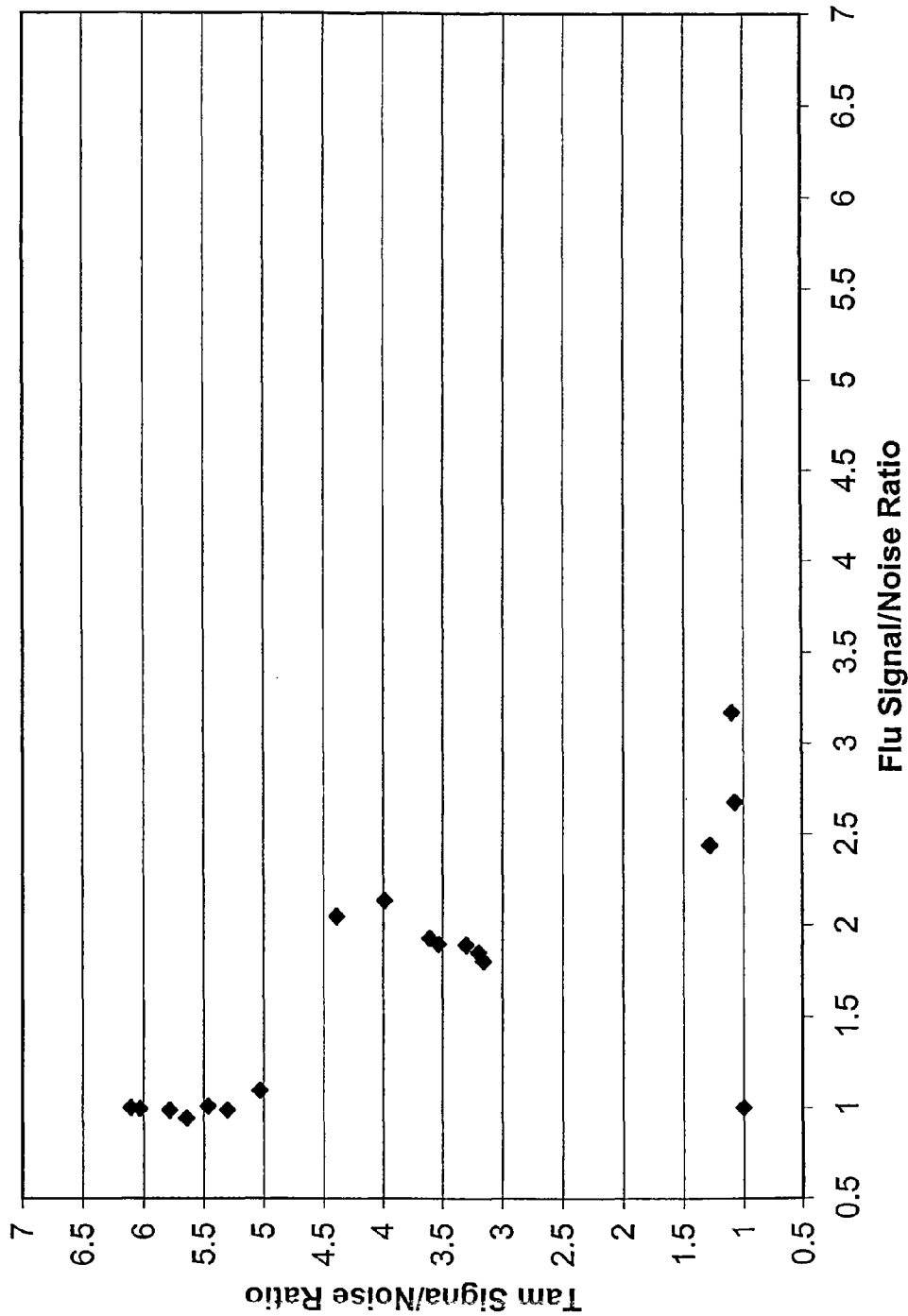
Figure 15. Allele distribution plot of SNP 6848 and Coriell Pedigree 1331.

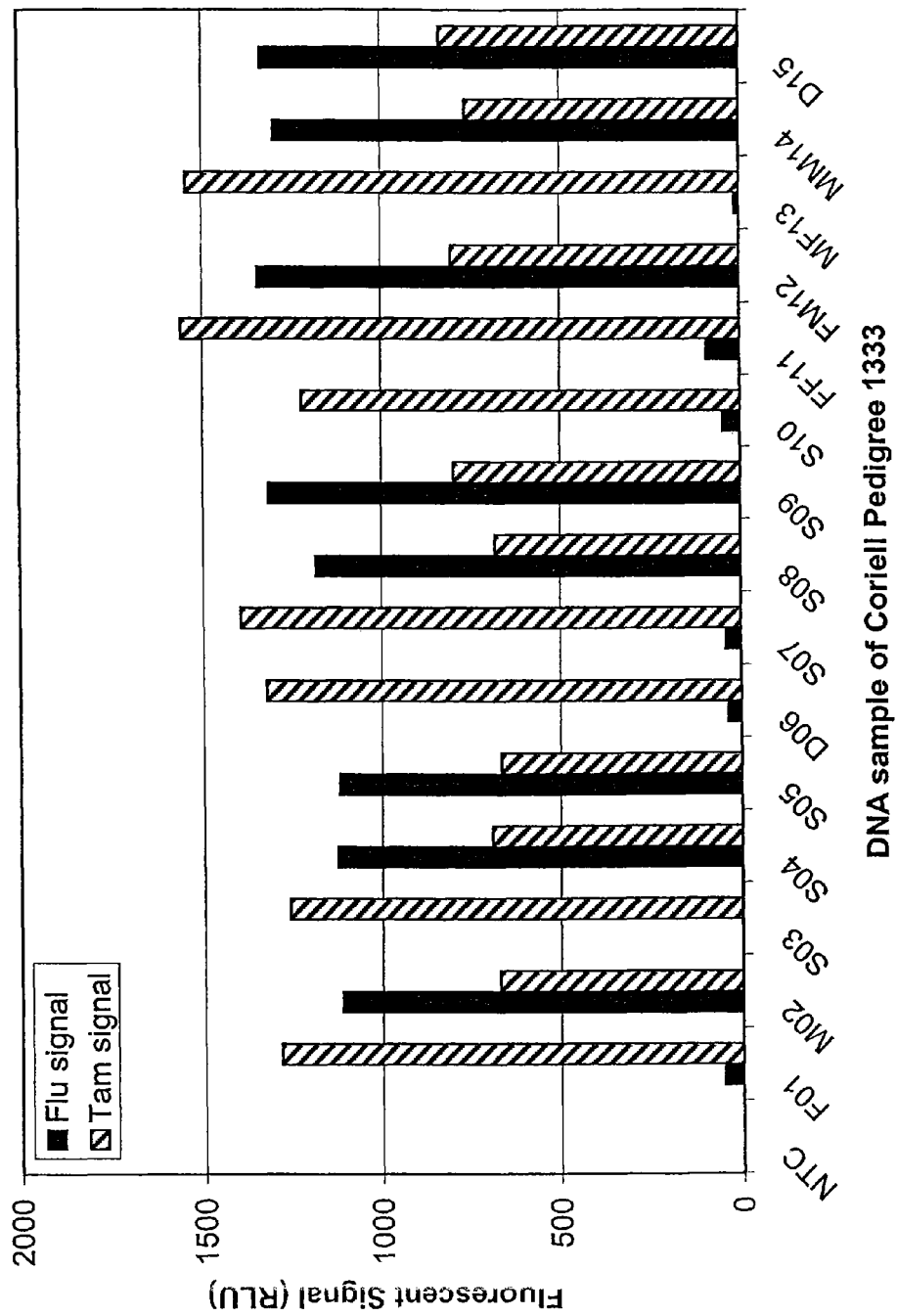
Figure 16. Bar graph of SNP 6876 and Coriell Pedigree 1333.

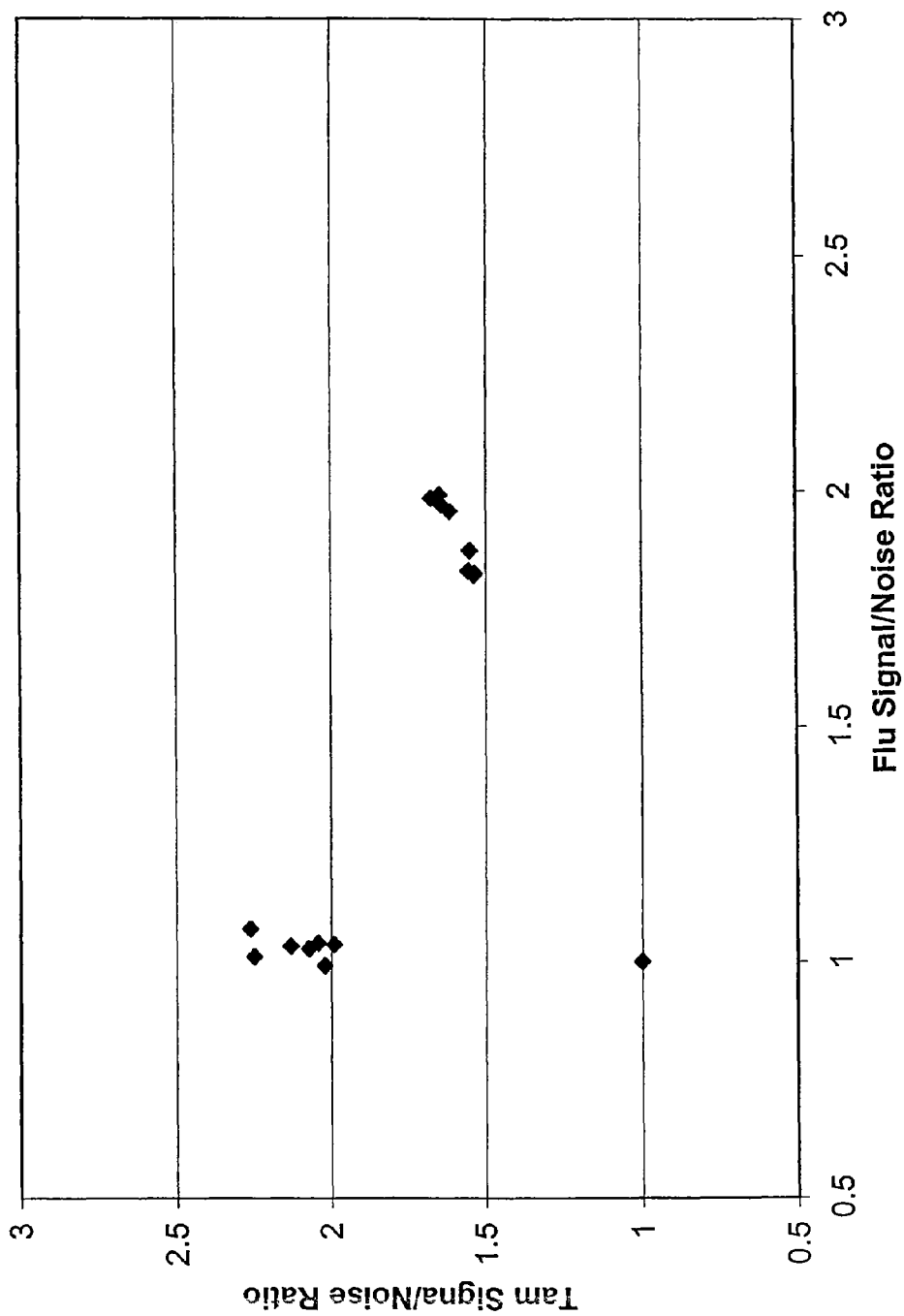
Figure 17. Allele distribution plot of SNP 6876 and Coriell Pedigree 1333.

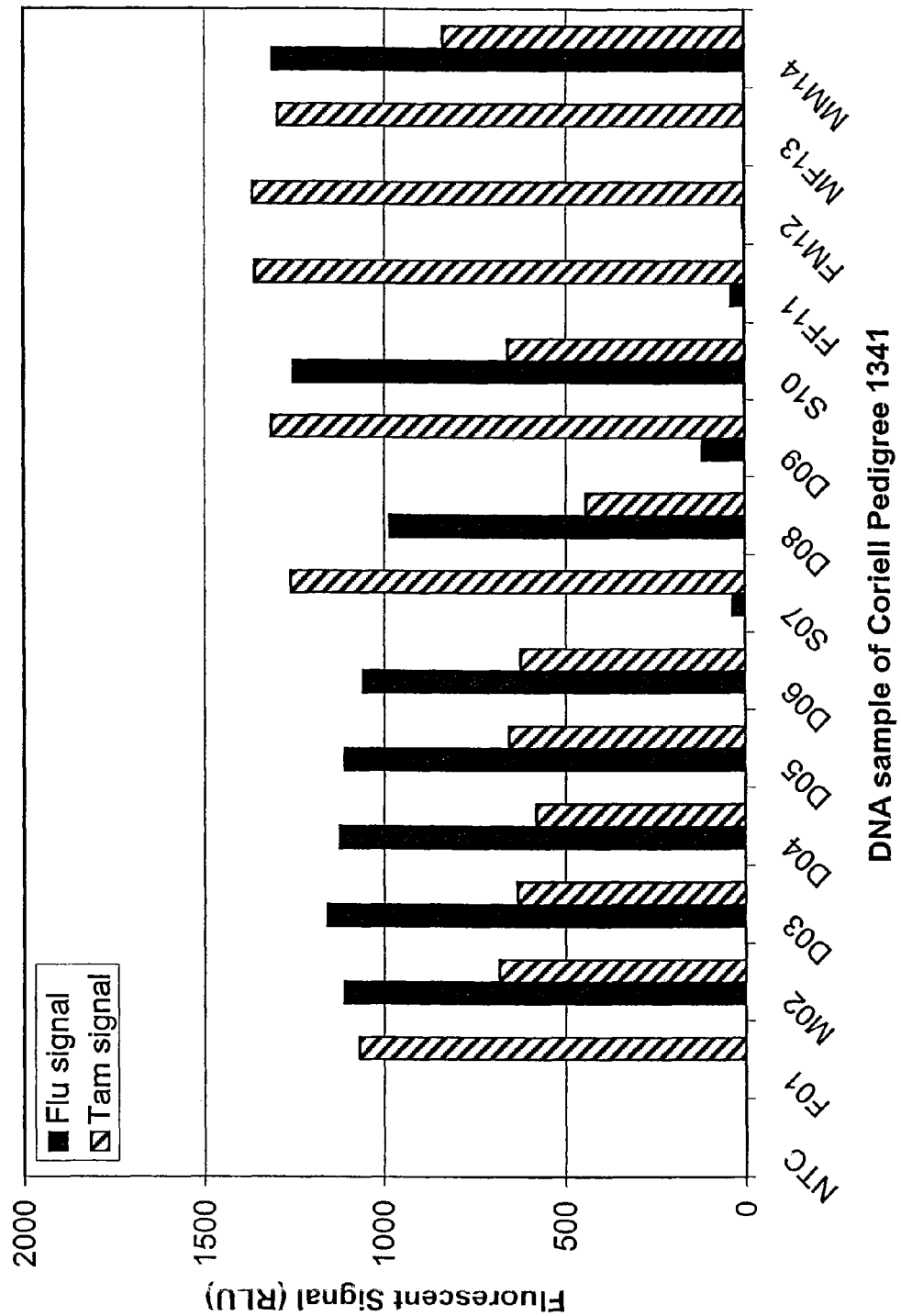
Figure 18. Bar graph of SNP 6876 and Coriell Pedigree 1341.

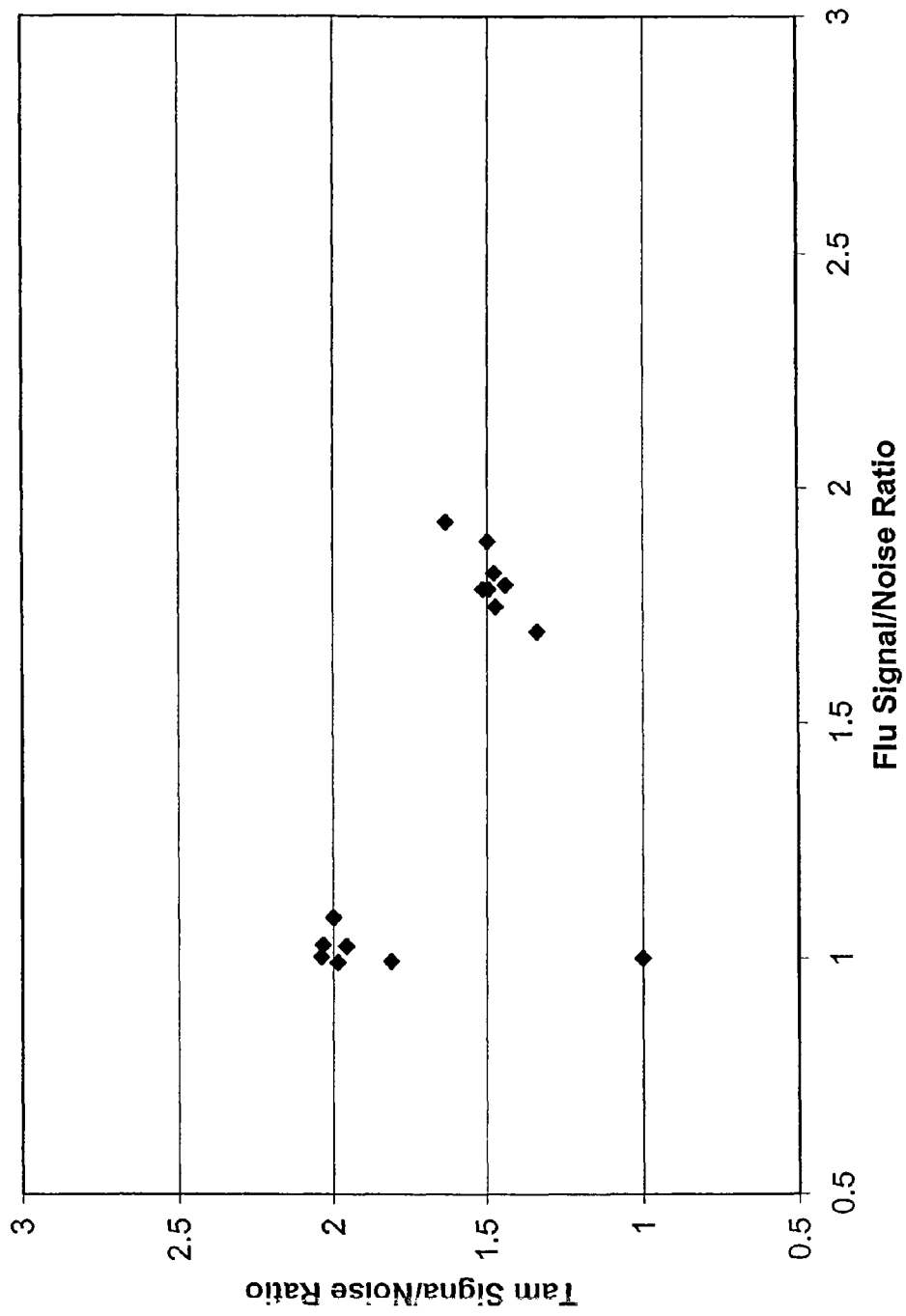
Figure 19. Allele distribution plot of SNP 6876 and Coriell Pedigree 1341.

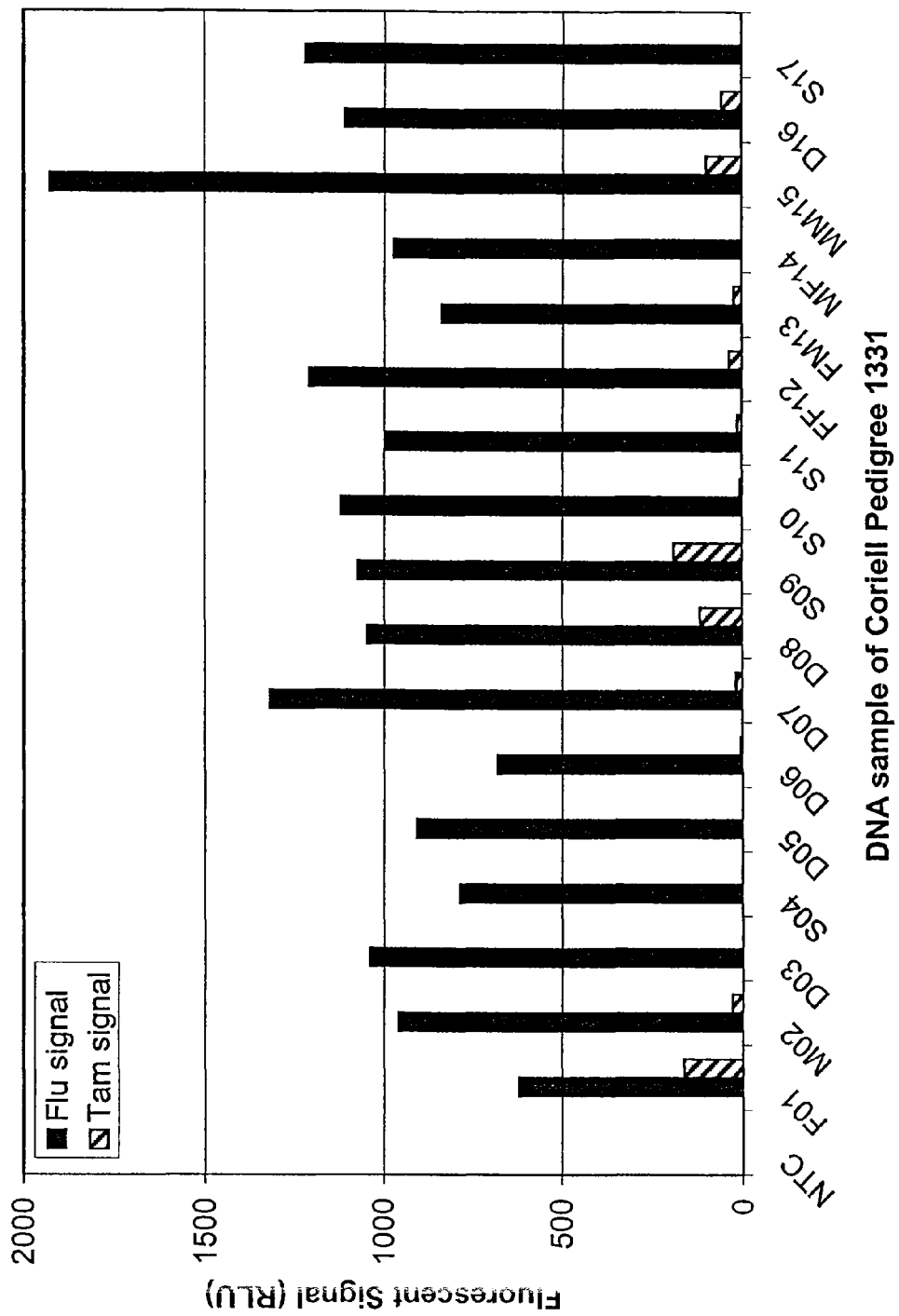

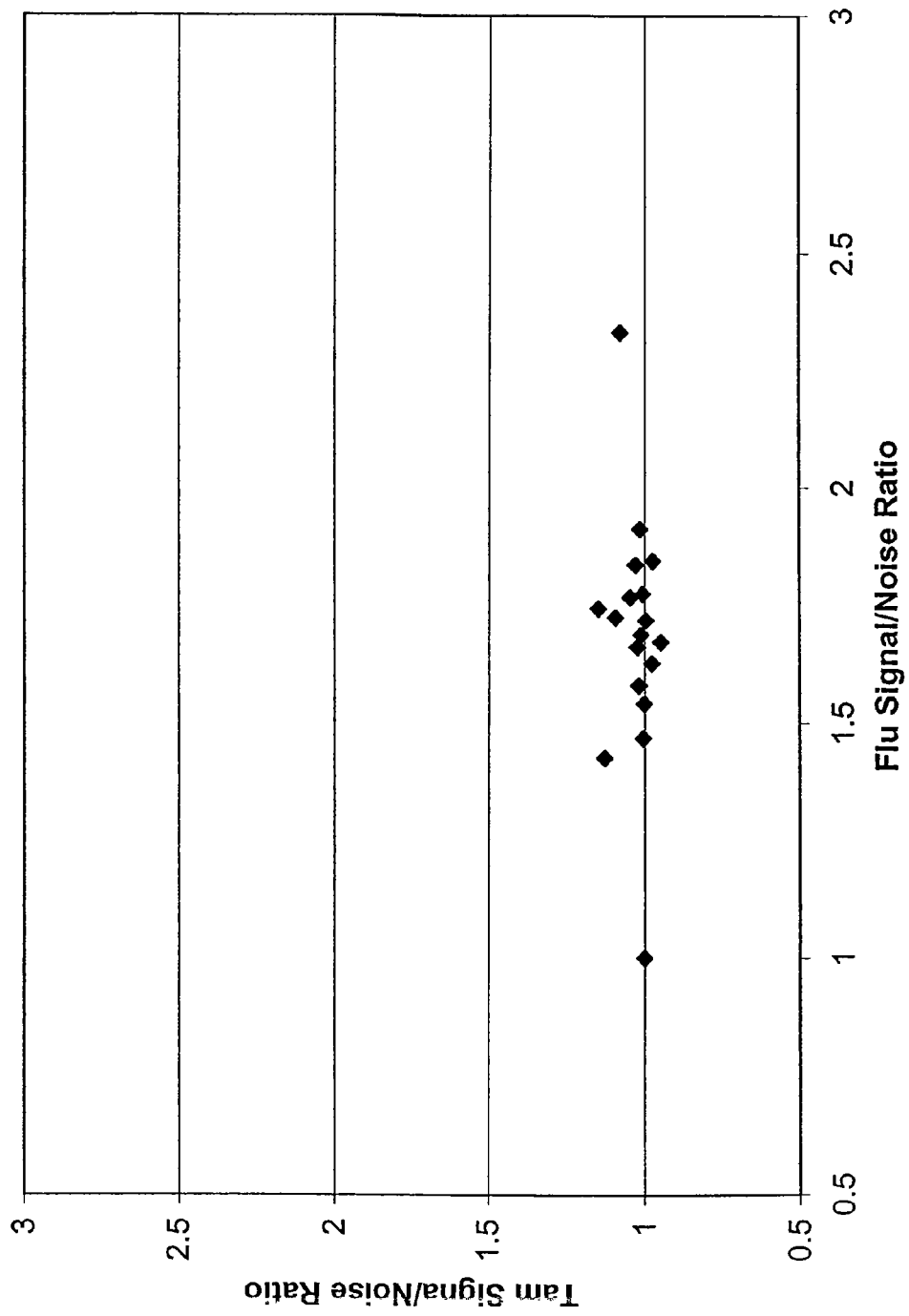
Figure 21. Allele distribution plot of SNP 6879 and Coriell Pedigree 1331.

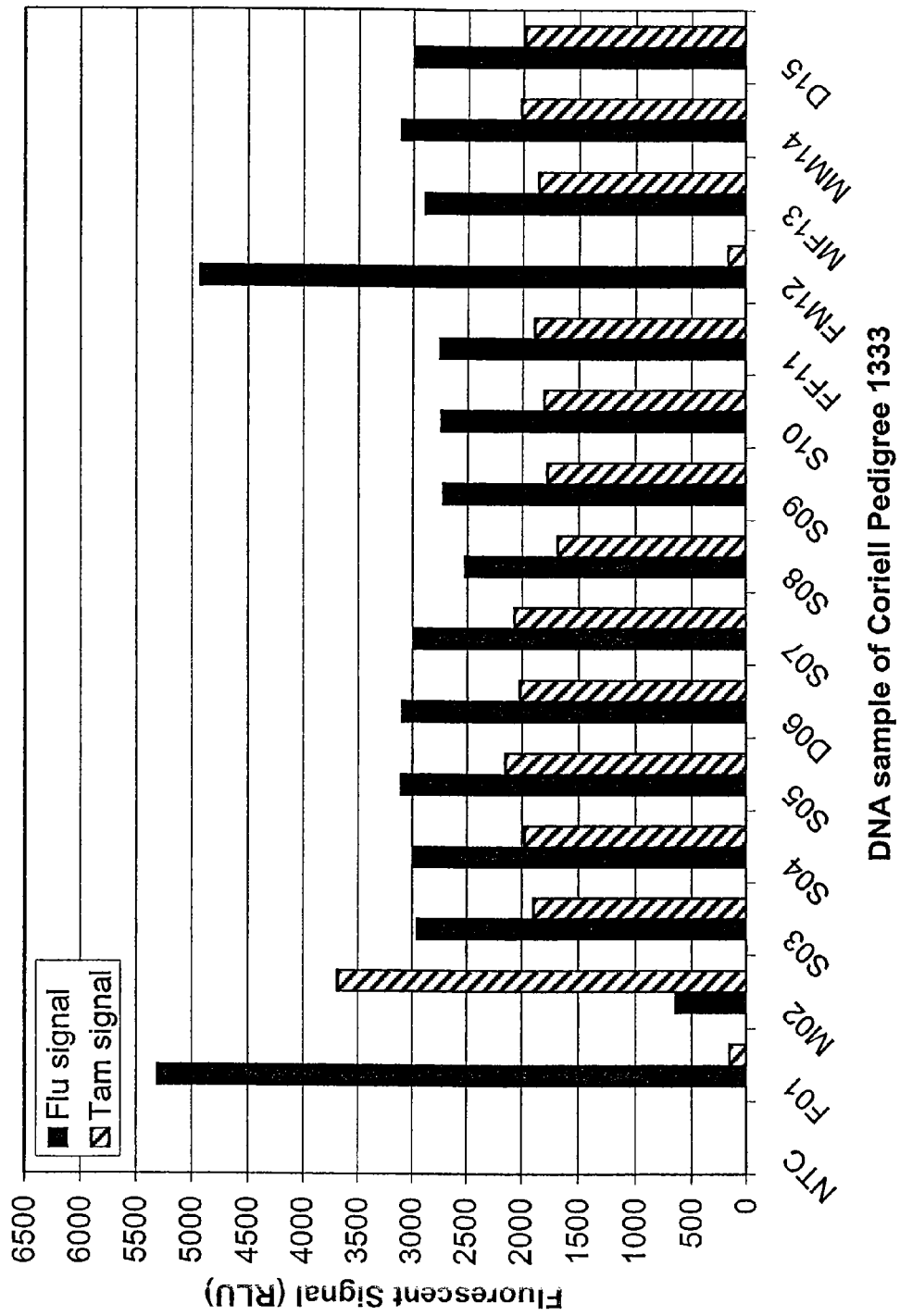

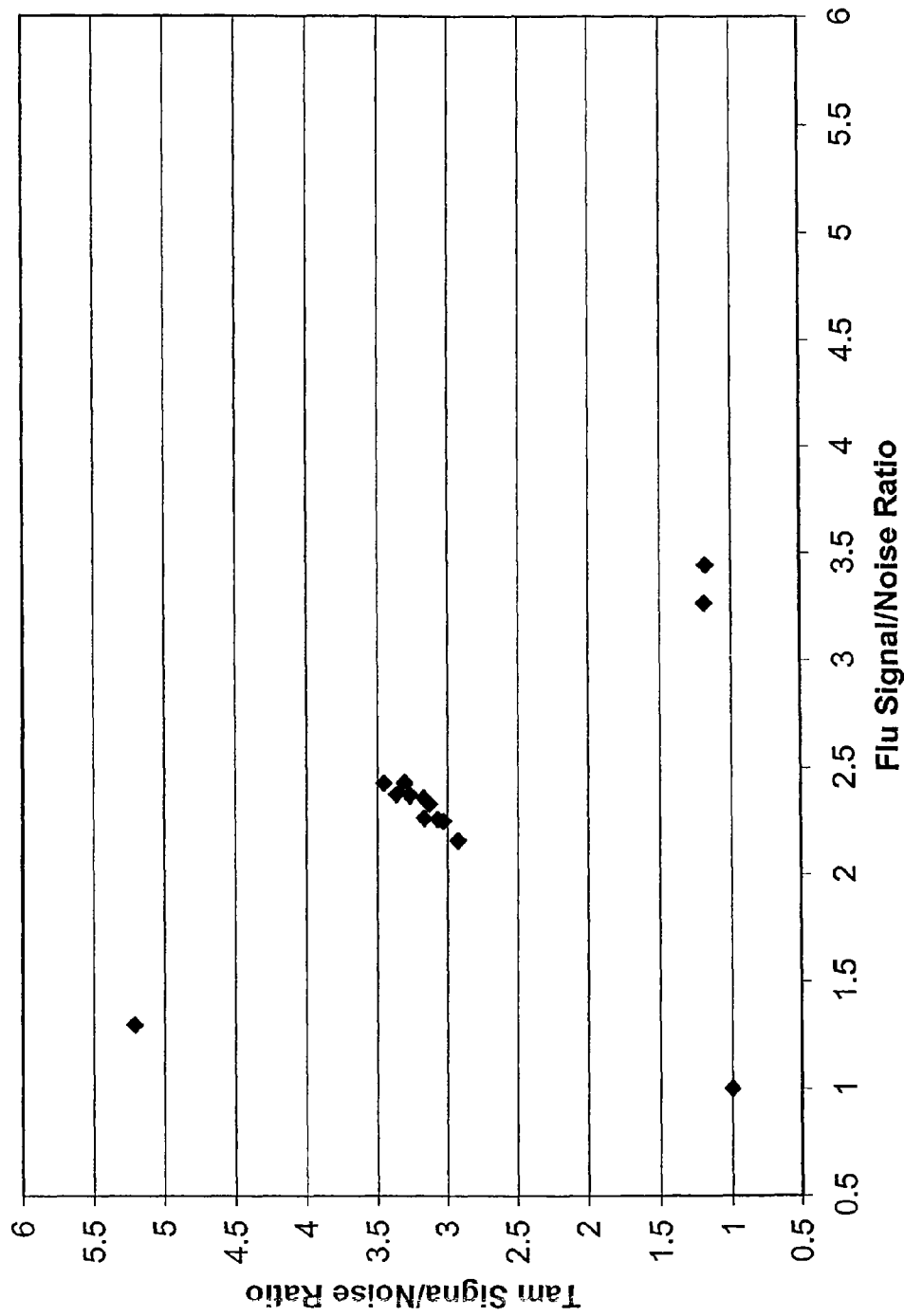
Figure 23. Allele distribution plot of SNP 6885 and Coriell Pedigree 1333.

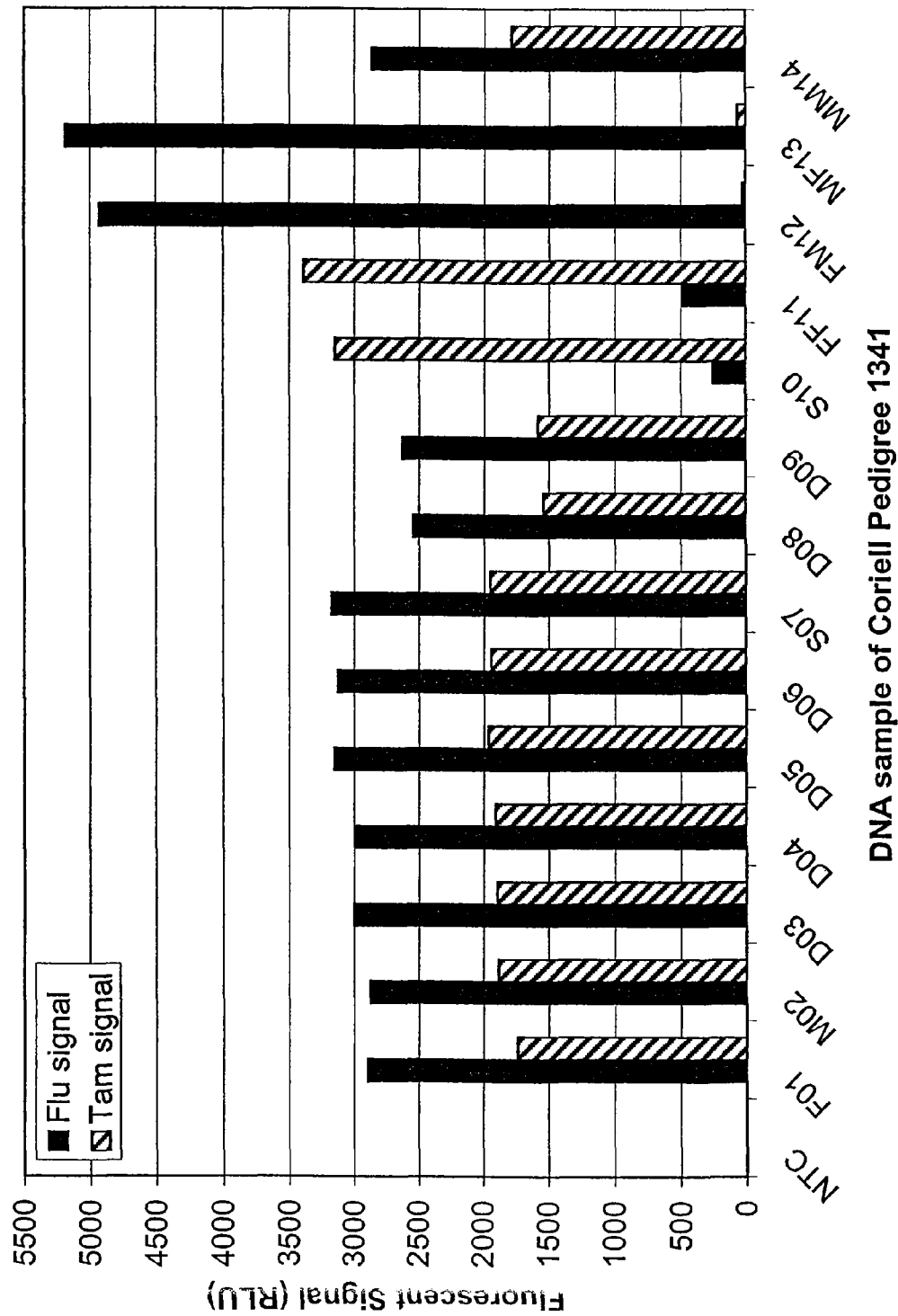
Figure 24. Bar graph of SNP 6885 and Coriell Pedigree 1341.

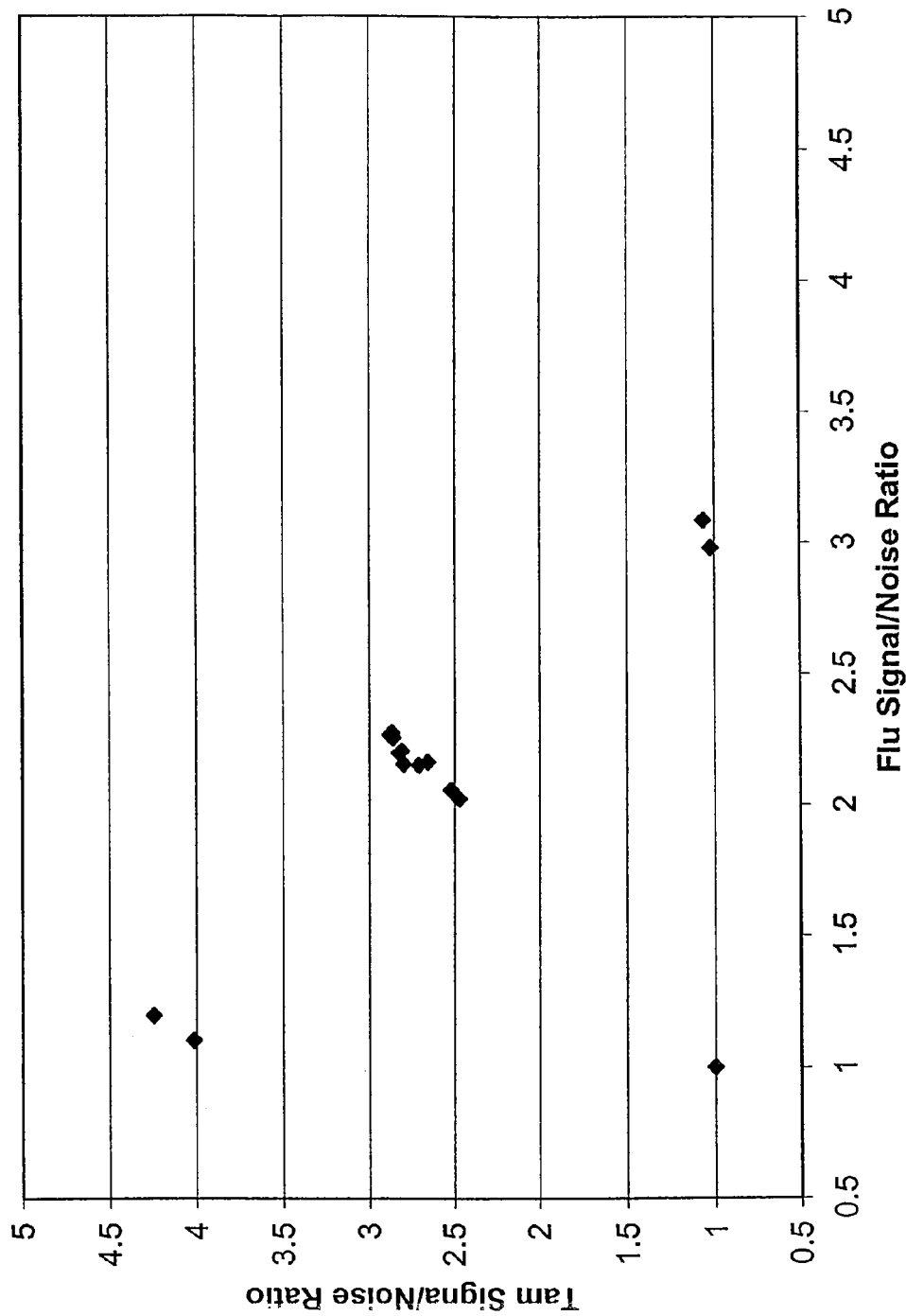

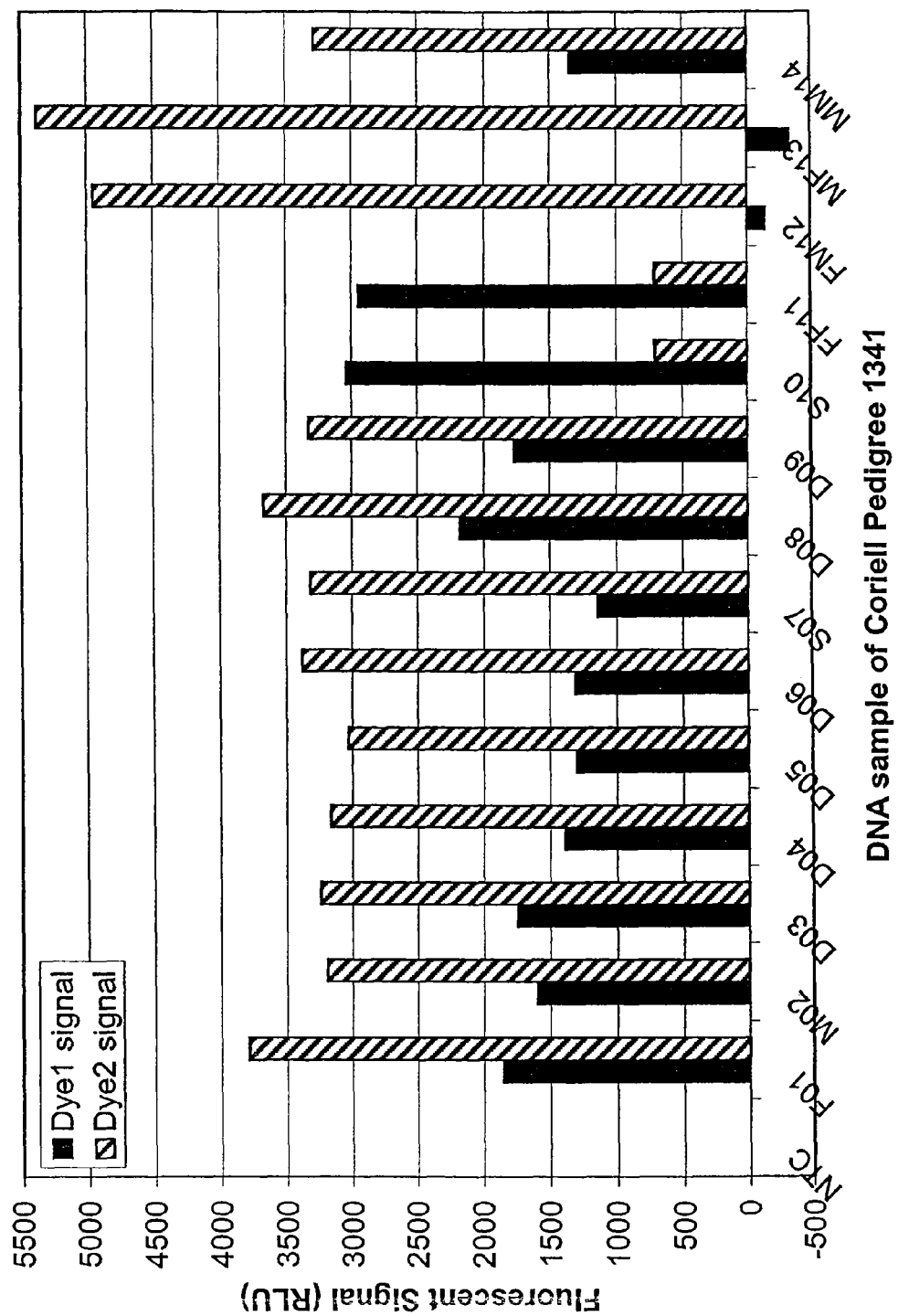
Figure 26. Bar graph of SNP 6885 and Coriell Pedigree 1341.

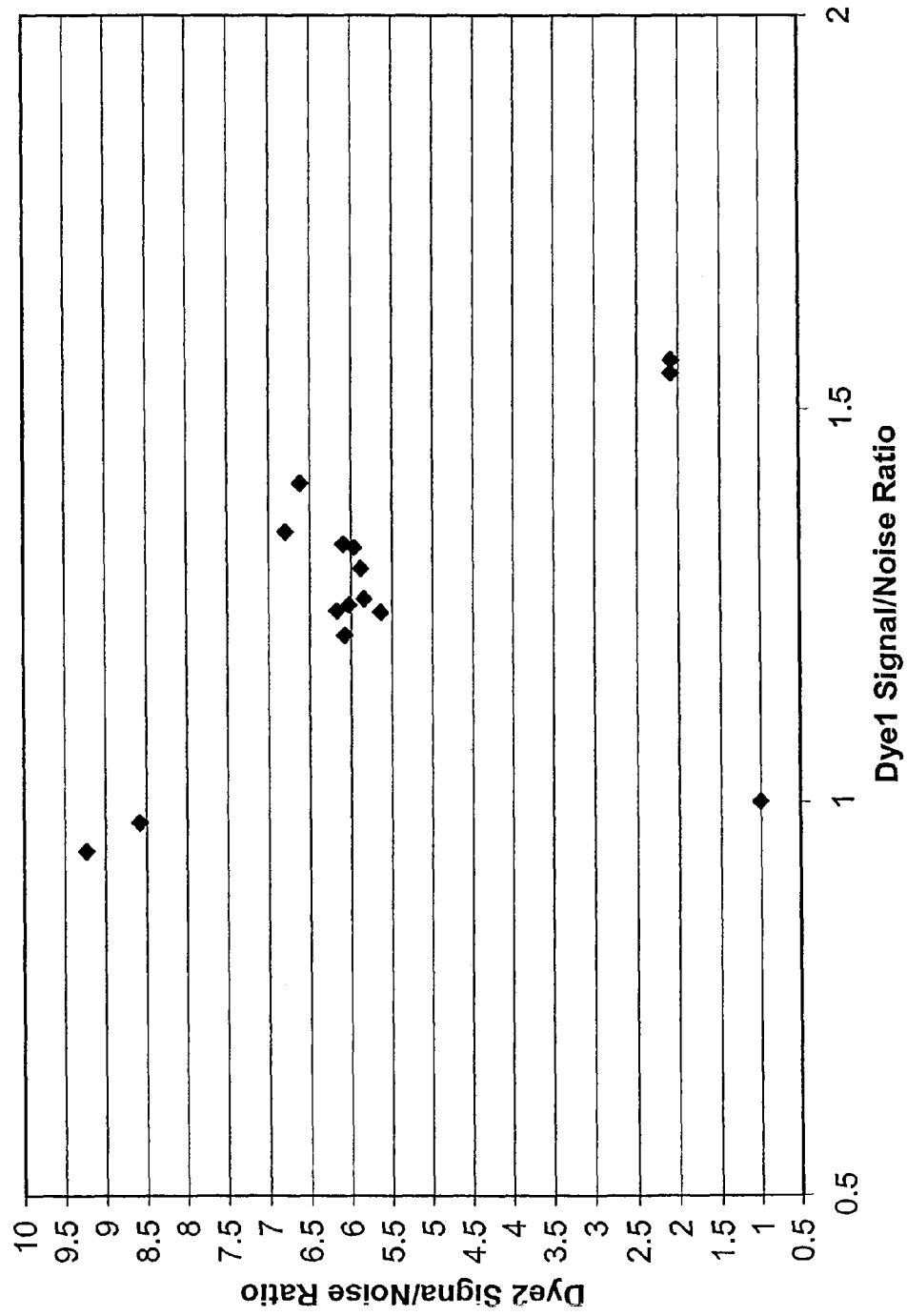
Figure 27. Allele distribution plot of SNP 6885 and Coriell Pedigree 1341.

Figure 32
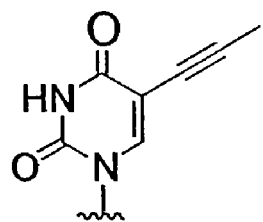
5-propynyl-U
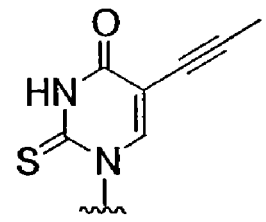
2-thio-5-propynyl-U
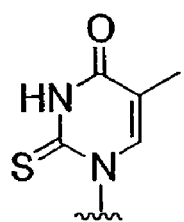
2-thio-T
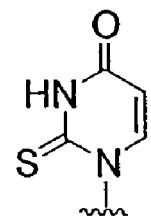
2-thio-U
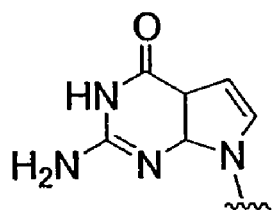
N9-(7-deaza-G)
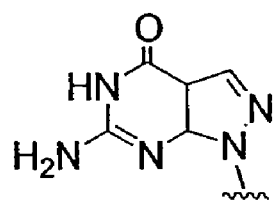
N9-(7-deaza-8-aza-G)
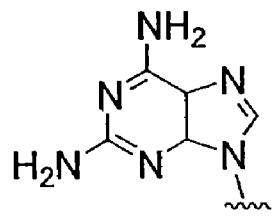
N9-(2,6,-diaminopurine)
N8-(7-deaza-8-aza-A)

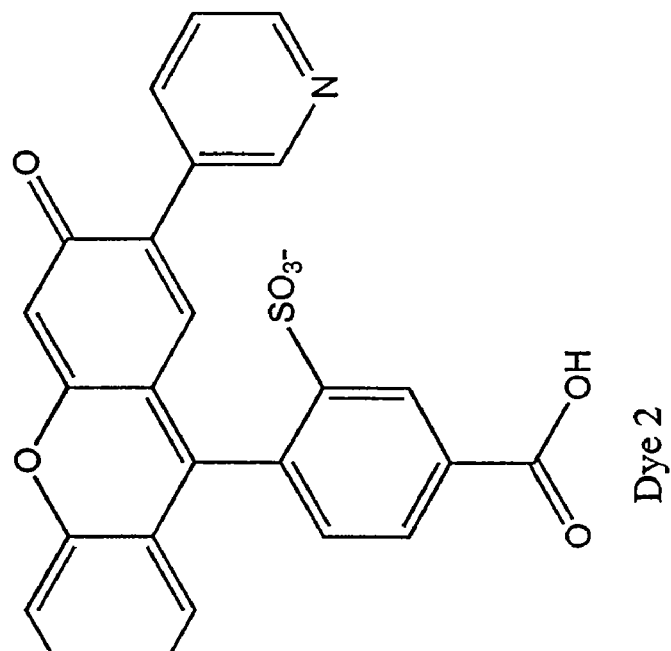
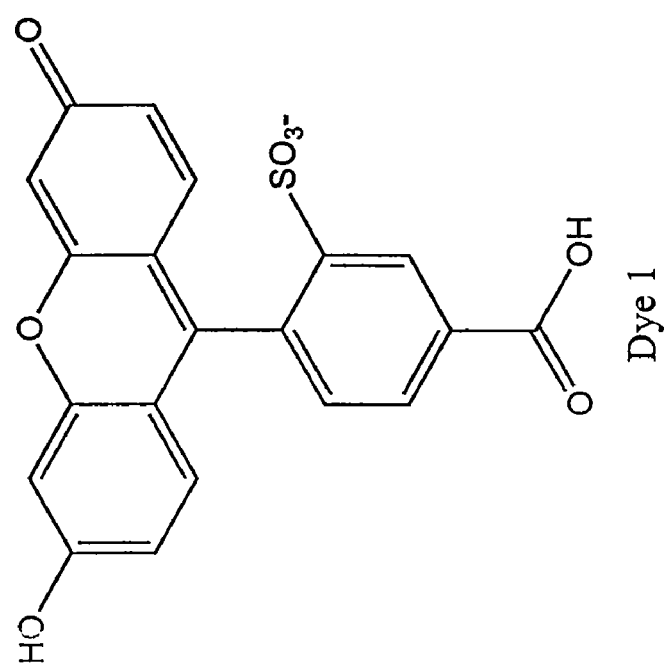
Figure 33

METHODS, KITS AND COMPOSITIONS PERTAINING TO COMBINATION OLIGOMERS AND LIBRARIES FOR THEIR PREPARATION

CROSS REFERENCE TO RELATED APPLICATIONS

This application is a divisional of U.S. patent application Ser. No. 10/096,125, filed Mar. 9, 2002 (now U.S. Pat. No. 7,256,275) incorporated herein by reference, which application claims the benefit of U.S. Provisional Patent Application Ser. No. 60/274,547 filed on Mar. 9, 2001, incorporated herein by reference.

BACKGROUND OF THE INVENTION

1. Field of the Invention

This invention pertains to the field of combination oligomers, including the block synthesis of combination oligomers in the absence of a template, as well as methods, kits, libraries and other compositions.

2. Introduction

Nucleic acid hybridization is a fundamental process in molecular biology. Probe-based assays are useful in the detection, quantitation and/or analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, nucleic acid probe-based assays have been slow to achieve commercial success. This lack of commercial success is, at least partially, the result of difficulties associated with specificity, sensitivity and/or reliability.

Nucleic acid amplification assays comprise an important class of specific target sequence detection methods in modern biology, with diverse applications in diagnosis of inherited disease, human identification, identification of microorganisms, paternity testing, virology, and DNA sequencing. The polymerase chain reaction (PCR) amplification method allows for the production and detection of target nucleic acid sequences with great sensitivity and specificity. PCR methods are integral to cloning, analysis of genetic expression, DNA sequencing, genetic mapping, drug discovery, and the like (Gilliland, *Proc. Natl. Acad. Sci.,* 87: 2725-2729 (1990); Bevan, *PCR Methods and Applications* 1: 222-228 (1992); Green, *PCR Methods and Applications,* 1: 77-90 (1991); McPherson, M. J., Quirke, P., and Taylor, G. R. in *PCR 2: A Practical Approach* Oxford University Press, Oxford (1995)). Methods for detecting a PCR product (amplicon) using an oligonucleotide probe capable of hybridizing with the target sequence or amplicon are described in Mullis, U.S. Pat. Nos. 4,683,195 and 4,683,202; EP No. 237,362.

Despite its name, Peptide Nucleic Acid (PNA) is neither a peptide, a nucleic acid nor is it an acid. Peptide Nucleic Acid (PNA) is a non-naturally occurring polyamide (pseudopeptide) that can hybridize to nucleic acid (DNA and RNA) with sequence specificity (See: U.S. Pat. No. 5,539,082 and Egholm et al., *Nature* 365: 566-568 (1993)). PNA has been characterized in the scientific literature as a nucleic acid mimic, rather than a nucleic acid analog, since its structure is completely synthetic and not derived from nucleic acid (See: Nielsen, P. E., *Acc. Chem. Res.* 32: 624-630 (1999)).

Being a non-naturally occurring molecule, unmodified PNA is not known to be a substrate for the enzymes that are known to degrade peptides or nucleic acids. Therefore, PNA should be stable in biological samples, as well as have a long shelf-life. Unlike nucleic acid hybridization, which is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., *Nature, at p.* 567). Because of their unique properties, it is clear that PNA is not the equivalent of a nucleic acid in either structure or function.

In addition to the limitations of selectivity/discrimination, there is a need to be able to rapidly and efficiently prepare numerous oligomers that can be used as probes or primers in an assay at a defined scale that is small enough to be cost effective. This need has arisen because genome sequencing has provided massive amounts of raw sequence data that can be mined for useful information. Because the volume of information is so massive, screening results that are generated from the mining operations typically involve high throughput analysis that requires tens or even hundreds of thousands of probes and primers. However, commercially available instruments that build nucleic acid and peptide nucleic acids based upon stepwise monomer assembly (de novo synthesis) require hours to produce single probes in a scale that is cost prohibitive for the manufacture of thousands or tens of thousands of probes or primers. Moreover, because the probes are synthesized de novo, it is difficult to expedite the delivery of the tens to hundreds of thousands of probes or primers within a short period, for example six months or less, without a massive investment in capital equipment. Therefore, it would be advantageous to be able to have a method for the rapid (days or weeks), efficient and cost effective production of tens or even hundreds of thousands of oligomers of desired nucleobase sequence that could be used as probes or primers for high throughput applications such as for expression analysis or the mining of genomes.

SUMMARY OF THE INVENTION

This invention pertains to the field of combination oligomers, including the block synthesis of combination oligomers in the absence of a template, as well as related methods, kits, libraries and other compositions. As used herein a combination oligomer is a composition comprising two or more oligomer blocks independently selected from peptide nucleic acid, PNA chimera and PNA combination oligomer, whether or not labeled, wherein said oligomer blocks are linked by a linker. This linker can optionally be a cleavage site for an enzyme. The aforementioned composition is referred to herein as a combination oligomer, without regard to its method of production, because its hybridization properties result from the combined properties of the two component oligomer blocks as well as the nature of the linker and the opportunity for interaction between the blocks when the combination oligomer hybridizes to a target sequence.

In one embodiment, this invention pertains to novel combination oligomers. The novel combination oligomers of this invention are referred to herein as self-indicating combination oligomers and substrate combination oligomers; each of which is described in more detail below (See also: Examples 4 & 5, below). It is to be understood that combination oligomers can be used as probes or primers in numerous applications. The requirement for probes is merely that they hybridize to a target sequence with sequence specificity. Thus, when used as a probe, there are no additional limitations on specific features of the combination oligomer. However, when used as a primer, it is a requirement that the combination oligomer contain moieties suitable for the recognition and operation of an enzyme since polymerase enzymes are not known to operate on unmodified PNA oligomers (See: Lutz et al., *J. Am. Chem. Soc.* 119: 3177-3178 (1997)).

In another embodiment, this invention pertains to a composition comprising a polynucleobase strand and a combination oligomer sequence specifically hybridized to a target sequence of contiguous nucleobases within the polynucleobase strand to thereby form a double stranded target sequence/combination oligomer complex (See FIG. 1; Also note that this configuration is sometimes referred to herein as being hybridized juxtaposed to the target sequence such that there is no gap or gap base). The combination oligomer comprises a first and a second oligomer block that are each independently a peptide nucleic acid, PNA chimera or PNA combination oligomer. The first and second oligomer blocks are covalently linked by a linker of at least three atoms in length.

In yet another embodiment, this invention pertains to a method for determining a target sequence of contiguous nucleobases. The method comprises contacting the target sequence with a combination oligomer, under suitable hybridization conditions, wherein the combination oligomer comprises a first oligomer block and a second oligomer block that are each independently a peptide nucleic acid, PNA chimera or PNA combination oligomer. The first and second oligomer blocks are linked covalently to each other by a linker that is at least three atoms in length. Moreover, the first and second oligomer blocks can sequence specifically hybridize to the target sequence of contiguous nucleobases to thereby form a double stranded target sequence/combination oligomer complex. Complex formation is determined to thereby determine the target sequence since the complex does not form in the absence of the target sequence. Determination of the complex includes, but is not limited to, determining the presence, absence, quantity (amount) or position of the complex to thereby determine the presence, absence, quantity (amount), position or identity of the target sequence (See for example: Examples 3-5).

In still another embodiment, this invention pertains to a method for determining the zygosity of a nucleic acid for a single nucleotide polymorphism (SNP). The method comprises contacting a nucleic acid sample with at least two independently detectable combination oligomers. Each independently detectable combination oligomer comprises a first oligomer block and a second oligomer block that are each independently a peptide nucleic acid, PNA chimera or PNA combination oligomer and the oligomer blocks are linked covalently to each other by a linker that is at least three atoms in length. The first and second oligomer blocks taken together encode a probing nucleobase sequence that is designed to sequence specifically hybridize to a target sequence of contiguous nucleobases in a polynucleobase strand of the nucleic acid sample, if present, to thereby form a double stranded target sequence/independently detectable combination oligomer complex. The probing nucleobase sequence in each independently detectable combination oligomer differs from the other by at least one nucleobase (the SNP nucleobase). However, the probing nucleobase sequence may differ by more than one nucleobase, depending on probe design, provided however that they differ by a single nucleobase at the SNP to be determined (See for example: Example 5, Table 9 and particularly the sets of PNA combination oligomer probes for SNPs 6876 and 6879).

According to the method, the nucleic acid sample and combination oligomers are contacted with one or more reagents suitable for performing a nucleic acid amplification reaction that amplifies the nucleic acid present in the sample and nucleic acid amplification is performed in the presence of the nucleic acid, the combination oligomers and the reagents. Complex formation for each independently detectable combination oligomer/target sequence complex is determined to thereby determine whether the nucleic acid is heterozygous or homozygous for a particular SNP. Complex determination can be correlated with the zygosity state of a particular SNP, since the complexes will not form in the absence of the respective target sequence of contiguous nucleobases for each particular combination oligomer. Moreover, the two independently detectable combination oligomers provide all of the information needed to determine the three possible genotype states depending on which complexes do and do not form.

In one embodiment, the independently detectable combination oligomers are independently detectable, self-indicating combination oligomers. According to the method a determination, under suitable hybridization conditions, is made of any change in detectable signal arising from at least one of the labels of each of the independently detectable energy transfer sets as a measure of whether or not each of the combination oligomers is hybridized to their respective target sequence of contiguous nucleobases. Such determination can be performed either during the process of the nucleic acid amplification (e.g. in real-time) or after the nucleic acid amplification reaction is completed (e.g. at the end-point). According to the method, the result of the change in signal for at least one label of each energy transfer set of each combination oligomer is correlated with a determination of the formation of each of the two possible target sequence/independently detectable self-indicating combination oligomer complexes. Based upon this data, one of the three possible states of zygosity of the sample for a particular SNP can be determined (See for example: Example 5).

In another embodiment, this invention is directed to a method for forming a combination oligomer from oligomer blocks. The method comprises reacting a first oligomer block, a second oligomer block, and optionally a condensation reagent or reagents under condensation conditions to thereby form a combination oligomer having a linker of at least three atoms in length that covalently links the first oligomer block to the second oligomer block. According to the method, the first and second oligomer blocks are each independently a peptide nucleic acid, PNA chimera or PNA combination oligomer. Neither of the first or second oligomer blocks is support bound and the combination oligomer forms in the absence of a template. The ligation/condensation reaction can be performed in aqueous solution. The nucleobases need not be protected during the condensation/ligation reaction.

In yet another embodiment, this invention pertains to another method for forming combination oligomers from oligomer blocks. The method comprises reacting a first oligomer block, a second oligomer block, and optionally a condensation reagent or reagents under condensation conditions to thereby form a combination oligomer having a linker of at least three atoms in length that covalently links the first oligomer block to the second oligomer block. The first and second oligomer blocks are each independently a peptide nucleic acid, PNA chimera or PNA combination oligomer. The nucleobases of the oligomer blocks do not comprise protecting groups and the combination oligomer forms in the absence of a template. The ligation/condensation can be performed in aqueous solution.

Regardless of the method of forming a combination oligomer as described above, in another embodiment, the product of the condensation/ligation reaction can optionally be further lengthened/elongated. Hence, the combination oligomer, as formed, can be used as an oligomer block such that repeating the method produces a further lengthened/elongated oligomer. According to the method, the combination oligomer, as previously formed, can optionally be deprotected, as may be required, to facilitate the next condensation/ligation step. The combination oligomer, as previously formed and optionally deprotected, is reacted with a third oligomer block and optionally a condensation reagent or reagents under condensation conditions. This forms the elongated combination oligomer having a covalent linkage of at least three atoms in length that covalently links the third oligomer block to the combination oligomer wherein, the elongated combination oligomer forms in the absence of a template. In accordance with this method, this process can be optionally repeated until the combination oligomer is of the desired length. Such a process of continued elongation can, for example, be useful for the preparation of arrays since longer oligomers are often used for this application.

In certain other embodiments of this invention, a combination oligomer is formed that possesses a cleavage site for an enzyme wherein the cleavage site is protected from cleavage upon the binding of the combination oligomer to a binding pair. Hence, this invention also pertains to a method for determining whether or not a combination oligomer binds to a possible binding partner (e.g. an aptmer or target sequence). The method comprises contacting the combination oligomer and the possible binding partner under suitable binding conditions to thereby possibly form a combination oligomer/binding partner complex. According to the method the combination oligomer is a polymer comprising a segment of the formula: A-W-C, wherein A and C are oligomer blocks that are optionally linked to other moieties and that are each independently a peptide nucleic acid, PNA chimera or PNA combination oligomer. The group W is a linker of at least three atoms in length that covalently links oligomer block A to oligomer block C and that is a cleavage site for an enzyme.

According to the method the binding partner and the combination oligomer are treated with an enzyme suitable for cleaving the cleavage site under suitable enzyme cleaving conditions. Then a determination is made of whether or not the combination oligomer has been cleaved by the activity of the enzyme to thereby determine whether or not the combination oligomer/binding partner complex formed.

Where the binding partner is a target sequence, and the combination oligomer is bound to the target sequence, it is protected from the activity of the enzyme. Accordingly, if the assay determines that the combination oligomer is not substantially degraded, it must have bound to the target sequence (See: Example 4). Conversely, where the combination oligomer was not protected from degradation, it can be concluded that the target sequence was not present. It is also to be understood that since such an assay relies upon an enzymatic event, quantitation of the target sequence can be determined by determining enzyme activity.

In still another embodiment, this invention pertains to kits. In one embodiment said kit comprises two or more independently detectable combination oligomers wherein each of said independently detectable combination oligomers comprises a first oligomer block and a second oligomer block that are each independently a peptide nucleic acid, a PNA chimera or PNA combination oligomer. The oligomer blocks are linked covalently to each other by a linker that is at least three atoms in length. In each independently detectable combination oligomer, the first and second oligomer blocks taken together encode a probing nucleobase sequence that is designed to sequence specifically hybridize to a target sequence of contiguous nucleobases that is suitable for the formation of a double stranded target sequence/combination oligomer complex. The probing nucleobase sequence in each independently detectable combination oligomer differs from the probing nucleobase sequences of the other independently detectable combination oligomer(s) by at least one nucleobase. Each independently detectable combination oligomer contains at least one independently detectable label. The kit optionally comprises; (i) one or more oligonucleotides; (ii) one or more buffers; (iii) one or more nucleotide triphosphates; (iv) a nucleic acid amplification master mix; or (v) one or more polymerase enzymes.

In yet another embodiment, this invention pertains to a set of two or more independently detectable combination oligomers. The combination oligomers of the set each comprise a first oligomer block and a second oligomer block that are each independently a peptide nucleic acid, PNA chimera or PNA combination oligomer. The oligomer blocks are linked covalently to each other by a linker that is at least three atoms in length. In each independently detectable combination oligomer, the first and second oligomer blocks taken together encode a probing nucleobase sequence that is designed to sequence specifically hybridize to a target sequence of contiguous nucleobases to thereby form a double stranded target sequence/combination oligomer complex. The probing nucleobase sequence in each independently detectable combination oligomer differs from the probing nucleobase sequences of the other independently detectable combination oligomer(s) of the set by at least one nucleobase. Each independently detectable combination oligomer contains at least one independently detectable label.

This invention is also directed to a method for forming a terminal oligomer block and a condensing oligomer block from a bifunctional single set library. The method comprises providing a bifunctional single set library of at least two oligomer blocks. One oligomer block of the bifunctional single set library is treated to thereby remove one or more of the protecting groups to thereby produce a terminal oligomer. One oligomer block of the bifunctional single set library is also treated to remove one or more different protecting groups, as compared with those that produce the terminal oligomer block, to thereby produce a condensing oligomer block.

Thus, this invention is also directed to a compound library comprising a bifunctional single set of oligomer blocks. The oligomer blocks of the set can be used to produce both terminal oligomer blocks and condensation oligomer blocks by the removal of certain protecting groups. The oligomer blocks of the bifunctional set are peptide nucleic acid oligomer, PNA chimera or PNA combination oligomer. The oligomer blocks of the bifunctional set are selected to comprise functional moieties that form a linker of at least three atoms in length when a terminal oligomer block is condensed with a condensation oligomer block. Furthermore, the oligomer blocks are not support bound and do not comprise nucleobase protecting groups.

In still another embodiment, this invention pertains to another compound library. According the invention, this compound library comprises at least one set of terminal oligomer blocks and at least one set of condensing oligomer blocks wherein each set of blocks comprises two or more different oligomers and said oligomer blocks are selected from the group consisting of: peptide nucleic acid oligomer, PNA chimera and PNA combination oligomer. The oligomer blocks are selected to comprise functional moieties that form a linker of at least three atoms in length when a terminal oligomer block is condensed with a condensation oligomer block. Additionally, the oligomer blocks are not support bound and the oligomer blocks do not comprise nucleobase-protecting groups. It is to be understood that a compound library of this invention is not to be limited to one or two sets of block oligomers. By way of a non-limiting example, the library may comprise three or more sets of oligomer blocks.

Accordingly, in still another embodiment, this invention pertains to another compound library. The compound library comprises at least one set of terminal oligomer blocks and at least two sets of condensing oligomer blocks. According to the invention, each set of oligomer blocks comprises two or more different oligomers and the oligomer blocks of each set are independently either peptide nucleic acid oligomer, PNA chimera or PNA combination oligomer. The oligomer blocks are selected to comprise functional moieties that form a linker of at least three atoms in length that covalently links the oligomer blocks when a terminal oligomer block is condensed with a condensation oligomer block. Additionally, the oligomer blocks are not support bound and the oligomer blocks do not comprise nucleobase-protecting groups. Furthermore, all of the oligomer blocks of a set of condensing oligomer blocks contain the same independently detectable reporter moiety and all of the oligomer blocks of the at least one set of terminal oligomer blocks comprise the same quencher moiety.

In still another embodiment, this invention pertains to novel combination oligomers such as a self-indicating combination oligomer. Accordingly, this invention also pertains to a composition of covalently linked oligomer blocks comprising a segment of the formula: A-B-C. According to the invention, oligomer blocks A and C are each independently a peptide nucleic acid, PNA chimera or PNA combination oligomer and are optionally linked to other moieties of the segment. The linker B is at least three atoms in length and covalently links oligomer block A to oligomer block C. Moreover, oligomer blocks A and C taken together encode a probing nucleobase sequence that is designed to sequence specifically hybridize to a target sequence of contiguous nucleobases to thereby form a double stranded target sequence/combination oligomer complex.

The self-indicating combination oligomer further comprises an energy transfer set of labels such that at least one acceptor moiety of the energy transfer set is linked to one of the linked oligomer blocks of the composition whilst at least one donor moiety of the energy transfer set is linked to another of the linked oligomer blocks of the composition wherein labels of the set are linked to the combination oligomer at positions that facilitate a change in detectable signal of at least one label when the combination oligomer is sequence specifically hybridized to a target sequence as compared to when the combination oligomer is in a non-hybridized state.

In yet another embodiment, this invention pertains to an array of at least two combination oligomers wherein at least one of the combination oligomers comprises a segment having the formula: A-B-C. According to the invention, oligomer blocks A and C are each independently a peptide nucleic acid, PNA chimera or PNA combination oligomer and are optionally linked to other moieties. The linker B is at least three atoms in length and covalently links oligomer block A to oligomer block C. Oligomer blocks A and C taken together encode a probing nucleobase sequence that is designed to sequence specifically hybridize to a target sequence of contiguous nucleobases to thereby form a double stranded target sequence/combination oligomer complex.

In yet another embodiment, this invention pertains to methods for forming an array of combination oligomers. In one embodiment, the method comprises reacting, at a site on a solid carrier, a first oligomer block, a second oligomer block, and optionally a condensation reagent or reagents under condensation conditions to thereby form a combination oligomer having a linker of at least three atoms in length that covalently links the first oligomer block to the second oligomer block. According to the invention, one of said two oligomer blocks is support bound. Further, the first and second oligomer blocks are each independently a peptide nucleic acid oligomer, PNA chimera or PNA combination oligomer. Additionally, one or both oligomer blocks do not comprise nucleobase protecting groups and the combination oligomer forms in the absence of a template. The method further comprises repeating the method with one or more different oligomer blocks at one or more different sites until the desired array of combination oligomers is constructed.

In still another embodiment, this invention pertains to another method for forming an array of combination oligomers. The method comprises reacting, at a site on a solid carrier, a functional group of a combination oligomer having a linker of at least three atoms in length that covalently links the first oligomer block to the second oligomer block with a surface functional group to thereby covalently attach the combination oligomer to the surface. According to the method, the first and second oligomer blocks of the combination oligomer are each independently a peptide nucleic acid oligomer, PNA chimera or PNA combination oligomer. Moreover, one or both oligomer blocks do not comprise nucleobase-protecting groups. The method further comprises repeating the method for attachment of the combination oligomer with one or more different combination oligomers at one or more different sites until the desired array of combination oligomers is constructed.

BRIEF DESCRIPTION OF THE DRAWINGS

The skilled artisan will understand that the drawings, described below, are for illustration purposes only. The drawings are not intended to limit the scope of the present teachings in any way.

FIG. 1 is an illustration of hybrids formed from a combination oligomer and a target sequence, as described in Example 1, that either do or do not comprise a "gap" or "base gap" (that is to say that the oligomer blocks of the combination oligomer do or do not hybridize to a target sequence of contiguous nucleobases).

FIG. 4 is a bar graph of data obtained for SNP 6784 and Coriell Pedigree 1333.

FIG. 5 is an allele distribution plot for data obtained for SNP 6784 and Coriell Pedigree 1333.

FIG. 6 is a bar graph of data obtained for SNP 6802 and Coriell Pedigree 1333.

FIG. 7 is an allele distribution plot for data obtained for SNP 6802 and Coriell Pedigree 1333.

FIG. 8 is a bar graph of data obtained for SNP 6806 and Coriell Pedigree 1333.

FIG. 9 is an allele distribution plot for data obtained for SNP 6806 and Coriell Pedigree 1333.

FIG. 10 is a bar graph of data obtained for SNP 6834 and Coriell Pedigree 1331.

FIG. 11 is an allele distribution plot for data obtained for SNP 6834 and Coriell Pedigree 1331.

FIG. 12 is a bar graph of data obtained for SNP 6837 and Coriell Pedigree 1341.

FIG. 13 is an allele distribution plot for data obtained for SNP 6837 and Coriell Pedigree 1341.

FIG. 14 is a bar graph of data obtained for SNP 6848 and Coriell Pedigree 1331.

FIG. 15 is an allele distribution plot for data obtained for SNP 6848 and Coriell Pedigree 1331.

FIG. 16 is a bar graph of data obtained for SNP 6876 and Coriell Pedigree 1333.

FIG. 17 is an allele distribution plot for data obtained for SNP 6876 and Coriell Pedigree 1333.

FIG. 18 is a bar graph of data obtained for SNP 6876 and Coriell Pedigree 1341.

FIG. 19 is an allele distribution plot for data obtained for SNP 6876 and Coriell Pedigree 1341.

FIG. 20 is a bar graph of data obtained for SNP 6879 and Coriell Pedigree 1331.

FIG. 21 is an allele distribution plot for data obtained for SNP 6879 and Coriell Pedigree 1331.

FIG. 22 is a bar graph of data obtained for SNP 6885 and Coriell Pedigree 1333.

FIG. 23 is an allele distribution plot for data obtained for SNP 6885 and Coriell Pedigree 1333.

FIG. 24 is a bar graph of data obtained for SNP 6885 and Coriell Pedigree 1341.

FIG. 25 is an allele distribution plot for data obtained for SNP 6885 and Coriell Pedigree 1341.

FIG. 26 is a bar graph of data obtained for SNP 6885 and Coriell Pedigree 1341 using two ligated combination oligomers.

FIG. 27 is an allele distribution plot for data obtained for SNP 6885 and Coriell Pedigree 1341 using two ligated combination oligomers.

FIG. 32 contains illustrations non-naturally occurring nucleobases that can be used in the oligomer blocks or combination oligomers of this invention to produce non-standard base pairing motifs.

FIG. 33 contains an illustration of both Dye 1 and Dye 2.

DETAILED DESCRIPTION OF THE INVENTION

1. Definitions

Figure 2:
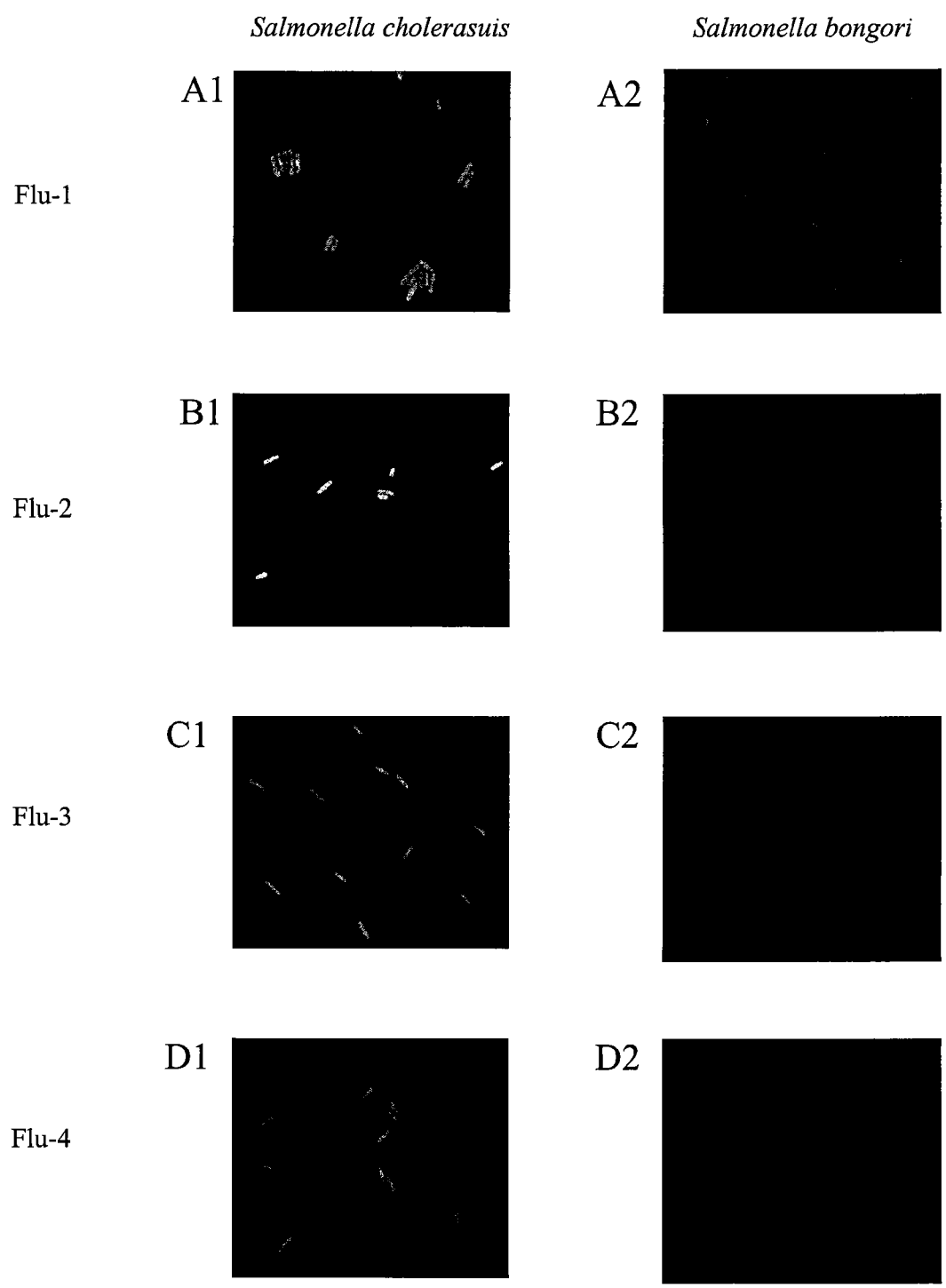
FIG. 2 is a color reproduction of digital images taken with a CCD camera equipped microscope for PNA-FISH analysis of *Salmonella* bacteria, as described in Example 3.

For the purposes of interpreting this specification the following definitions shall apply and whenever appropriate, terms used in the singular shall also include the plural and vice versa.

a. As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

b. As used herein, "nucleobase sequence" means any segment, or aggregate of two or more segments (e.g. the aggregate nucleobase sequence of two or more oligomer blocks), of a polymer that comprises nucleobase-containing subunits. Non-limiting examples of suitable polymers or polymers segments include oligodeoxynucleotides (e.g. DNA), oligoribonucleotides (e.g. RNA), peptide nucleic acids (PNA), PNA chimeras, PNA combination oligomers, nucleic acid analogs and/or nucleic acid mimics.

c. As used herein, "target sequence" is a nucleobase sequence of a polynucleobase strand sought to be determined. It is to be understood that the nature of the target sequence is not a limitation of this invention. The polynucleobase strand comprising the target sequence may be provided from any source. For example, the target sequence may exist as part of a nucleic acid (e.g. DNA or RNA), PNA, nucleic acid analog or other nucleic acid mimic. The sample containing the target sequence may be provided from nature or it may be synthesized or supplied from a manufacturing process. When the target sequence is a subsequence of a nucleic acid, said nucleic acid can be obtained from any source. For example, said nucleic acid can be produced from a nucleic acid amplification process, contained in a cell or organism or otherwise be extracted from a cell or organism. Non-limiting examples of nucleic acid amplification processes that can be the source for the nucleic acid include, but are not limited to, Polymerase Chain Reaction (PCR), Ligase Chain Reaction (LCR), Strand Displacement Amplification (SDA), Transcription-Mediated Amplification (TMA), Q-beta replicase amplification (Q-beta) and Rolling Circle Amplification (RCA).

d. As used herein, "polynucleobase strand" means a complete single polymer strand comprising nucleobase subunits. For example, a single nucleic acid strand of a double stranded nucleic acid is a polynucleobase strand.

e. As used herein, "nucleic acid" is a nucleobase sequence-containing polymer, or polymer segment, having a backbone formed from nucleotides, or analogs thereof. Preferred nucleic acids are DNA and RNA. For the avoidance of any doubt, PNA is a nucleic acid mimic and not a nucleic acid analog.

f. As used herein, "peptide nucleic acid" or "PNA" means any oligomer or polymer segment (e.g. oligomer block) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference. The term "peptide nucleic acid" or "PNA" shall also apply to any oligomer or polymer segment comprising two or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry*

*Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:555-560 (1997); Howarth et al., *J. Org. Chem.* 62: 5441-5450 (1997); Altmann, K-H et al., *Bioorganic & Medicinal Chemistry Letters*, 7: 1119-1122 (1997); Diederichsen, U., *Bioorganic & Med. Chem. Lett.*, 8: 165-168 (1998); Diederichsen et al., *Angew. Chem. Int. Ed.*, 37: 302-305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000. For the avoidance of doubt, the linking of one or more amino acid subunits, or one or more labels or linkers, to a PNA oligomer or segment (e.g. PNA oligomer block) does not produce a PNA chimera.

In certain embodiments, a "peptide nucleic acid" or "PNA" is an oligomer or polymer segment comprising two or more covalently linked subunits of the formula:

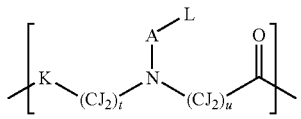

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; $—(CJ_2)_s$- and a group of the formula; $—(CJ_2)_s C(O)—$, wherein, J is defined above and each s is a whole number from one to five. Each t is 1 or 2 and each u is 1 or 2. Each L is the same or different and is independently selected from: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), other naturally occurring nucleobase analogs or other non-naturally occurring nucleobases.

In certain other embodiments, a PNA subunit consists of a naturally occurring or non-naturally occurring nucleobase attached to the N-α-glycine nitrogen of the N-[2-(aminoethyl)]glycine backbone through a methylene carbonyl linkage; this currently being the most commonly used form of a peptide nucleic acid subunit.

g. As used herein, "PNA chimera" means an oligomer or polymer segment comprising two or more PNA subunits and one or more nucleic acid subunits (i.e. DNA or RNA), or analogs thereof, that are selected from different classes of subunits and that are linked by a covalent bond but not a linker. For example, a PNA/DNA chimera would comprise at least two PNA subunits covalently linked, via a chemical bond, to at least one 2'-deoxyribonucleic acid subunit (For exemplary methods and compositions related to PNA/DNA chimera preparation See: WO96/40709). For purposes of this invention, a PNA chimera includes a combination of different types of nucleobases containing subunits (e.g. PNA, DNA, RNA) but the mere incorporation of amino acid subunits, such as glycine, or one or more labels or linkers, does not mean that an oligomer is PNA chimera.

h. As used herein, "block", "oligomer block" or "block oligomer" means a peptide nucleic acid, PNA chimera, or PNA combination oligomer that is designed and available to be ligated to a second appropriately modified oligomer to thereby prepare a combination oligomer or elongated combination oligomer, as appropriate. The oligomer blocks may be unlabeled, labeled with one or more reporter moieties and/or comprise one or more protected or unprotected functional groups.

i. As used herein "PNA combination oligomer" means a combination oligomer comprising at least one PNA oligomer block or PNA chimera oligomer block.

j. As used herein, "combination oligomer" means an oligomer comprising two or more oligomer blocks that are linked by a linker.

k. As used herein, "linker" means a moiety of at least three atoms in length that is not part a nucleobase containing backbone subunit of the polymer wherein said at least three atoms covalently link the nucleobase containing backbone subunits of two component oligomer blocks.

l. As used herein, "native oligomer" means a peptide nucleic acid, nucleic acid or PNA chimera that does not comprise a linker that separates two oligomer blocks. Thus, a native oligomer, even if a chimera, comprises a backbone wherein the backbone subunits are linked together either directly or though a bridging moiety of no more than two atoms in length.

m. As used herein, "gap" means a space, that is at least one nucleobase in length, between the terminal nucleobases of two oligomer blocks adjacently hybridized onto a target sequence (See for example: FIG. 1).

n. As used herein, the terms "label", "reporter moiety" or "detectable moiety" are interchangeable and refer to moieties that can be attached to an oligomer block or combination oligomer, or otherwise be used in a reporter system, to thereby render the oligomer detectable by an instrument or method. For example, a label can be any moiety that: (i) provides a detectable signal; (ii) interacts with a second label to modify the detectable signal provided by the first or second label; or (iii) confers a capture function, i.e. hydrophobic affinity, antibody/antigen, ionic complexation.

o. As used herein, "sequence specifically" means hybridization by base pairing through hydrogen bonding. Non-limiting examples of standard base pairing includes adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); and N8-(7-deaza-8-aza-adenine), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine) or N9-(7-deaza-8-aza-guanine) (See: Seela et al., *Nucl. Acids, Res.:* 28(17): 3224-3232 (2000)).

p. As used herein, "condensation conditions" means conditions suitable to condense/ligate two oligomer blocks in accordance with the condensation/ligation chemistry chosen.

q. As used herein "ligation" and "condensation" are interchangeable and, because strictly speaking not all of the methods suitable for linking the oligomer blocks are condensation reactions, refer to the process of covalently linking two oligomer blocks to thereby form a combination oligomer comprising a linker of at least three atoms in length. It is also to be understood that the ligation/condensation chemistry is not to be a limitation of these methods so long as it produces a linker between the oligomer blocks. Non-limiting examples of numerous ligation/condensation chemistries suitable for forming combination oligomers are described herein with reference to FIGS. 28b & 29b-32.

r. As used herein, "nucleobase protecting group" means a protecting group covalently linked to a functional group of a nucleobase to render the functional group unreactive during certain chemical reactions (e.g. ligation/condensation). For example, the exocylic amino groups of adenine, cytosine and guanine are typically protected with a suitable protecting group during de novo chemical oligomer synthesis. However, nucleobases need not be protected during the ligation/condensation reactions described herein. For the avoidance of doubt, formation of a salt of a functional group to render the group unreactive during a chemical reaction is not a nucleobase-protecting group, as used herein, since there is no covalent link.

s. As used herein, "quenching" means a decrease in fluorescence of a fluorescent reporter moiety caused by energy transfer associated with a quencher moiety, regardless of the mechanism.

t. As used herein "solid support" or "solid carrier" means any solid phase material upon which a combination oligomer is synthesized, attached, ligated or otherwise immobilized. Solid support encompasses terms such as "resin", "solid phase", "surface" and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

u. As used herein, "support bound" means immobilized on or to a solid support. It is understood that immobilization can occur by any means, including for example; by covalent attachment, by electrostatic immobilization, by attachment through a ligand/ligand interaction, by contact or by depositing on the surface.

v. "Array" or "microarray" means a predetermined spatial arrangement of oligomers present on a solid support or in an arrangement of vessels. Certain array formats are referred to as a "chip" or "biochip" (M. Schena, Ed. *Microarray Biochip Technology*, BioTechnique Books, Eaton Publishing, Natick, Mass. (2000). An array can comprise a low-density number of addressable locations, e.g. 2 to about 12, medium-density, e.g. about a hundred or more locations, or a high-density number, e.g. a thousand or more. Typically, the array format is a geometrically-regular shape that allows for fabrication, handling, placement, stacking, reagent introduction, detection, and storage. The array may be configured in a row and column format, with regular spacing between each location. Alternatively, the locations may be bundled, mixed, or homogeneously blended for equalized treatment or sampling. An array may comprise a plurality of addressable locations configured so that each location is spatially addressable for high-throughput handling, robotic delivery, masking, or sampling of reagents, or by detection means including scanning by laser illumination and confocal or deflective light gathering.

2. Description of the Invention

I. General

PNA Synthesis:
Methods for the chemical assembly of PNAs are well known (See: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference (Also see: PerSeptive Biosystems Product Literature)). As a general reference for PNA synthesis methodology also please see: Nielsen et al., *Peptide Nucleic Acids; Protocols and Applications*, Horizon Scientific Press, Norfolk England (1999).

Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer.

PNA may be synthesized at any scale, from submicromole to millimole, or more. Most conveniently, PNA is synthesized at the 2 μmole scale, using Fmoc/Bhoc, tBoc/Z, or MMT protecting group monomers on an Expedite Synthesizer (Applied Biosystems) on XAL or PAL support; or on the Model 433A Synthesizer (Applied Biosystems) with MBHA support; or on other automated synthesizers. Because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

When used in ligation reactions, the nature of the ligation chemistry chosen should be considered. For simplicity, we sometimes refer to one of the oligomer blocks used in a ligation reaction as a terminal block and the other as the condensation block. This distinction is generally irrelevant except to distinguish between the different blocks especially if they contain the same nucleobase sequence. Often at least the nature of the functional groups that are used in the ligation will be different for the terminal and condensation blocks since they can be designed to accommodate different ligation chemistries. However, when the oligomer is to be extended by multiple ligations, we will generally refer to the terminal oligomer block as the oligomer block produced from the first ligation or from the immediately preceding ligation step. Accordingly, depending on whether an oligomer block is a condensing oligomer block or terminal oligomer block may have an effect on the actual composition of the termini. Several non-limiting examples of ligation chemistries are illustrated in FIGS. 28-31a & 31b. Using no more than routine experimentation as well as the description contained herein, one of ordinary skill in the art will easily be able to prepare combination oligomers according to this invention.

The terminal blocks may comprise a C-terminal amide that is relatively unreactive. In contrast, the condensing blocks may comprise a C-terminal end that is suitable for the ligation reaction. However, depending upon the nature of the condensation chemistry, the C-terminal end of the oligomer may comprise a C-terminal acid or an alternative functional group (See For Example: FIGS. 28a-31b). If a functional group, the terminus may or may not require the addition of a protecting group depending on the nature of the condensation/ligation chemistry. Since the oligomer blocks are themselves often prepared by de novo methods and because suitable commercial reagents and instrumentation are available for the production of PNA oligomers comprising either of a C-terminal amino acid, an alternative functional group or a C-terminal amide, one of skill in the art can easily prepare the oligomer blocks of the desired C-terminal configuration.

With respect to the N-terminus, again the exact configuration can depend on the nature of the ligation chemistry chosen and on whether or not the oligomer is a condensing oligomer block or a terminal oligomer block. If the oligomer is a terminal oligomer block, the N-terminus may comprise a reactive functional group whereas if the oligomer is a condensing oligomer block, the N-terminus can be capped. Non-limiting examples of capping include labeling the N-terminus with a label or otherwise reacting it with a relatively non-reactive moiety such as acetyl. If the N-terminus is to be involved in the ligation reaction, it will typically exist as a free amine unless alternative condensation chemistry is employed (See For Example: FIGS. 28a-31b). Since the oligomer blocks are themselves prepared by de novo methods and because suitable commercial reagents and instrumentation are available for the production of PNA oligomers, one of skill in the art can easily prepare the oligomer blocks of the desired N-terminal configuration.

In addition to the modification of the termini for ligation, the oligomer blocks can be modified and/or properly protected to thereby incorporate functional groups for labeling or for attachment to surfaces. Such functional groups can be utilized either before or after ligation depending upon factors such as: 1) the oligomer synthesis chemistry (e.g. harsh deprotection conditions required that might destroy a label), the condensation/ligation chemistry chosen (e.g. functional groups of the desired label might interfere with the condensation chemistry) and the intended use of the functional group (e.g. whether it is intended for labeling or for attachment to a solid support).

PNA Labeling/Modification:

Non-limiting methods for labeling PNAs are described in U.S. Pat. No. 6,110,676, U.S. Pat. No. 6,280,964, WO99/22018, WO99/21881, WO99/37670 and WO99/49293, the examples section of this specification or are otherwise well known in the art of PNA synthesis and peptide synthesis. Methods for labeling PNA are also discussed in Nielsen et al., *Peptide Nucleic Acids; Protocols and Applications*, Horizon Scientific Press, Norfolk, England (1999). Non-limiting methods for labeling the PNA oligomers that can either be used as block oligomers or otherwise be used to prepare combination oligomers are as follows.

Because the synthetic chemistry of assembly is essentially the same, any method commonly used to label a peptide can often be adapted to effect the labeling a PNA oligomer. Generally, the N-terminus of the polymer can be labeled by reaction with a moiety having a carboxylic acid group or activated carboxylic acid group. One or more spacer moieties can optionally be introduced between the labeling moiety and the nucleobase containing subunits of the oligomer. Generally, the spacer moiety can be incorporated prior to performing the labeling reaction. If desired, the spacer may be embedded within the label and thereby be incorporated during the labeling reaction.

Typically the C-terminal end of the polymer can be labeled by first condensing a labeled moiety or functional group moiety with the support upon which the PNA oligomer is to be assembled. Next, the first nucleobase containing synthon of the PNA oligomer can be condensed with the labeled moiety or functional group moiety. Alternatively, one or more spacer moieties (e.g. 8-amino-3,6-dioxaoctanoic acid; the "O-linker") can be introduced between the label moiety or functional group moiety and the first nucleobase subunit of the oligomer. Once the molecule to be prepared is completely assembled, labeled and/or modified, it can be cleaved from the support deprotected and purified using standard methodologies.

For example, the labeled moiety or functional group moiety can be a lysine derivative wherein the ε-amino group is a protected or unprotected functional group or is otherwise modified with a reporter moiety. The reporter moiety could be a fluorophore such as 5(6)-carboxyfluorescein or a quencher moiety such as 4-((4-(dimethylamino)phenyl)azo)benzoic acid (dabcyl). Condensation of the lysine derivative with the synthesis support can be accomplished using standard condensation (peptide) chemistry. The α-amino group of the lysine derivative can then be deprotected and the nucleobase sequence assembly initiated by condensation of the first PNA synthon with the α-amino group of the lysine amino acid. As discussed above, a spacer moiety may optionally be inserted between the lysine amino acid and the first PNA synthon by condensing a suitable spacer (e.g. Fmoc-8-amino-3,6-dioxaoctanoic acid) with the lysine amino acid prior to condensation of the first PNA synthon.

Alternatively, a functional group on the assembled, or partially assembled, polymer can be introduced while the oligomer is still support bound. The functional group will then be available for any purpose, including being used to either attached the oligomer to a support or otherwise be reacted with a reporter moiety, including being reacted post-ligation (by post-ligation we mean at a point after the combination oligomer has been fully formed by the performing of one or more condensation/ligation reactions). This method, however, requires that an appropriately protected functional group be incorporated into the oligomer during assembly so that after assembly is completed, a reactive functional can be generated. Accordingly, the protected functional group can be attached to any position within the combination oligomer or block, including, at the block oligomer termini, at a position internal to the oligomer blocks, or linked at a position integral to the linker.

For example, the ε-amino group of a lysine could be protected with a 4-methyl-triphenylmethyl (Mtt), a 4-methoxytriphenylmethyl (MMT) or a 4,4'-dimethoxytriphenylmethyl (DMT) protecting group. The Mtt, MMT or DMT groups can be removed from the oligomer (assembled using commercially available Fmoc PNA monomers and polystyrene support having a PAL linker; PerSeptive Biosystems, Inc., Framingham, Mass.) by treatment of the synthesis resin under mildly acidic conditions. Consequently, a donor moiety, acceptor moiety or other reporter moiety, for example, can then be condensed with the ε-amino group of the lysine amino acid while the polymer is still support bound. After complete assembly and labeling, the polymer is then cleaved from the support, deprotected and purified using well-known methodologies.

By still another method, the reporter moiety is attached to the combination oligomer or oligomer block after it is fully assembled and cleaved from the support. This method is preferable where the label is incompatible with the cleavage, deprotection or purification regimes commonly used to manufacture the oligomer. By this method, the PNA oligomer will generally be labeled in solution by the reaction of a functional group on the polymer and a functional group on the label. Those of ordinary skill in the art will recognize that the composition of the coupling solution will depend on the nature of oligomer and label, such as for example a donor or acceptor moiety. The solution may comprise organic solvent, water or any combination thereof. Generally, the organic solvent will be a polar non-nucleophilic solvent. Non limiting examples of suitable organic solvents include acetonitrile (ACN), tetrahydrofuran, dioxane, methyl sulfoxide, N,N'-dimethylformamide (DMF) and N-methylpyrrolidone (NMP).

The functional group on the polymer to be labeled can be a nucleophile (e.g. an amino group) and the functional group on the label can be an electrophile (e.g. a carboxylic acid or activated carboxylic acid). It is however contemplated that this can be inverted such that the functional group on the polymer can be an electrophile (e.g. a carboxylic acid or activated carboxylic acid) and the functional group on the label can be a nucleophile (e.g. an amino acid group). Non-limiting examples of activated carboxylic acid functional groups include N-hydroxysuccinimidyl esters. In aqueous solutions, the carboxylic acid group of either of the PNA or label (depending on the nature of the components chosen) can be activated with a water soluble carbodiimide. The reagent, 1-ethyl-3-(3-dimethylamino-propyl)carbodiimide hydrochloride (EDC), is a commercially available reagent sold specifically for aqueous amide forming condensation reactions. Applicants have likewise observed that such condensation reactions can be improved when 1-Hydroxy-7-azabenzotriazole (HOAt) or 1-hydrozybenzotriazole (HOBt) is mixed with the EDC.

The pH of aqueous solutions can be modulated with a buffer during the condensation reaction. For example, the pH during the condensation can be in the range of 4-10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH can be modulated using biological buffers such as (N-[2-hydroxyethyl]piperazine-N'-[2-ethanesulfonic acid) (HEPES) or 4-morpholineethane-sulfonic acid (MES) or inorganic buffers such as sodium bicarbonate.

Chimera Synthesis and Labeling/Modification:

PNA chimeras are a combination of a nucleic acid and peptide nucleic acid subunits. Hence, the synthesis, labeling and modification of PNA chimeras can utilize methods known to those of skill in the art as well as those described above. A suitable reference for the synthesis, labeling and modification of PNA chimeras can be found in WIPO published patent application number WO96/40709, now issued as U.S. Pat. No. 6,063,569, herein incorporated by reference. Moreover, the methods described above for PNA synthesis and labeling often can be use for modifying the PNA portion of a PNA chimera. Additionally, well-known methods for the synthesis and labeling of nucleic acids can often be used for modifying the nucleic acid portion of a PNA chimera. Exemplary methods can be found in U.S. Pat. Nos. 5,476,925, 5,453,496, 5,446,137, 5,419,966, 5,391,723, 5,391,667, 5,380,833, 5,348,868, 5,281,701, 5,278,302, 5,262,530, 5,243,038, 5,218,103, 5,204,456, 5,204,455, 5,198,540, 5,175,209, 5,164,491, 5,112,962, 5,071,974, 5,047,524, 4,980,460, 4,923,901, 4,786,724, 4,725,677, 4,659,774, 4,500,707, 4,458,066, and 4,415,732; all of which are herein incorporated by reference.

Labeled Combination Oligomers & Oligomer Blocks:

Whether a, peptide nucleic acid, PNA chimera, PNA combination oligomer, or variation thereof, the combination oligomers or oligomer blocks that are used for the practice of this invention may be labeled with a reporter moiety. Each label or reporter moiety can be linked to any position within the combination oligomer or oligomer block, including, at the block oligomer termini, at a position internal to the oligomer blocks, or linked at a position integral to the linker. Non-limiting examples of reporter moieties (labels) suitable for directly labeling combination oligomers or oligomer blocks used in the practice of this invention include: a quantum dot, a minor groove binder, a dextran conjugate, a branched nucleic acid detection system, a chromophore, a fluorophore, a quencher, a spin label, a radioisotope, an enzyme, a hapten, an acridinium ester and a chemiluminescent compound. Quenching moieties are also considered labels. Other suitable labeling reagents and preferred methods of attachment would be recognized by those of ordinary skill in the art of PNA, peptide or nucleic acid synthesis. Non-limiting examples are described or referred to above.

Non-limiting examples of haptens include 5(6)-carboxyfluorescein, 2,4-dinitrophenyl, digoxigenin, and biotin.

Non-limiting examples of fluorochromes (fluorophores) include 5(6)-carboxyfluorescein (Flu), 2',4',1,4,-tetrachlorofluorescein; and 2',4',5',7',1,4-hexachlorofluorescein, other fluorescein dyes (See: U.S. Pat. Nos. 5,188,934; 6,008,379; 6,020,481, incorporated herein by reference), 6-((7-amino-4-methylcoumarin-3-acetyl)amino)hexanoic acid (Cou), 5(and 6)-carboxy-X-rhodamine (Rox), other rhodamine dyes (See: U.S. Pat. Nos. 5,366,860; 5,847,162; 5,936,087; 6,051,719; 6,191,278; 6,248,884, incorporated herein by reference), benzophenoxazines (See: U.S. Pat. No. 6,140,500, incorporated herein by reference)Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), other cyanine dyes (Kubista, WO 97/45539), 6-carboxy-4',5'-dichloro-2',7'-dimethoxyfluorescein (JOE), 5(6)-carboxy-tetramethyl rhodamine (Tamara), Dye 1 (FIG. 33a), Dye2 (FIG. 33b) or the Alexa dye series (Molecular Probes, Eugene, Oreg.).

Non-limiting examples of enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Non-limiting examples of quenching moieties include diazo-containing moieties such as aryldiazo compounds, e.g. dabcyl and dabsyl, homologs containing one more additional diazo and/or aryl groups; e.g. Fast Black, (Nardone, U.S. Pat. No. 6,117,986), and substituted compounds where Z is a substituent such CL F, Br, $C_1$-$C_6$ alkyl, $C_5$-$C_{14}$ aryl, nitro, cyano, sulfonate, $NR_2$, —OR, and $CO_2H$, where each R is independently H, $C_1$-$C_6$ alkyl or $C_5$-$C_{14}$ aryl according to the structures:

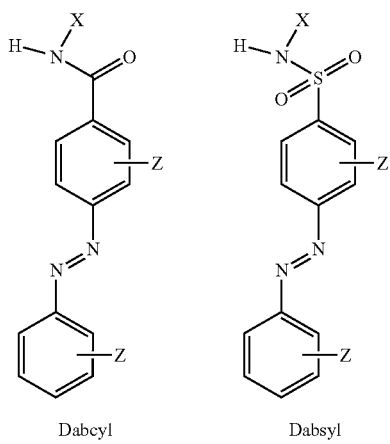

Dabcyl    Dabsyl cyanine dyes (Lee, U.S. Pat. No. 6,080,868), including the exemplary structure:

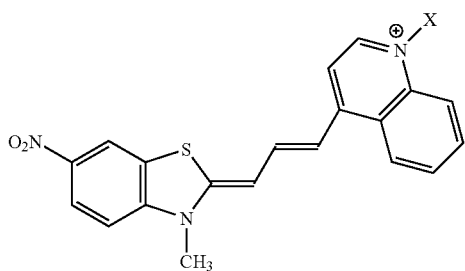

and other chromophores such as anthraquinone, malachite green, nitrothiazole, and nitroimidazole compounds and the like wherein the group X is the covalent attachment site of a bond or linker to the combination oligomers of the invention.

A non-limiting example of a minor groove binder is $CDPI_3$, represented by the structure:

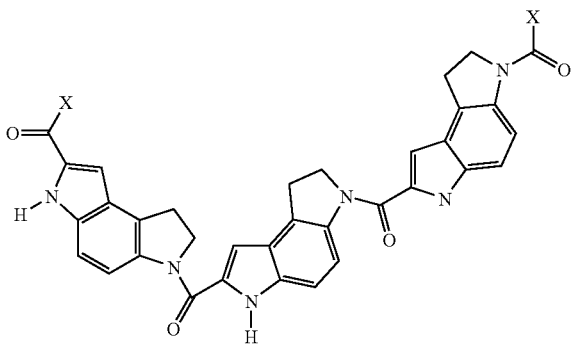

where X are exemplary attachment sites to a combination oligomer (Dempcy, WO 01/31063).

Non-radioactive labeling methods, techniques, and reagents are reviewed in: *Non-Radioactive Labeling, A Practical Introduction*, Garman, A. J. Academic Press, San Diego, Calif. (1997)

Guidance in Label Choices when Ligating/Condensing Oligomer Blocks:

It will be apparent to one of skill in the art that when oligomer blocks are to be condensed/ligated in accordance with this invention, to thereby produce a combination oligomer, the entire nature of the potentially reactive functional groups of the component oligomer blocks should be considered for potential side or cross-reactions. Protecting groups can also be used, as appropriate, to minimize or eliminate potential side or cross-reactions. For example, when labeled oligomers are to be ligated, it is wise to consider the potential for reactivity of functional groups of the one or more labels in view of the nature of the various ligation chemistries that can be chosen.

By way of illustration, when performing condensation/ligation reactions involving an amino group, carboxylic acid group and water soluble carbodiimide (e.g. Examples 2 & 6), the labels of the energy transfer set (see discussion of energy transfer set below) should generally be selected to avoid unprotected reactive amino and carboxylic functional groups to thereby avoid possible side/cross reactions. As Examples 2 and 6 demonstrate, it is possible to ligate labeled and unlabeled PNA oligomer blocks in good yield provided there are no functional groups that produce cross reactions during the condensation reaction. Consequently, one of skill in the art will therefore understand how to effect optimal ligation/condensation conditions by consideration of the nature of the reactive functional groups of the component parts in view of the nature of the particular ligation/condensation chemistry chosen.

Energy Transfer

For energy transfer to be useful in determining hybridization, there should be an energy transfer set comprising at least one energy transfer donor and at least one energy transfer acceptor moiety. Often, the energy transfer set will include a single donor moiety and a single acceptor moiety, but this is not a limitation. An energy transfer set may contain more than one donor moiety and/or more than one acceptor moiety. The donor and acceptor moieties operate such that one or more acceptor moieties accepts energy transferred from the one or more donor moieties or otherwise quenches the signal from the donor moiety or moieties. Thus, in one embodiment, both the donor moiety(ies) and acceptor moiety(ies) are fluorophores. Though the previously listed fluorophores (with suitable spectral properties) might also operate as energy transfer acceptors the acceptor moiety can also be a quencher moiety such as 4-((-4-(dimethylamino)phenyl)azo) benzoic acid (dabcyl). The labels of the energy transfer set can be linked at the oligomer block termini or linked at a site within the oligomer blocks. In one embodiment, each of two labels of an energy transfer set can be linked at the distal-most termini of the combination oligomer.

Transfer of energy between donor and acceptor moieties may occur through any energy transfer process, such as through the collision of the closely associated moieties of an energy transfer set(s) or through a non-radiative process such as fluorescence resonance energy transfer (FRET). For FRET to occur, transfer of energy between donor and acceptor moieties of a energy transfer set requires that the moieties be close in space and that the emission spectrum of a donor(s) have substantial overlap with the absorption spectrum of the acceptor(s) (See: Yaron et al. *Analytical Biochemistry*, 95: 228-235

(1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228-235 (1979) and particularly page 229, col. 1 through page 232, col. 1). This process is referred to as intramolecular collision since it is believed that quenching is caused by the direct contact of the donor and acceptor moieties (See: Yaron et al.). It is to be understood that any reference to energy transfer in the instant application encompasses all of these mechanistically-distinct phenomena. It is also to be understood that energy transfer can occur though more than one energy transfer process simultaneously and that the change in detectable signal can be a measure of the activity of two or more energy transfer processes. Accordingly, the mechanism of energy transfer is not a limitation of this invention.

Detecting Energy Transfer in a Self-Indicating Combination Oligomer:

In certain embodiments, the combination oligomers are self-indicating. In one embodiment, a self-indicating combination oligomer can be labeled in a manner that is described in co-pending and commonly owned U.S. patent application Ser. No. 09/179,162 (now allowed), entitled: "Methods, Kits And Compositions Pertaining To Linear Beacons" and the related PCT application which has also now published as WO99/21881, both of which are hereby incorporated by reference. These self-indicating combination oligomers differ from those exemplary probes first described in U.S. Ser. No. 09/179,162 or WO99/21881 primarily in presence of the linker that is situated between two oligomer blocks to which one of either a donor or acceptor moiety is linked.

Hybrid formation between a self-indicating combination oligomer and a target sequence can be monitored by measuring at least one physical property of at least one member of the energy transfer set that is detectably different when the hybridization complex is formed as compared with when the combination oligomer exists in a non-hybridized state. We refer to this phenomenon as the self-indicating property of the combination oligomer. This change in detectable signal results from the change in efficiency of energy transfer between donor and acceptor moieties caused by hybridization of the combination oligomer to the target sequence.

For example, the means of detection can involve measuring fluorescence of a donor or acceptor fluorophore of an energy transfer set. In one embodiment, the energy transfer set may comprise at least one donor fluorophore and at least one acceptor (fluorescent or non-fluorescent) quencher such that the measure of fluorescence of the donor fluorophore can be used to detect, identify or quantitate hybridization of the combination oligomer to the target sequence. For example, there may be a measurable increase in fluorescence of the donor fluorophore upon the hybridization of the combination oligomer to a target sequence (See: Examples 2, 3 and 5).

In another embodiment, the energy transfer set comprises at least one donor fluorophore and at least one acceptor fluorophore such that the measure of fluorescence of either, or both, of at least one donor moiety or one acceptor moiety can be used to can be used to detect, identify or quantitate hybridization of the combination oligomer to the target sequence.

Detection of Energy Transfer in a Detection Complex:

In another embodiment, the combination oligomers of the present invention are labeled solely with a quencher moiety and are used as a component oligomer in a Detection Complex as more fully explained in U.S. Ser. No. 09/275,848, entitled: "Methods, Kits And Compositions Pertaining To Detection Complexes" and the related PCT application which has also now published as WO99/49293, both of which are herein incorporated by reference. When the Detection Complex is formed, at least one donor moiety of one component polymer is brought sufficiently close in space to at least one acceptor moiety of a second component polymer. Since the donor and acceptor moieties of the set are closely situated in space, transfer of energy occurs between moieties of the energy transfer set. When the Detection Complex dissociates, as for example when a polymerase copies one of the strands of the Detection Complex, the donor and acceptor moieties do not interact sufficiently to cause substantial transfer of energy from the donor and acceptor moieties of the energy transfer set and there is a correlating change in detectable signal from the donor and/or acceptor moieties of the energy transfer set. Consequently, Detection Complex formation/dissociation can be determined by measuring at least one physical property of at least one member of the energy transfer set that is detectably different when the complex is formed as compared with when the component polymers of the Detection Complex exist independently and unassociated.

Detectable and Independently Detectable Moieties/Multiplex Analysis:

In certain embodiments of this invention, a multiplex hybridization assay is performed. In a multiplex assay, numerous conditions of interest are simultaneously or sequentially examined. Multiplex analysis relies on the ability to sort sample components or the data associated therewith, during or after the assay is completed. In performing a multiplex assay, one or more distinct independently detectable moieties can be used to label two or more different combination oligomers that are to be used in an assay. By independently detectable we mean that it is possible to determine one label independently of, and in the presence of, the other label. The ability to differentiate between and/or quantitate each of the independently detectable moieties provides the means to multiplex a hybridization assay because the data correlates with the hybridization of each of the distinct, independently labeled combination oligomer to a particular target sequence sought to be detected in the sample. Consequently, the multiplex assays of this invention can, for example, be used to simultaneously or sequentially detect the presence, absence, number, position or identity of two or more target sequences in the same sample and in the same assay.

Example 5, below, is one example of a multiplex assay using the invention discussed herein. In this Example, the each pair of probes used in the SNP analysis are labeled, each with a dye that fluoresces in an independently detectable color, such that: (i) if essentially only one of the two colors is detected, the sample is homozygous for one SNP condition (ii) if essentially only the other of the two colors is detected, the sample is homozygous for another SNP condition; but (iii) if both colors are detected the sample is heterozygous for the SNP condition. In this way, all of the possible SNP permutations are determinable from one "multiplex" assay wherein the independently detectable color of the fluorescent dye labels linked to different self-indicating combination oligomer probes used in the assay can be associated with a particular condition of interest and the determination of both labels in the same assay can be used to effectively call any one of three different possible SNP conditions.

Spacer/Linker Moieties:

Generally, spacers can be used to minimize the adverse effects that bulky labeling reagents might have on the hybridization properties of probes or primers. In the present invention, a linker can be used to link two or more oligomer blocks of a combination oligomer. Non-limiting examples of spacer/linker moieties suitable for use in this invention consist of: one or more aminoalkyl carboxylic acids (e.g. aminocaproic acid) the side chain of an amino acid (e.g. the side chain of lysine or ornithine) one or more natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the combination oligomer (For example see: Gildea et al., *Tett. Lett.* 39: 7255-7258 (1998)).

The linkers of this invention are abasic. By abasic we mean that they do not comprise a nucleobase. The linkers are at least three atoms in length. For the avoidance of doubt, the atoms that define the linker are not atoms that make up the monomer subunits of the oligomer. For example the 3' and 5' hydroxyl groups of a nucleotide subunit are not atoms of the linker. Similarly, the primary amine and carbonyl carbon of the N-(2-aminoethyl)-glycine moiety of a PNA subunit are not counted as being atoms of the linker.

For example, the linker can be one amino acid residue, two amino acid residues, three amino acid residues, one E-linker residue, two E-Linker residues, one O-linker residue, two O-linker residues, one X-linker residue or two X-linker residues. More specifically, the linker can be the amino acid glycine, the amino acid dimer gly-gly, the amino acid dimer gly-lys, the amino acid dimer lys-gly, the amino acid dimer glu-gly, the amino acid dimer gly-cys, the amino acid dimer cys-gly and the amino acid dimer asp-gly.

Hybridization Conditions/Stringency:

Those of ordinary skill in the art of hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a combination oligomer/target sequence combination is often found by the well-known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal or suitable stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Often this is achieved by adjusting stringency until sequence specific hybridization of the probe and target sequence is achieved. Nevertheless, aided by no more than routine experimentation and the disclosure provided herein, those of skill in the art will be able to determine suitable hybridization conditions for performing assays utilizing the methods and compositions described herein.

Blocking Probes:

Blocking probes are nucleic acid or non-nucleic acid probes that can be used to suppress the binding of the probing nucleobase sequence of the combination oligomer to a non-target sequence. Preferred blocking probes are PNA probes (See: Coull et al., U.S. Pat. No. 6,110,676, herein incorporated by reference). The combination oligomers of this invention can likewise be used as blocking probes.

Typically, blocking probes are closely related to the probing nucleobase sequence and preferably they comprise one or more single point mutations as compared with the target sequence sought to be detected in the assay. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods and compositions of this invention to suppress the binding of the nucleic acid or non-nucleic acid combination oligomer to a non-target sequence that might be present in an assay and thereby interfere with the performance of the assay. (See: Fiandaca et al. *"PNA Blocker Probes Enhance Specificity In Probe Assays"*, Peptide Nucleic Acids: Protocols and Applications, pp. 129-141, Horizon Scientific Press, Wymondham, UK, 1999)

Probing Nucleobase Sequence:

The probing nucleobase sequence of a combination oligomer is the specific sequence-recognition portion of the construct. We refer to the oligomers of this invention as combination oligomers, without regard to the method of production, because their hybridization properties result from the combined properties of the two or more component oligomer blocks, the nature of the linker and the opportunity for interaction between the blocks when the combination oligomer sequence specifically hybridizes to a target sequence. Therefore, the probing nucleobase sequence of a combination oligomer is an aggregate nucleobase sequence of the oligomer blocks that are designed to hybridize to a specific target sequence of contiguous nucleobases in a sample (See for Example: FIG. 1). Accordingly, the probing nucleobase sequence of the combination oligomer is distributed (not necessarily evenly distributed) between at least two oligomer blocks of the combination oligomer. Consequently, with due consideration to the requirements of a combination oligomer for the assay format chosen, the length and sequence composition of the probing nucleobase sequence of the combination oligomer will generally be selected to form a double stranded complex with a target sequence of contiguous nucleobases (i.e. the oligomer blocks hybridize juxtaposed such that there is no gap) under suitable hybridization conditions.

As discussed in Example 1, the combination oligomers of this invention may exhibit both a lower Tm than a native oligomer of equivalent probing nucleobase sequence and a greater ability to discriminate mismatches when the mismatch is located other than at the termini of one oligomer block. Hence, the design of the probing nucleobase sequence of a combination oligomer may involve the positioning of single point mutations (mismatches, single nucleotide polymorphisms or SNPs) that are to be distinguished at a position other than at the termini of an oligomer block.

Non-limiting Examples of Ligation/Condensation Chemistries

Figure 28A:
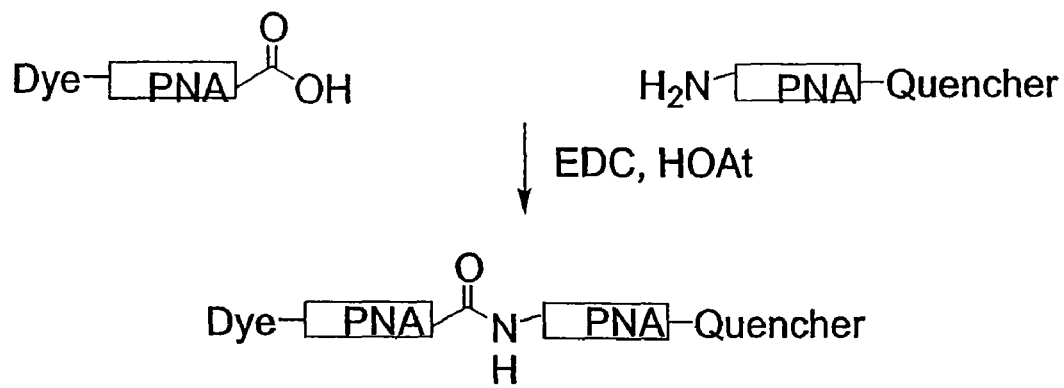
FIGS. 28a and 28b are illustrations of possible ligation reactions wherein one oligomer block comprises an amino group that couples to the carboxylic acid group of a second oligomer block.
Figure 28B:
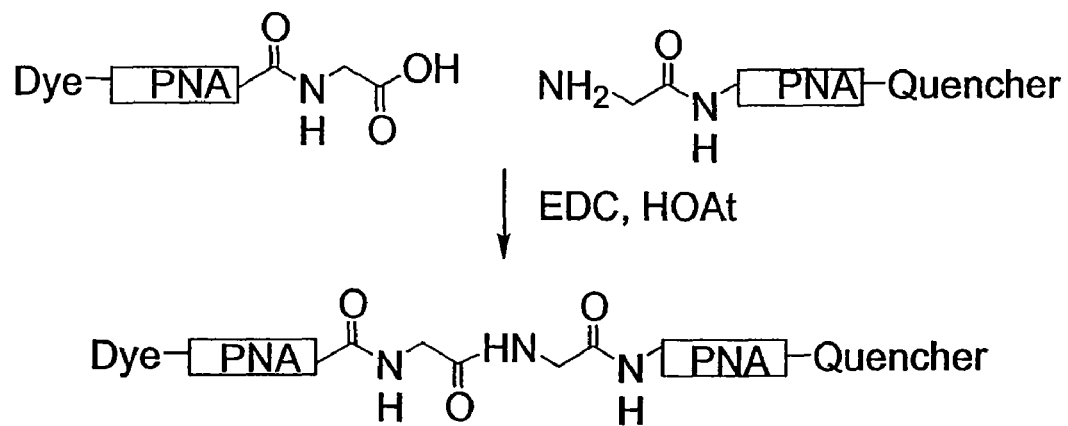

With reference to FIGS. 28a and 28b, properly prepared oligomer blocks can be ligated using a carbodiimide, such as the water-soluble carbodiimide 1-Ethyl-3-(3-Dimethylamino-propyl)carbodiimide hydrochloride (EDC). As illustrated, typically one of the oligomer blocks comprises a carboxylic acid moiety and the other comprises an amine group. As PNA oligomers, whether or not they comprise linked natural amino acid moieties, can comprise an amine terminus and a carboxylic acid terminus, it is an advantage that PNA oligomer blocks do not require modification to facilitate this ligation chemistry. The oligomers can be ligated in an aqueous solution, optionally containing 1 percent to 75 percent organic modifier (v/v). The pH can be less than 6.5. Applicants have observed that the addition of an activating reagent such as a triazole compound (e.g. 1-Hydroxy-7-azabenzotriazole (HOAt) or 1-Hydroxybenzotriazole (HOBt)) will increase the overall yield of the condensation/ligation reaction. Accordingly it is recommended that an activation reagent be used with the carbodiimide to effect the ligation when this chemistry is chosen.

Again with reference to FIGS. 28a and 28b, the product of ligation of FIG. 28a is a native PNA oligomer whereas the product of ligation of FIG. 28b is a combination oligomer comprising a gly-gly linker. Accordingly, it is to be understood that oligomer blocks can be selected to prepare both native and combination oligomers and that the choice of oligomer blocks of, for example, a library can be produced with the desired product of condensation/ligation in mind.

With reference to FIGS. 29a, 29b, 29c, 30a and 30b, several options for the ligation/condensation of oligomer blocks are illustrated wherein sodium cyanoborohydride is used as reducing reagent. It is to be understood that sodium cyanoborohydride is one of many reducing reagents that could be used to effect the ligation of the oligomer blocks using these strategies for ligation.

Figure 29A:
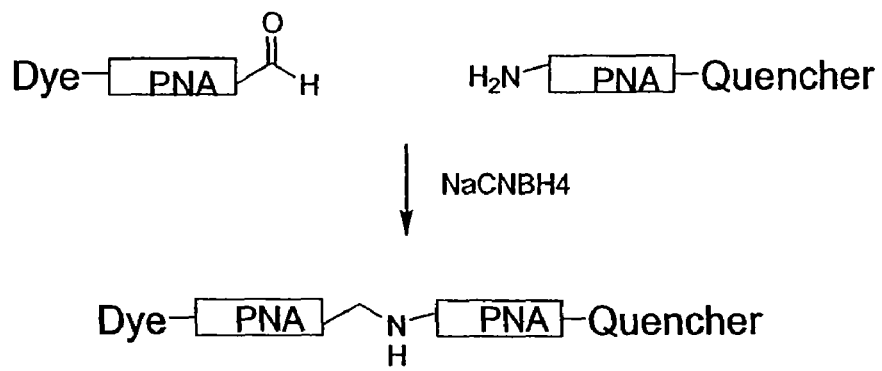
FIGS. 29a, 29b and 29c are illustrations of possible ligation reactions involving borohydride reduction.
Figure 29B:
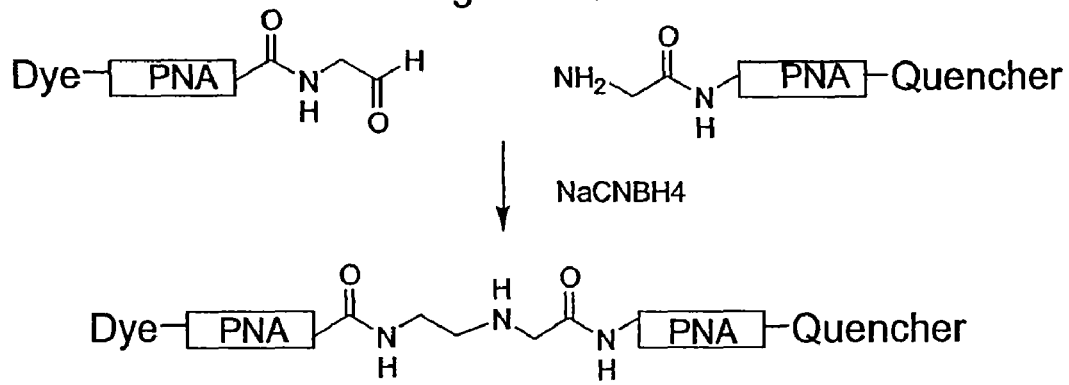

With reference to FIGS. 29a and 29b, one of the oligomer blocks to be ligated comprises an amine and the other oligomer block to be ligated comprises an aldehyde. The oligomer blocks can be brought into contact to thereby form an imine. Because imine formation is reversible, the imine is often reduced, by for example sodium cyanoborohydride, to thereby form the ligated combination oligomer. With reference to FIGS. 29a and 29b, the illustrations are analogous to that observed with FIGS. 28a and 28b, respectively in that the product of ligation is either a native oligomer or a combination oligomer, in this case comprising an N-[2-aminoethyl]-glycine linker.

Figure 29C:
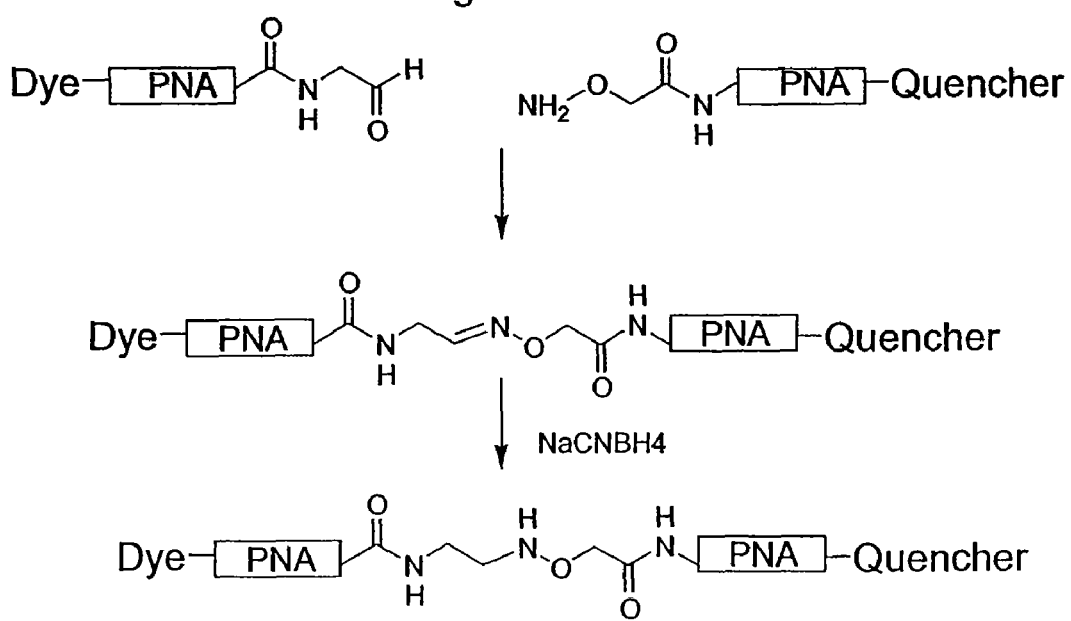
Figure 30A:
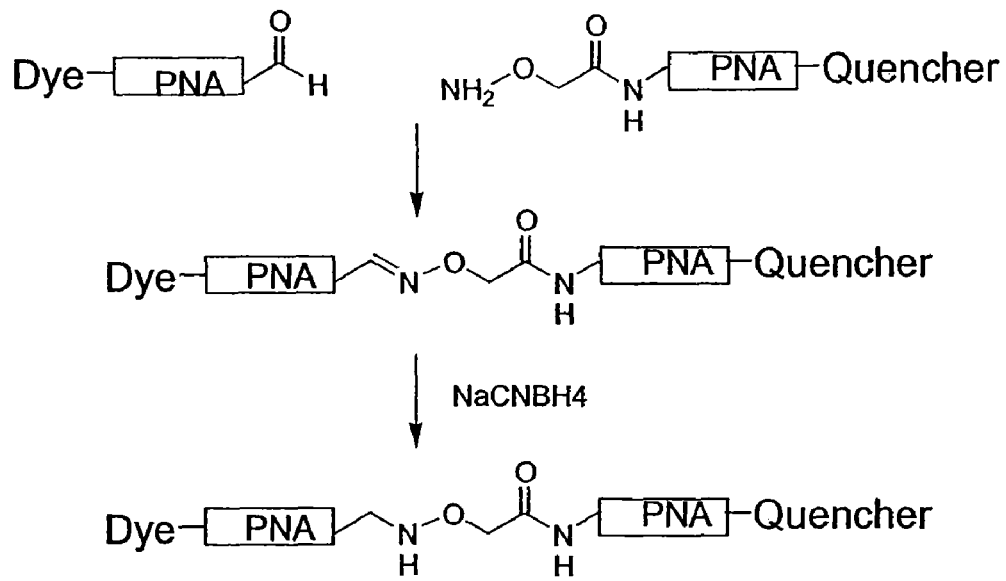
FIGS. 30a and 30b are illustrations of additional possible ligation reactions involving borohydride reduction.
Figure 30B:
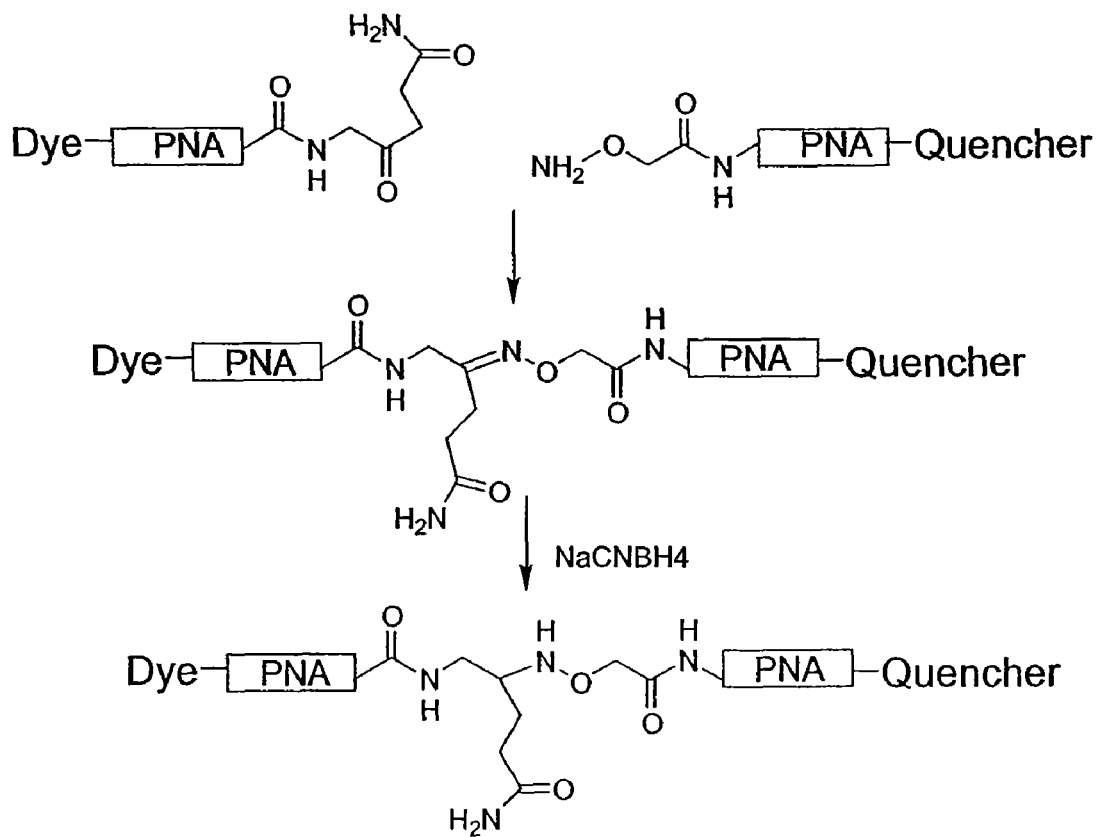

With reference to FIGS. 29c, 30a and 30b, one of the oligomer blocks to be ligated is an aldehyde or ketone, such as glycinal or β-alinal, and the other oligomer block to be ligated comprises an aminooxy-containing moiety such as aminooxyacetyl. Reaction of properly modified oligomer blocks results in the formation of an iminoxy combination oligomer that is more stable than an imine. Accordingly, the iminoxy combination oligomer can be used as prepared or can optionally be reduced with, for example, sodium cyanoborohydride to thereby a more stable combination oligomer comprising a linker, as illustrated.

Figure 31A:
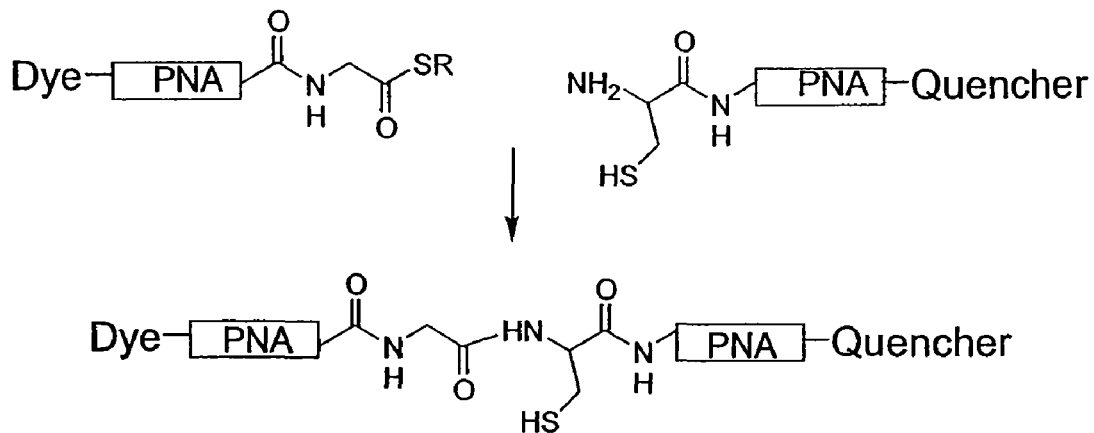
FIGS. 31a, 31b and 31c are illustrations of possible ligation reactions involving thiol reactive groups.
Figure 31B:
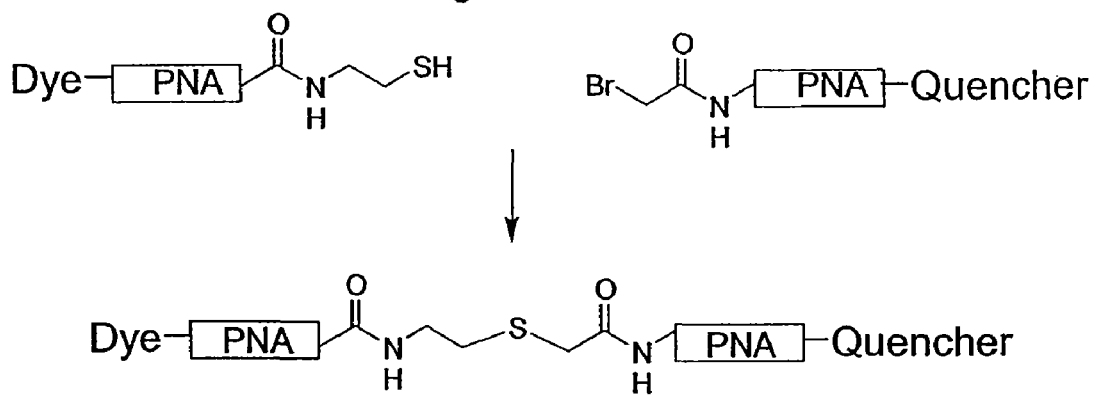
Figure 31C:
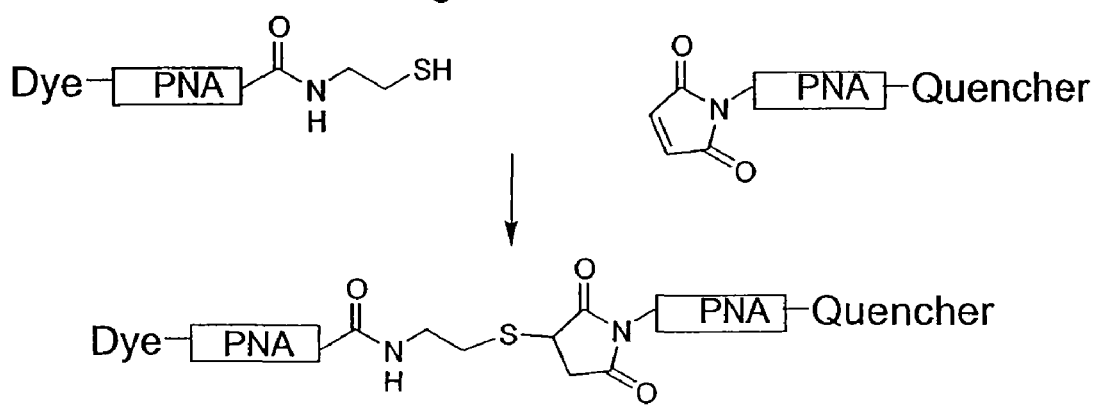

With reference to FIGS. 31a, 31b and 31c, in each case one of the oligomer blocks comprises a nucleophilic thiol and a leaving group. FIG. 31a illustrates ligation in accordance with Lu et al. (J. Am. Chem. Soc., 118(36): 8518-8523 (1996)) to thereby form a combination oligomer. Reaction of a nucleophilic thiol, such as 2-aminoethyl thiol (FIG. 31c), 2-thioacetyl or 3-thiopropionyl, with, for example, either haloacetyl (FIG. 31b), malimido (FIG. 31c) or vinyl will likewise produce a combination oligomer.

Immobilization of Combination Oligomers to a Solid Support or Surface:

One or more of the combination oligomers of this invention may optionally be immobilized to a surface or solid support for the detection of a target sequence. Immobilization can, for example, be used in capture assays and to prepare arrays.

The block oligomers and/or combination oligomers can be immobilized to a surface using the well known process of UV-crosslinking. The oligomer blocks can also be synthesized on the surface in a manner suitable for deprotection but not cleavage from the synthesis support (See: Weiler, J. et al, Hybridization based DNA screening on peptide nucleic acid (PNA) oligomer arrays, Nucl. Acids Res., 25, 14:2792-2799 (July 1997)). In still another embodiment, one or more combination oligomers can be covalently linked to a surface by the reaction of a suitable functional group on the oligomer with a functional group of the surface (See: Lester, A. et al, "PNA Array Technology": Presented at Biochip Technologies Conference in Annapolis (October 1997)). This method is advantageous as compared to several of the other methods since the oligomers deposited on the surface for immobilization can be highly purified and attached using a defined chemistry, thereby possibly minimizing or eliminating non-specific interactions.

Methods for the chemical attachment of oligomer blocks or combination oligomers to surfaces may involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the oligomer. Because native PNA possesses an amino terminus, a PNA may or may not require modification to thereby immobilize it to a surface (See: Lester et al., Poster entitled "PNA Array Technology").

Conditions suitable for the immobilization of a combination oligomer to a surface will generally be similar to those conditions suitable for the labeling of the polymer. The immobilization reaction is essentially the equivalent of labeling whereby the label is substituted with the surface to which the polymer is to be linked (see above).

Numerous types of solid supports derivatized with amino groups, carboxylic acid groups, isocyantes, isothiocyanates and malimide groups are commercially available. Non-limiting examples of suitable solid supports include membranes, glass, controlled pore glass, polystyrene particles (beads), silica and gold nanoparticles. All of the above recited methods of immobilization are not intended to be limiting in any way but are merely provided by way of illustration.

NON-LIMITING LIST OF ADVANTAGES ASSOCIATED WITH THE PRESENT INVENTION

Combination oligomers comprising unprotected nucleobases can be efficiently ligated in the absence of a template. The efficiency of ligation also does not appear to be largely dependent upon scale thereby facilitating a broad range of use, particularly for numerous applications where the cost of conventional de novo oligomer synthesis is prohibitive such as where the amount of oligomer generated can be far in excess of that which is required. Hence, the present method enables the production of oligomers of desired nucleobase sequence in desired quantities and can possibly produce substantial cost savings as compared with de novo methods.

Combination oligomers of desired nucleobase sequence can be rapidly and efficiently prepared in a single step from a readily available library of oligomer blocks (the "library approach"). The ability to rapidly manufacture oligomers of defined nucleobase sequence that can bind to a target sequence is enabling to high throughput applications such as nucleic acid sequencing, SNP analysis, genetic analysis, expression analysis and array production because tens, hundreds, thousands, tens or even hundreds of thousands and possibly millions of probes can be produced in a very time critical manner.

Combination oligomers, although generally exhibiting a lower absolute Tm as compared with native oligomers, may exhibit a larger ΔTm when the two oligomer blocks hybridize juxtaposed to a binding pair such that there is no gap (See: FIG. 1). Because of this larger ΔTm, as compared with the native oligomer, these combination oligomers can be more specific and discriminating as compared with the native oligomers (See: Egholm et al., Nature, 365: 566-568 (1993) wherein it is noted that the larger ΔTm for a PNA mismatch as compared with that of a nucleic acid mismatch is a measure of the discriminating power of the molecule in a hybridization reaction). Because of the high discriminating power of the combination oligomers, an assay for a single point mutation (also know as a single nucleotide polymorphism (SNP)) can be designed wherein the oligomer operates in essentially a binary mode such that it is either bound or unbound depending upon whether or not the wild type or mutant target is present. The hybrid of a 10-mer PNA combination oligomer and its complementary target sequence typically exhibits a Tm that is slightly above ambient temperature (e.g. 35-45° C.). However, one or more non-complementary nucleobases in the hybrid will lower the Tm below room temperature. Hence, 10-mer PNA combination oligomers can be particularly useful and discriminating in analyses that are performed at ambient temperature. Since analysis at ambient temperature avoids the need for expensive temperature control equipment, this property of the hybrids and assays of this invention convey a substantial advantage to the ordinary practitioner.

Combination oligomers can be designed to comprise an enzyme cleavage site as the linker that links two oligomer blocks. The incorporation of such a cleavage site can be advantageous when considered in combination with Applicant's observation that the combination oligomers can, depending upon the nature of the enzyme and cleavage site present, be protected from cleavage as a result of the binding of the combination oligomer to a suitable binding pair (e.g. a target sequence). Thus, by incorporating such a linker, it is an advantage that certain combination oligomers can be used as substrates in an assay to, among other uses, determine whether or not a potential binding partner binds to the combination oligomer since whether or not there is binding, and in what amount, can be used to determine whether or not, and in what amount, the binding partner (e.g. a target sequence) is present in a sample.

Oligomer purification by conventional methods such a high performance liquid chromatography (HPLC) can expensive and time consuming. Because the combination oligomers are themselves produced from purified subunits, delivery can be more rapid and cost effective where the product need not be purified post ligation. Moreover, because the unreacted component oligomer blocks that are ligated are typically too short to form a stable hybrid at or above ambient temperature, and therefore are not necessarily problematic impurities, in many applications there may not be a requirement that the combination oligomer be purified post-ligation and prior to use. This can facilitate the rapid availability of probes/primers of desired composition once a proper library has been constructed.

NON-LIMITING EXAMPLES OF APPLICATIONS FOR THE PRESENT INVENTION

The method, kits, compositions, libraries and arrays of this invention are useful in many areas or applications of scientific investigation. For example, this invention may be useful for the detection, identification and/or enumeration of viruses, bacteria and eucarya (e.g. pathogens) in food, beverages, water, pharmaceutical products, personal care products, dairy products or in samples of plant, animal, human or environmental origin. The invention may also be useful for the analysis of raw materials, equipment, products or processes used to manufacture or store food, beverages, water, pharmaceutical products, personal care products dairy products or environmental samples. Additionally, this invention may be useful for the detection of bacteria and eucarya (e.g. pathogens) in clinical specimens, equipment, fixtures or products used to treat humans or animals as well as in clinical samples and clinical environments. For example, the analysis for microorganisms of interest can be performed using PNA-FISH or multiplex PNA-FISH (See: Example 3 of this specification as well as co-pending and co-owned U.S. application Ser. Nos. 09/335,629 and 09/368,089).

The method, kits, compositions, libraries and arrays of this invention are particularly useful in areas such as expression analysis, single nucleotide polymorphism (SNP) analysis (See: Example 5, below), genetic analysis of humans, animals, fungi, yeast, viruses, and plants (including genetically modified organisms), therapy monitoring, pharmacogenomics, pharmacogenetics, epigenomics, and high throughput screening operations. The libraries of this invention may be useful for these probe intensive applications because they facilitate the massive, rapid, efficient and appropriately scaled synthesis of highly selective/discriminating combination oligomers; a requirement that has yet to be adequately fulfilled to thereby fully enable these probe or primer intensive applications.

II. Exemplary Embodiments of the Invention

Combination Oligomers in General:

This invention pertains to the field of combination oligomers, including the block synthesis of combination oligomers in the absence of a template, as well as related methods, kits, libraries and other compositions. The combination oligomers of this invention can be produced either by stepwise assembly of monomers/synthons (de novo synthesis) using commercially available chemicals and instrumentation. Alternatively, the combination oligomers can be produced by ligation as generally described below (the "library approach"); for example as specifically described in Examples 2 and/or Example 6 of the specification. One of skill in the art can determine the mode of combination oligomer production that is best suited for the application chosen in view of one's own resources. Consequently, it is to be understood that the method of production of a combination oligomer is not intended to be a limitation of the present invention.

As used herein a combination oligomer is a composition comprising two or more oligomer blocks independently selected from peptide nucleic acid, PNA chimera and PNA combination oligomer, whether or not labeled, wherein said oligomer blocks are linked by a linker. This linker can optionally be a cleavage site for an enzyme. The aforementioned composition is referred to herein as a combination oligomer, without regard to its method of production, because its hybridization properties result from the combined properties of the two component oligomer blocks as well as the nature of the linker and the opportunity for interaction between the blocks when the combination oligomer hybridizes to a target sequence.

It is to be understood that combination oligomers can be used as probes or primers in numerous applications. The requirement for probes is merely that they hybridize to a target sequence with sequence specificity. Thus, when used as a probe, there are no additional limitations on specific features of the combination oligomer. However, when used as a primer, it is a requirement that the combination oligomer contain moieties suitable for the recognition and operation of an enzyme since polymerase enzymes are not known to operate on unmodified PNA oligomers (See: Lutz et al., *J. Am. Chem. Soc.* 119: 3177-3178 (1997)).

It is to be understood that for many embodiments of this invention, it is this generic embodiment of a combination oligomer that is to be considered with respect to the description of the invention. Unless otherwise specifically noted herein, the novel combination oligomers referred to herein as self-indicating combination oligomers and substrate combination oligomers may comprise limitations not generally applicable to other embodiments of the invention.

Novel Combination Oligomers:

In one embodiment, this invention pertains to novel combination oligomers. The novel combination oligomers of this invention include, but are not necessarily limited to, substrate combination oligomers or self-indicating combination oligomers, as discussed below. (See also: Examples 1, 4 & 5, below). Whether a substrate combination oligomer or self-indicating combination oligomer, these novel combination oligomers comprise a segment of the formula: A-W-C or A-B-C, wherein W or B are used to distinguish whether or not, respectively, the linker comprises an enzyme cleavage site. Thus, the novel substrate combination oligomers of this invention comprise the linker W that is a substrate for an enzyme whereas the self-indicating combination oligomers are generally illustrated by use of the linker B. However, a self-indicating combination oligomer may also be a substrate combination oligomer (See for example: Example 4).

According to the invention, A and C are oligomer blocks independently selected either as peptide nucleic acid, PNA chimera or PNA combination oligomer. The linker B or W, as the case may be, is a linkage that is at least three atoms in length that covalently links oligomer block A to oligomer block C. In this configuration, one or more additional oligomer blocks or other moieties such as a solid support, one or more protected or unprotected functional groups or one or more labels may be covalently attached to either or both of A and C.

Self-Indicating Combination Oligomers:

In one embodiment, this invention pertains to self-indicating combination oligomers. Accordingly, this invention also pertains to a composition of covalently linked oligomer blocks comprising a segment of the formula: A-B-C. Oligomer blocks A and C are each independently a peptide nucleic acid, PNA chimera or PNA combination oligomer and are optionally linked to other moieties of the segment. The linker B is at least three atoms in length and covalently links oligomer block A to oligomer block C. Moreover, oligomer blocks A and C taken together encode a probing nucleobase sequence that is designed to sequence specifically hybridize to a target sequence of contiguous nucleobases to thereby form a double stranded target sequence/combination oligomer complex.

A self-indicating combination oligomer further comprises an energy transfer set of labels such that at least one acceptor moiety of the energy transfer set is linked to one of the linked oligomer blocks of the composition whilst at least one donor moiety of the energy transfer set is linked to another of the linked oligomer blocks of the composition wherein labels of the set are linked to the combination oligomer at positions that facilitate a change in detectable signal of at least one label when the combination oligomer is hybridized to a target sequence as compared to when the combination oligomer is in a non-hybridized state. As previously discussed, self-indicating combination oligomers are so named because there occurs, through any energy transfer mechanism, a change in detectable signal upon hybridization of the oligomer as compared to when the oligomer exists in a non-hybridized state. Accordingly, the state of hybridization of the oligomer can be determined in either real-time or at the end point of an assay. Moreover sets of independently detectable combination oligomers can be prepared for multiplex analysis as demonstrated in Example 5.

In other embodiments of this invention, the self-indicating combination oligomer may optionally further comprises one or more protected or unprotected functional groups or is otherwise labeled with one or more additional reporter moieties. According to the invention, the functional groups or reporter moieties can, each independently, be linked at the oligomer block termini, linked at a position internal to the oligomer blocks or linked at a position integral to the linker. Suitable reporter moieties have been previously described herein. The one or more protected or unprotected functional groups can be used, when deprotected, to link a reporter moiety thereto or otherwise be used to link the combination oligomer to a support. Consequently, the self-indicating combination oligomers can be support bound, including as appropriate, being one oligomer of an array of oligomers, including an array of self-indicating combination oligomers.

Substrate Combination Oligomers:

In another embodiment, this invention pertains to substrate combination oligomers. Accordingly, this invention also pertains to a composition of covalently linked oligomer blocks comprising a segment of the formula: A-W-C. Oligomer blocks A and C are each independently a peptide nucleic acid, PNA chimera or PNA combination oligomer. The linker W is at least three atoms in length and covalently links block A to block C. The linker W also comprises is a cleavage site for an enzyme.

Non-limiting examples of the linker W that comprises a cleavage sites include, but are not limited to: lys-X, arg-X, Glu-X, asp-X, asn-X, phe-X, leu-X, lys-gly, arg-gly, glu-gly and asp-glu, wherein X is any naturally occurring amino acid. A list of non-limiting examples of enzymes suitable for cleaving one or more of these substrates include: Endoprotinase Glu-C (EC 3.4.21.19), Lys-C (EC 3.4.21.50), Arg-C (EC 3.4.22.8), Asp-N (EC 3.4.24.33), Papain (EC 3.4.22.2), Pepsin (EC 3.4.23.1), Proteinase K (3.4.21.14), chymotrypsin (EC 3.4.21.1) and trypsin (3.4.21.4).

In other embodiments of this invention, the substrate combination oligomer may optionally further comprises one or more protected or unprotected functional groups or is otherwise labeled with one or more reporter moieties. According to the invention, the functional groups or reporter moieties can, each independently, be linked at the oligomer block termini, linked at a position internal to the oligomer blocks or linked at a position integral to the linker. Suitable reporter moieties have been previously described herein. The one or more protected or unprotected functional groups can be used, when deprotected, to link a reporter moiety thereto or otherwise be used to link the combination oligomer to a support. Consequently, the substrate combination oligomer, whether or not it is labeled, can be support bound, including as appropriate, being one oligomer of an array of oligomers, including an array of substrate combination oligomers.

Hybrid of a Target Sequence and a Combination Oligomer:

In another embodiment, this invention pertains to a composition comprising a polynucleobase strand and a combination oligomer sequence specifically hybridized to a target sequence of contiguous nucleobases within the polynucleobase strand to thereby form a double stranded target sequence/combination oligomer complex (See FIG. 1; Also note that this configuration is sometimes referred to herein as being hybridized juxtaposed to the target sequence such that there is no gap or gap base). The combination oligomer comprises a first and a second oligomer block that are each independently a peptide nucleic acid, PNA chimera or PNA combination oligomer. The first and second oligomer blocks are covalently linked by a linker of at least three atoms in length. The hybrid can be formed by contacting the combination oligomer with the polynucleobase strand under suitable hybridization conditions.

The combination oligomer of the hybrid may be unlabeled or further comprise protected or unprotected functional groups and/or reporter moieties. The combination oligomer may be a self-indicating combination oligomer. The linker of the combination oligomer may comprise a cleavage site for an enzyme. The hybrid may exist free in solution or be support bound. In certain embodiments, the hybrid may exist at a unique position of an array.

Method for Determining a Target Sequence

In yet another embodiment, this invention pertains to a method for determining a target sequence of contiguous nucleobases. The method comprises contacting the target sequence with a combination oligomer, under suitable hybridization conditions, wherein the combination oligomer comprises a first oligomer block and a second oligomer block that are each independently a peptide nucleic acid, PNA chimera or PNA combination oligomer. The first and second oligomer blocks are linked covalently to each other by a linker that is at least three atoms in length. Moreover, the first and second oligomer blocks can sequence specifically hybridize to the target sequence of contiguous nucleobases to thereby form a double stranded target sequence/combination oligomer complex. Accordingly, the aggregate of the first and second oligomer blocks comprise the probing nucleobase sequence. Complex formation is determined to thereby determine the target sequence since the complex does not form in the absence of the target sequence. Determination of the complex includes, but is not limited to, determining the presence, absence, quantity (amount) or position of the complex to thereby determine the presence, absence, quantity (amount), position or identity of the target sequence (See for example: Examples 3-5).

According to the method, the combination oligomer of the hybrid may be unlabeled or further comprise protected or unprotected functional groups and/or reporter moieties. The combination oligomer may be a self-indicating combination oligomer. The linker of the combination oligomer may comprise a cleavage site for an enzyme. The complex may exist free in solution or be support bound. In certain embodiments, the complex may exist at a unique position of an array.

It is to be understood that where the combination oligomer is labeled, determination of complex formation may involve the determination of one or more of the labels. However, where the combination oligomer is unlabeled, the target sequence, or polynucleobase strand comprising the target sequence, can optionally be labeled such that determination of the label facilitates the determination of the formation of the complex. In still another embodiment, neither of the combination oligomer or the target sequence is labeled. Even though the complex is not directly labeled, it is still possible to determine complex formation. For example, since the complex comprises at least a segment of a PNA/nucleic acid hybrid, the hybrid can be determined using an antibody that has been raised to determine PNA/nucleic acid hybrids (See: Hyldig-Nielsen et al., U.S. Pat. No. 5,612,458, herein incorporated by reference).

Method for Determining the Zygosity of a SNP

In still another embodiment, this invention pertains to a method for determining the zygosity of a nucleic acid for a single nucleotide polymorphism (SNP). The method comprises contacting a nucleic acid sample with at least two independently detectable combination oligomers. Each independently detectable combination oligomer comprises a first oligomer block and a second oligomer block that are each independently a peptide nucleic acid, PNA chimera or PNA combination oligomer. The oligomer blocks are linked covalently to each other by a linker that is at least three atoms in length. The first and second oligomer blocks taken together encode a probing nucleobase sequence that is designed to sequence specifically hybridize to a target sequence of contiguous nucleobases in a polynucleobase strand of the nucleic acid sample, if present, to thereby form a double stranded target sequence/independently detectable combination oligomer complex. The probing nucleobase sequence in each independently detectable combination oligomer differs from the other by at least one nucleobase (the SNP nucleobase). However, the probing nucleobase sequence may differ by more than one nucleobase, depending on probe design, provided however that they differ by a single nucleobase at the SNP to be determined (See for example: Example 5, Table 9 and particularly the sets of PNA combination oligomer probes for SNPs 6876 and 6879).

According to the method, the nucleic acid sample and combination oligomers are contacted with one or more reagents suitable for performing a nucleic amplification reaction that amplifies the nucleic acid present in the sample and the nucleic acid amplification is performed in the presence of the nucleic acid, the combination oligomers and the reagents. Non-limiting examples of nucleic acid amplification reactions include: Polymerase Chain Reaction (PCR), Ligase Chain Reaction (LCR), Strand Displacement Amplification (SDA), Transcription-Mediated Amplification (TMA), Q-beta replicase amplification (Q-beta) and Rolling Circle Amplification (RCA).

Complex formation for each independently detectable combination oligomer/target sequence complex is determined to thereby determine whether the nucleic acid is heterozygous or homozygous for a particular SNP. Complex determination can be correlated with the zygosity state of a particular SNP, since the complexes will not form in the absence of the respective target sequence of contiguous nucleobases for each particular combination oligomer. Moreover, signal for the two independently detectable combination oligomers provides all of the information needed to determine the three possible genotype states depending on which complexes do and do not form.

In one embodiment, the independently detectable combination oligomers are independently detectable, self-indicating combination oligomers. According to the method a determination, under suitable hybridization conditions, is made of any change in detectable signal arising from at least one of the labels of each of the independently detectable energy transfer sets as a measure of whether or not each of the combination oligomers is hybridized to their respective target sequence of contiguous nucleobases. Such determination can be performed either during the process of the nucleic acid amplification (e.g. in real-time) or after the nucleic acid amplification reaction is completed (e.g. at the end-point). According to the method, the result of the change in signal for at least one label of each energy transfer set of each combination oligomer is correlated with a determination of the formation of each of the two possible target sequence/independently detectable self-indicating combination oligomer complexes. Based upon this data, one of the three possible states of zygosity of the sample for a particular SNP can be determined (See for example: Example 5). The target sequence/combination oligomer complex/hybrid can be free in solution or it can be support bound when the determination is made.

Non-Template Directed Methods for Forming Combination Oligomers

In another embodiment, this invention is directed to a method for forming a combination oligomer from oligomer blocks. The method comprises reacting a first oligomer block, a second oligomer block, and optionally a condensation reagent or reagents under condensation conditions to thereby form a combination oligomer having a linker of at least three atoms in length that covalently links the first oligomer block to the second oligomer block. According to the method, the first and second oligomer blocks are each independently a peptide nucleic acid, PNA chimera or PNA combination oligomer. Neither of the first or second oligomer blocks is support bound and the combination oligomer forms in the absence of a template. The ligation/condensation reaction can be performed in aqueous solution. The nucleobases need not be protected during the condensation/ligation reaction.

In yet another embodiment, this invention pertains to another method for forming combination oligomers from oligomer blocks. The method comprises reacting a first oligomer block, a second oligomer block, and optionally a condensation reagent or reagents under condensation conditions to thereby form a combination oligomer having a linker of at least three atoms in length that covalently links the first oligomer block to the second oligomer block. The first and second oligomer blocks are each independently a peptide nucleic acid, PNA chimera or PNA combination oligomer. The nucleobases of the oligomer blocks do not comprise protecting groups and the combination oligomer forms in the absence of a template. The ligation/condensation can be performed in aqueous solution. Moreover, one of the oligomer blocks may or may not be support bound.

Regardless of the method of forming a combination oligomer as described above, in another embodiment, the product of the condensation/ligation reaction can optionally be further lengthened/elongated. Hence, the combination oligomer, as formed, can be used as an oligomer block such that repeating the method produces a further lengthened/elongated oligomer. According to the method, the combination oligomer, as previously formed, can optionally be deprotected, as may be required, to facilitate the next condensation/ligation step. The combination oligomer, as previously formed and optionally deprotected, is reacted with a third oligomer block and optionally a condensation reagent or reagents under condensation conditions. This forms the elongated combination oligomer having a covalent linkage of at least three atoms in length that covalently links the third oligomer block to the combination oligomer wherein, the elongated combination oligomer forms in the absence of a template. In accordance with this method, this process can be optionally repeated until the combination oligomer is of the desired length. Such a process of continued elongation can, for example, be useful for the preparation of arrays since longer oligomers are often used for this application.

According to this method of the invention, the component oligomer blocks are either fully unprotected or one or both are partially protected. Accordingly, the oligomer blocks may comprise protected functional groups. By partially protected we mean that an electrophilic or nucleophilic functional group of the oligomer blocks are protected from reaction, during the condensation, by a removable protecting group; it being self evident that the protecting group can be removed, for example, after the condensation reaction is performed to thereby prepare the combination oligomer for subsequence condensation/ligation, to introduce a label or to link the combination oligomer to a support.

Despite the absence of a template, Applicants have been able to rapidly, efficiently and repeatedly obtain combination oligomers in greater that fifty percent (50%) yield (See: Examples 2 and 6), whether or not the oligomer blocks are labeled. The efficiency of this non-template directed ligation is surprising in view of published results wherein it is noted that essentially no ligation was observed in the absence of a template (See: Koppitz et al., *J. Am. Chem. Soc.* 120: 4563-4569 (1998) at page 4565, col. 1, lines 16-20 as well as Farèse et al., *Tett. Lett.* 37: 1413-1416 (1996)).

The ligation/condensation methods of this invention can be used for the production of both labeled and unlabeled combination oligomers, including without limitation, both substrate combination oligomers as well as self-indicating combination oligomers. The combination oligomers produced by the methods of this invention may otherwise comprise one or more protected or unprotected functional groups (the presence of unprotected functional groups depends in part on the nature of the ligation/condensation chemistry chosen so as to avoid or minimize possible cross-reactions). The ligation methods can be used to produce a linker comprising a cleavage site for an enzyme. Moreover, the ligation methods described herein can be used for the production of support bound combination oligomers as well as arrays comprising one or more combination oligomers.

All oligomer blocks of the combination oligomer can be peptide nucleic acid. Either, or both, of the terminal oligomer blocks or condensation oligomer blocks can contain at least one region of constant nucleobase sequence and at least one region containing variable nucleobase sequence. The constant nucleobase sequence can be between 1 to 10 nucleobase containing subunits in length and the variable region can be between 3 to 8 nucleobase containing subunits in length.

A Method for Determining Binding of a Combination Oligomer to a Binding Partner

In certain other embodiments of this invention, a combination oligomer is formed that possesses a cleavage site for an enzyme wherein the cleavage site is protected from cleavage upon the binding of the combination oligomer to a binding pair. Hence, this invention also pertains to a method for determining whether or not a combination oligomer binds to a possible binding partner (e.g. an aptmer or target sequence). The method comprises contacting the combination oligomer and the possible binding partner under suitable binding conditions to thereby possibly form a combination oligomer/binding partner complex. According to the method the combination oligomer is a polymer comprising a segment of the formula: A-W-C, wherein A and C are oligomer blocks that are optionally linked to other moieties and that are each independently a peptide nucleic acid, PNA chimera or PNA combination oligomer. The group W is a linker of at least three atoms in length that covalently links oligomer block A to oligomer block C and that is a cleavage site for an enzyme.

According to the method, the binding partner and the combination oligomer are treated with an enzyme suitable for cleaving the cleavage site under suitable enzyme cleaving conditions. Then a determination is made of whether or not the combination oligomer has been cleaved by the activity of the enzyme to thereby determine whether or not the combination oligomer/binding partner complex formed.

Suitable enzyme cleavage conditions are those conditions under which the enzyme operates to act on a substrate. Numerous enzymes are commercially available and generally the product literature of the commercial vendor will provide information on suitable enzyme cleavage conditions. Using available information as well as routine experimentation it will be possible for the ordinary practitioner to determine suitable enzyme cleavage conditions.

According to the method, the enzyme will not substantially cleave the combination oligomer provided that it binds to the binding partner. Thus, binding protects the combination oligomer from substantial degradation by the enzyme. Consequently, the determination of binding is made by analyzing for cleavage products such that if substantial cleavage products are detected, the combination oligomer must not have bound to the potential binding partner.

When the method involves the binding of a combination oligomer to a target sequence, the hybridization will occur under suitable hybridization conditions wherein the combination oligomer hybridizes juxtaposed on the target sequence such that there is no gap. The target sequence can be in higher concentration than the combination oligomer so that essentially all of the available combination oligomer is sequence specifically bound if the target sequence of contiguous nucleobases is present.

Where the binding partner is a target sequence, and the combination oligomer is bound to the target sequence, it is protected from the activity of the enzyme. Accordingly, if the assay determines that the combination oligomer is not substantially degraded, it must have bound to the target sequence (See: Example 4). Conversely, where the combination oligomer was not protected from degradation, it can be concluded that the target sequence was not present. It is also to be understood that since such an assay relies upon an enzymatic event, quantitation of the target sequence can be determined by determining enzyme activity (e.g. measuring enzyme kinetics).

The oligomer blocks of the combination oligomer can all be peptide nucleic acid. The combination oligomer can be labeled or unlabeled, including without limitation, be a self-indicating combination oligomer or otherwise comprise on or more protected or unprotected functional groups. Moreover, the ligation methods described herein can be used for the production of support bound combination oligomers as well as arrays comprising one or more combination oligomers.

Kits of the Invention:

In still another embodiment, this invention pertains to kits. In one embodiment said kit comprises two or more independently detectable combination oligomers wherein each of said independently detectable combination oligomers comprises a first oligomer block and a second oligomer block that are each independently a peptide nucleic acid, a PNA chimera or PNA combination oligomer. The oligomer blocks are linked covalently to each other by a linker that is at least three atoms in length. In each independently detectable combination oligomer, the first and second oligomer blocks taken together encode a probing nucleobase sequence that is designed to sequence specifically hybridize to a target sequence of contiguous nucleobases that is suitable for the formation of a double stranded target sequence/combination oligomer complex. The probing nucleobase sequence in each independently detectable combination oligomer differs from the probing nucleobase sequences of the other independently detectable combination oligomer(s) by at least one nucleobase. Each independently detectable combination oligomer contains at least one independently detectable label. The kit optionally comprises; (i) one or more oligonucleotides; (ii) one or more buffers; (iii) one or more nucleotide triphosphates; (iv) a nucleic acid amplification master mix; or (v) one or more polymerase enzymes. In one embodiment, the kit comprises at least two oligonucleotide primers.

According to the invention, the oligomer blocks of the combination oligomers can all be peptide nucleic acid. The combination oligomers can be labeled or unlabeled, including without limitation, be a self-indicating combination oligomers or otherwise comprise one or more protected or unprotected functional groups. In one embodiment, all of the combination oligomers of the kit are independently detectable, including being independently detectable self-indicating combination oligomers. Optionally, the combination oligomers can comprise a linker comprising a cleavage site for an enzyme. Moreover, the combination oligomers can be support bound or be used in combination with the one or more components of the kit to produce support bound combination oligomers.

As indicated, the kits may optionally comprise one or more additional oligomers, reagents or enzymes. In one embodiment, the one or more additional oligomers are primers suitable for performing a nucleic acid amplification reaction. Exemplary nucleic acid amplification processes have been previously described herein. The kit can also comprise buffers, one or more of nucleotide triphosphates, a polymerase enzyme and/or a nucleic acid amplification master mix, such as those typically used for PCR. In one embodiment, the kit can comprise two or more independently detectable self-indicating combination oligomers and reagents for determining one or more SNPs such as is described in Example 5, below.

Combination Oligomer Sets of the Invention:

In yet another embodiment, this invention pertains to a set of two or more independently detectable combination oligomers. The combination oligomers of the set each comprise a first oligomer block and a second oligomer block that are each independently a peptide nucleic acid, PNA chimera or PNA combination oligomer. The oligomer blocks are linked covalently to each other by a linker that is at least three atoms in length. In each independently detectable combination oligomer, the first and second oligomer blocks taken together encode a probing nucleobase sequence that is designed to sequence specifically hybridize to a target sequence of contiguous nucleobases to thereby form a double stranded target sequence/combination oligomer complex. The probing nucleobase sequence in each independently detectable combination oligomer differs from the probing nucleobase sequences of the other independently detectable combination oligomer(s) of the set by at least one nucleobase. Each independently detectable combination oligomer contains at least one independently detectable label. The set can comprise two or more independently detectable self-indicating combination oligomers wherein each independently detectable combination oligomer comprises at least one energy transfer set of labels such that at least one acceptor moiety of the energy transfer set is linked to one of the linked oligomer blocks of the combination oligomer whilst at least one donor moiety of the energy transfer set is linked to another of the linked oligomer blocks of the combination wherein the labels of the set are linked to the oligomer blocks at positions that facilitate a change in detectable signal of at least one label when the combination oligomer is hybridized to a target sequence as compared to when the combination oligomer is in a non-hybridized state.

According to the invention, the oligomer blocks of the combination oligomers of a set can all be peptide nucleic acid. The combination oligomers of a set can further comprise one or more protected or unprotected functional groups or one or more additional reporter moieties. Additionally, the combination oligomer of a set can comprise a linker comprising a cleavage site for an enzyme. Moreover, the combination oligomers of a set can be support bound or be used in combination with one or more of the components of the kit to produce support bound combination oligomers or arrays of combination oligomers.

Compound Libraries & Methods for their Preparation:

In still another embodiment, this invention pertains to compound libraries. Although it is envisioned that in one respect the invention pertains to one or more compound libraries comprising at least two sets of oligomer blocks (e.g. at least one set of terminal oligomer blocks and at least one set of condensation oligomer blocks), it is also envisioned that terminal oligomer blocks and condensation oligomer blocks can be generated from the same compound library provided that each member of a single set of oligomer blocks (bifunctional single set library of oligomer blocks) is appropriately protected so that depending upon the way the oligomer is pre-treated prior to ligation, it can be used to produce either of the required terminal block or condensation block. Whilst the latter approach can be advantageous because it limits the absolute number of oligomers required for the library, it also adds one or more additional steps to the preparation of the combination oligomers. Accordingly, this invention pertains to both one or more bifunctional single set libraries as well as one or more libraries comprising two or more oligomer block sets.

This invention is also directed to a method for forming a terminal oligomer block and a condensing oligomer block from a bifunctional single set library. The method comprises providing a bifunctional single set library of at least two oligomer blocks. One oligomer block of the bifunctional single set library is treated to thereby remove one or more of the protecting groups to thereby produce a terminal oligomer. One oligomer block of the bifunctional single set library is also treated to remove one or more different protecting groups, as compared with those that produce the terminal oligomer block, to thereby produce a condensing oligomer block.

According to the invention, the various functional groups of the oligomer blocks of the bifunctional single set library can be orthogonal such that they can be selectively removed without deprotecting other groups. Examples of such orthogonal protecting schemes are well known in peptide chemistry, nucleic acid chemistry and PNA chemistry. For example, PNA monomers typically use the acid labile benzhydroloxycarbonyl (Bhoc) to protect the nucleobases of the PNA monomers, whereas the base labile fluorenylmethoxycarbonyl (Fmoc) group is used to protect the amine of the PNA monomers. It is to be understood that the ordinary practitioner will be able to prepare orthogonally protected oligomer blocks suitable for use in the previously described method using no more that routine experimentation.

Thus, this invention is also directed to a compound library comprising a bifunctional single set of oligomer blocks. The oligomer blocks of the set can be used to produce both terminal oligomer blocks and condensation oligomer blocks by the removal of certain protecting groups. The oligomer blocks of the bifunctional set are peptide nucleic acid oligomer, PNA chimera or PNA combination oligomer. The oligomer blocks of the bifunctional set are selected to comprise functional moieties that form a linker of at least three atoms in length when a terminal oligomer block is condensed with a condensation oligomer block. Furthermore, the oligomer blocks are not support bound and do not comprise nucleobase-protecting groups.

In still another embodiment, this invention pertains to another compound library. According the invention, this compound library comprises at least one set of terminal oligomer blocks and at least one set of condensing oligomer blocks wherein each set of blocks comprises two or more different oligomers and said oligomer blocks are selected from the group consisting of: peptide nucleic acid oligomer, PNA chimera and PNA combination oligomer. The oligomer blocks are selected to comprise functional moieties that form a linker of at least three atoms in length when a terminal oligomer block is condensed with a condensation oligomer block. Additionally, the oligomer blocks are not support bound and the oligomer blocks do not comprise nucleobase-protecting groups. It is to be understood that a compound library of this invention is not to be limited to one or two sets of block oligomers. By way of a non-limiting example, the library may comprise three or more sets of oligomer blocks.

Accordingly, in still another embodiment, this invention pertains to another compound library. The compound library comprises at least one set of terminal oligomer blocks and at least two sets of condensing oligomer blocks. According to the invention, each set of oligomer blocks comprises two or more different oligomers and the oligomer blocks of each set are independently peptide nucleic acid oligomer, PNA chimera or PNA combination oligomer. The oligomer blocks are selected to comprise functional moieties that form a linker of at least three atoms in length that covalently links the oligomer blocks when a terminal oligomer block is condensed with a condensation oligomer block. Additionally, the oligomer blocks are not support bound and the oligomer blocks do not comprise nucleobase-protecting groups. Furthermore, all of the oligomer blocks of a set of condensing oligomer blocks contain the same independently detectable reporter moiety wherein different sets of condensation oligomer blocks comprise different independently detectable labels. All of the oligomer blocks of the at least one set of terminal oligomer blocks comprise the same non-fluorescent quencher moiety.

A compound library of this configuration is particularly useful for the production of pairs of independently detectable self-indicating combination oligomers. For example, one terminal oligomer block from each set of independently detectable oligomer blocks can be ligated to the same or different terminal oligomer block comprising the non-fluorescent quencher moiety. Such pairs of independently detectable self-indicating combination oligomers can be used to in SBP analysis. Moreover, the library can be used for generating pairs of combination oligomers for SNP analysis such as is described in Example 5.

It is to be understood that the length of the oligomer blocks of a library is not a limitation. For example, the oligomer blocks of a library can be independently selected to be trimers, tetramers, pentamers, hexamers, heptamers or octamers. Moreover, the oligomer blocks of a set need not be all of the same length, label configuration or the like. The oligomer blocks of a set can comprise both variable and constant regions of nucleobases. It is also to be understood that the oligomer blocks of a library can be support bound. Optionally, the library may itself exist as an array of block oligomers that can be used to form combination oligomers by the process of ligating/condensing one or more oligomer blocks thereto.

According to one embodiment, a terminal oligomer block of a library can be condensed with a condensation oligomer block of the same or another library to thereby form a combination oligomer of desired nucleobase sequence. Accordingly, ligation/condensation of the oligomer blocks of this invention produce a linker that is at least three atoms in length and that links two oligomer blocks. The linker may comprise a cleavage site for an enzyme. Possible linkers have been previously described herein. Non-limiting methods for forming combination oligomers by the ligation/condensation of oligomer blocks have previously been described herein. Such methods can be used in combination with the libraries described herein. It is an advantage that that nucleobases of the oligomer blocks do not need to be protected to be useful in said ligation/condensation processes.

In accordance with this invention, the nucleobase sequence of the terminal oligomer block and nucleobase sequence of the condensing oligomer block can be chosen from the sets of a library, or libraries, of oligomer blocks to thereby enable the rapid, efficient and/or appropriately scaled synthesis of a combination oligomer that is suitable for a chosen application. Thus, the possession of a library, or libraries, of oligomer blocks can facilitate the rapid, efficient and/or appropriately scaled synthesis of numerous combination oligomers of different but known nucleobase sequence, wherein the number of potential combination oligomers of different nucleobase sequence that can possibly be made from a library is determined by the diversity of the terminal oligomer block set and condensing oligomer block set (or the diversity of a single oligomer block set as appropriate) and wherein the diversity of a set will depend on the number of oligomers of different nucleobase sequence in the set.

The diversity of a set of oligomer blocks is determined by the number of possible variables at a position raised to the power of the number of variable sites. For example a set of pentamer blocks, wherein each of the five subunits could be variable and the possible variations included the four natural nucleobases A, C, G & T, would produce an all inclusive set of $4^5=1024$ pentamers. However, some or all of the oligomer blocks of one or both of the terminal oligomer blocks of a set and the condensing oligomer blocks of a set may comprise both a region of constant nucleobase sequence as well as a region of variable nucleobase sequence. Thus, a complete set of oligomer blocks consisting of only the four natural nucleobases A, C, G & T is $4^n$ wherein n is a whole number representing only the number of variable nucleobase positions.

However there is no requirement that a library of this invention comprise a complete set of block oligomers or that the sets of block oligomers of a library, or libraries, all be of the same length or diversity. Thus, in certain embodiments, a library can comprise: 1) oligomer blocks wherein less than all four of the natural nucleobases are present; 2) oligomer blocks wherein all four of the natural nucleobases are present; 3) either of 1) or 2) further comprising one or more non-naturally occurring nucleobases; or 4) oligomer blocks only comprising non-naturally occurring nucleobases.

In fact use of the following non-natural nucleobases is specifically contemplated: 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Binding pair motifs for these nucleobases have also been previously described herein.

In one embodiment, the number of variable positions (variable nucleobase containing subunits) in a set of block oligomers is 3-8 such that the number of oligomers in a complete set (A, C, G & T as the nucleobases) is 64, 256, 1024, 4096, 16384 and 65536, respectively.

In one embodiment, a region of constant nucleobase sequence can be present when the oligomers of the set have a common utility wherein variation is required in only a subsection in order to perform a desired experiment or examination. For example, the constant region can be in the range of 1-10 nucleobase containing subunits.

In one embodiment, the terminal oligomer blocks of a set are peptide nucleic acid oligomers having a C-terminal amide and an N-terminal natural amino acid. For example, the N-terminal amino acid can be selected from the group consisting of: lysine, cystine, glutamic acid and aspartic acid. In another embodiment, the N-terminal natural amino acid is glycine.

In another embodiment, the terminal oligomer blocks of the set are peptide nucleic acids having a C-terminal amide and an N-terminal reactive moiety such as aminooxyacetyl, 2-thioacetyl, 3-thiopropionyl, malimido and haloacetyl and vinyl. See FIGS. 29-31 for an illustration of the operation of these functional groups in view of the ligation/condensation chemistry previously discussed.

In still another embodiment, the set of condensation oligomer blocks are peptide nucleic acids having a C-terminal natural amino acid moiety and a capped or protected N-termini (e.g. labeled). The C-terminal amino acid can be selected from the group consisting of: lysine, cystine, glutamic acid and aspartic acid. In another embodiment, the C-terminal amino acid is glycine.

In still another embodiment, the terminal oligomer blocks of the set are peptide nucleic acids having a capped or protected N-termini and a C-terminal reactive moiety such as N-hydroxysuccinimidyl, haloacetyl or aldehyde moiety or a functional group selected from the group consisting of: chloroacetyl, bromoacetyl iodoacetyl, glycinal and β-alinal. See FIGS. 29-31 for an illustration of the operation of these functional groups in view of the condensation/ligation chemistry discussed previously.

Non-Limiting Examples of the Sets of a Library

A exemplary library can comprise three or more sets of oligomer blocks wherein at least two sets can be substantially identical except for the nature of the label such that the two or more different labeling schemes (one labeling scheme being common to each individual set of oligomer blocks) renders each set of oligomer blocks independently detectable. The two or more independently detectable oligomer block sets may be sets of terminal oligomer blocks or condensation oligomer blocks. By producing, two sets of oligomer blocks that are essentially identical but for the nature of the attached independently detectable label, it is possible to prepare pairs of independently detectable combination oligomers.

According to the invention, at least two oligomer blocks comprising independently detectable labels can be ligated to the same or different oligomer blocks that, for example, are labeled with an acceptor or quencher moiety. For example the label can be a non-fluorescent quencher moiety that is suitable for substantially quenching the detectability of each of the different independently detectable labels such that when oligomer blocks are ligated to form a combination oligomer, pairs of independently detectable self-indicating probes can be formed based upon the nature of the oligomer blocks that are chosen from the libraries for ligation. Example 6 of this specification illustrates the ligation of labeled oligomer blocks to thereby produce pairs of independently detectable combination oligomer probes suitable for use in SNP genotyping.

If the acceptor or quencher moiety is not present on the oligomer block to which the independently detectable blocks are ligated, then the combination oligomers formed by the ligation will be a labeled combination oligomer wherein the choice of labels will be limited only by the diversity of the previously described two or more sets of independently detectably labeled oligomer blocks. It is also noted that the library may optionally comprise both the unlabeled set of oligomer blocks as well as the set of oligomer blocks comprising a linked acceptor or quencher moiety so that depending on the requirements, either a fluorescently labeled independently detectable combination oligomer or a self-indicating combination oligomer can be prepared from the ligation reaction.

In another preferred embodiment, the set described above can further comprise an additional set of unlabeled oligomers that is substantially identical to the sets comprising the independently detectable labels except that they are unlabeled. Hence, when combined, through ligation, with an oligomer from the other set of unlabeled oligomer blocks, a completely unlabeled combination oligomer can be prepared. Such unlabeled oligomers can, for example, be used as blocking probes (See for Example: U.S. Pat. No. 6,110,676), used as capture probes, used as detector probes wherein a labeled antibody is used to detect the hybrid (See for Example: U.S. Pat. No. 5,612,458); or used to produce an array of unlabeled combination oligomers.

TABLE 1

Configuration Of Potential Oligomer Block Sets Of A Library

| Condensation Block Set | Terminal Block Set | Properties of Combination Oligomer/Potential Applications |
|---|---|---|
| Unlabeled | Unlabeled | Unlabeled probe or primer; blocking probe, capture probe or detector probe used in combination with antibody detection methods |
| Unlabeled | Label | Labeled probe or primer |
| Label | Unlabeled | Labeled probe or primer |
| Donor/Acceptor | Donor/Acceptor | Self-Indicating Probe |
| Donor/Acceptor | Unlabeled | Component Polymer of Detection Complex |
| Unlabeled | Donor/Acceptor | Component Polymer of Detection Complex |

In accordance with the prior description, Table 1 summarizes various possibilities for the make up of sets of oligomer blocks of a possible library as well as the properties of the combination oligomers prepared by the ligation thereof. Of course Table 1 is not intended to be exhaustive of possibilities and, as discussed herein, oligomer block sets comprising essential identical oligomers, except for the label attached thereto, can be an important aspect of this invention and will expand the utility of the library. One or more of the sets of oligomer block can also optionally contain protected or unprotected functional groups linked to the oligomer blocks at the termini or linked at a position internal to the oligomer blocks (or when ligated, at a position integral to the linker of the combination oligomer). In this regard, the oligomer blocks can be labeled either pre- or post-ligation, depending on a practitioner's desire and available resources or otherwise the functional groups can be used to attach the oligomer blocks or formed combination oligomers to a surface.

Arrays of Combination Oligomer & Methods for their Preparation:

Arrays comprising nucleic acid, peptide nucleic acid or chimera have been described in the literature. Generally, a nucleic acid or peptide nucleic acid can be immobilized to an array by either synthesizing the oligomer on the support or otherwise by immobilizing the previously formed oligomer. For example, the condensation oligomer blocks can be ligated to one or more of support bound terminal oligomer blocks to thereby form an array of combination oligomers suitable for performing a desired application. Alternatively, a preformed combination oligomer can be reacted at a position of an array to thereby effect the attachment of the combination oligomer.

Because the location and sequence of each support bound oligomer is known, arrays can be used to simultaneously detect, identify and/or quantitate the presence or amount of one or more target sequences in the sample. For example, a target sequence can be captured by the complementary combination oligomer on the array surface and then the probe/target sequence complex is detected. Since the composition of the combination oligomer is known at the location on the surface of the array (because the oligomer was synthesized or attached to this position of the array), the composition of target sequence(s) can be directly detected, identified and/or quantitated by determining the location of detectable signal generated on the array. Thus, arrays may be useful in diagnostic applications or in screening compounds for leads that might exhibit therapeutic utility.

In yet another embodiment, this invention pertains to an array of at least two combination oligomers wherein at least one of the combination oligomers comprises a segment having the formula: A-B-C. According to the invention, oligomer blocks A and C are each independently a peptide nucleic acid, PNA chimera or PNA combination oligomer and are optionally linked to other moieties. The linker B is at least three atoms in length and covalently links oligomer block A to oligomer block C. Oligomer blocks A and C can be unlabeled, labeled with one or more reporter moieties or comprise one or more protected or unprotected functional groups linked thereto. Oligomer blocks A and C taken together encode a probing nucleobase sequence that is designed to sequence specifically hybridize to a target sequence of contiguous nucleobases to thereby form a double stranded target sequence/combination oligomer complex.

In yet another embodiment, this invention pertains to methods for forming an array of combination oligomers. In one embodiment, the method comprises reacting, at a site on a solid carrier, a first oligomer block, a second oligomer block, and optionally a condensation reagent or reagents under condensation conditions to thereby form a combination oligomer having a linker of at least three atoms in length that covalently links the first oligomer block to the second oligomer block. According to the invention, one of said two oligomer blocks is support bound. Further, the first and second oligomer blocks are each independently a peptide nucleic acid oligomer, PNA chimera or PNA combination oligomer. Additionally, one or both oligomer blocks do not comprise nucleobase protecting groups and the combination oligomer forms in the absence of a template. The method further comprises repeating the method with one or more different oligomer blocks at one or more different sites until the desired array of combination oligomers is constructed.

In still another embodiment, this invention pertains to another method for forming an array of combination oligomers. The method comprises reacting, at a site on a solid carrier, a functional group of a combination oligomer having a linker of at least three atoms in length that covalently links the first oligomer block to the second oligomer block with a surface functional group to thereby covalently attach the combination oligomer to the surface. According to the method, the first and second oligomer blocks of the combination oligomer are each independently a peptide nucleic acid oligomer, PNA chimera or PNA combination oligomer. Moreover, one or both oligomer blocks do not comprise nucleobase-protecting groups. The method further comprises repeating the method for attachment of the combination oligomer with one or more different combination oligomers at one or more different sites until the desired array of combination oligomers is constructed.

EXAMPLES

This invention is now illustrated by the following examples that are not intended to be limiting in any way.

General Information on PNA and DNA Synthesis/Oligomers

All PNA Oligomers were prepared from commercial reagents and instrumentation obtained from Applied Biosystems, Foster City, Calif. using manufacturer published procedures, other well-known procedures or those disclosed in published PCT applications WO99/21881, WO99/22018 and WO99/49293.

All nucleic acid (DNA) oligomers, used as target sequence, were prepared from commercial reagents and instrumentation obtained from Applied Biosystems, Foster City, Calif. using manufacturer published procedures or were obtained from commercial vendors of custom oligonucleotides.

Example 1

Evaluation Of Combination Oligomers

Introduction & Purpose

A series of PNA oligomers that contained the same nucleobase sequence (coding for a variable region in the human K-ras gene) but that were either native (unmodified) or else comprising two oligomer blocks centrally linked by various linker moieties (a "combination oligomer") were designed and synthesized for the purpose of evaluating hybridization properties (See: Table 2). The oligomers were synthesized using standard methodologies, without any ligation steps. Critical factors that were evaluated included: 1) whether or not a gap should be present between the oligomer blocks when hybridized to a target sequence; 2) whether or not labels that were attached to the combination oligomers would either: (i) influence hybridization properties; or (ii) effectively function in the manner for which they are typically designed (e.g. would the energy transfer set allow for determination of oligomer hybridization by exhibiting a change in detectable signal as compared with unhybridized oligomer); 3) how do the hybridization properties of the combination oligomers otherwise compare with the native oligomers; and 4) whether or not there is a preferred embodiment for a combination oligomer. In order to evaluate the hybridization properties of the native and combination oligomers, a series of fully of partially complementary nucleic acid (DNA) target sequences were likewise obtained (See: Table 3).

Description of Tables 2 & 3

With reference to Table 2, all of the native and combination oligomers that were evaluated are identified as PNA A through PNA L (column I). The complete sequence of each probe is illustrated in column II. In column III, the particular linker type is identified and in column IV the presence or absence of reporter moieties is identified.

Again with reference to Table 2, the native oligomers are PNA F and PNA L. By native we mean that the nucleobase sequence is continuous without inclusion of a linker that links two backbone subunits of two component oligomer blocks. For this Example, the backbone that is native to the polymer is continuous without interruption. PNA F differs from PNA L in that PNA L is labeled with a fluorophore and quencher moiety as described in WO99/21881 (i.e. it is a self-indicating oligomer probe) but PNA F is unlabeled. It is noted that the oligomers PNA A to PNA E likewise differ from PNA G to PNA K, in this respect. Consequently, PNA A through PNA F differ from PNA G to PNA L only in the absence or presence of reporter moieties, respectively. PNA A to PNA E are combination oligomers comprising different linkers. PNA G to PNA K comprise the same linkers as PNA A to PNA E, respectively.

TABLE 2

Table Of Native & Combination Oligomers Prepared

| I<br>Probe ID | II<br>Sequence | III<br>Linker | IV<br>Label |
|---|---|---|---|
| PNA A | H-ACCAG-X-TCCAA-NH$_2$ | X-linker | No Label |
| PNA B | H-ACCAG-E-TCCAA-NH$_2$ | E-linker | No Label |
| PNA C | H-ACCAG-GlyGly-TCCAA-NH$_2$ | 2 Glycines | No Label |
| PNA D | H-ACCAG-O-TCCAA-NH$_2$ | 1 O-linker | No Label |
| PNA E | H-ACCAG-OO-TCCAA-NH$_2$ | 2 O-linkers | No Label |
| PNA F | H-ACCAGTCCAA-NH$_2$ | No Linker | No Label |
| PNA G | F-Glu-ACCAG-X-TCCAA-K-K-D-NH$_2$ | X-linker | SI |
| PNA H | F-Glu-ACCAG-E-TCCAA-K-K-D-NH$_2$ | E-linker | SI |

TABLE 2-continued

Table Of Native & Combination Oligomers Prepared

| I<br>Probe ID | II<br>Sequence | III<br>Linker | IV<br>Label |
|---|---|---|---|
| PNA I | F-Glu-ACCAG-GlyGly-TCCAA-K-K-D-NH$_2$ | 2 Glycines | SI |
| PNA J | F-Glu-ACCAG-O-TCCAA-K-K-D-NH$_2$ | 1 O-linker | SI |
| PNA K | F-Glu-ACCAG-OO-TCCAA-K-K-D-NH$_2$ | 2 O-linkers | SI |
| PNA L | F-Glu-ACCAGTCCAA-K-K-D-NH$_2$ | No Linker | SI |

For Table 2, all PNA sequences are written from the amine to the carboxyl terminus (left to right) in accordance with convention used for the illustration of peptide sequences. Other abbreviations are: F = 5-(6)-carboxyfluorescein, D = 4-((4-(dimethylamino)phenyl)azo)benzoic acid (dabcyl), O or O-linker = 8-amino-3,6-dioxaoctanoic acid; K = the amino acid L-Lysine, Glu = the amino acid L-glutamic acid, Gly = the amino acid E or E-linker = the moiety referred to as "E" in U.S. Pat. No. 6,326,479 and X or X-linker = the moiety referred to as "+" in U.S. Pat. No. 6,326,479; SI = self-indicating.

With reference to Table 3, the nucleobase sequence of several nucleic acid target sequences (possible binding partners) that potentially bind to the native and combination oligomers of Table 2 are illustrated. The different nucleic acid oligomers are identified in column I. The nucleotide sequence of the different nucleic acid oligomers is identified in column II. A description of the nature of the nucleobase sequence is provided in column III. Column IV merely denotes the assigned Seq. Id. No.

Nucleic acid oligomers DNA P and DNA Q differ by inclusion of the italicized and underlined G residue (DNA P). This residue represents the "gap base" or "gap" that is designed to be present when the native and combination oligomers are allowed to hybridize to the target sequences. However, because this gap base is not present when the native and combination oligomers hybridize to nucleic acid oligomers DNA Q-V, there is no "gap" (See FIG. 1). Nucleic acid oligomer DNA Q represents the perfect complement to the native and combination oligomers of Table 1. Nucleic acid oligomers DNA R-T comprise a mismatch (highlighted in bold text) as compared with the perfectly complementary oligomer DNA Q, wherein the mismatch is centrally located with respect to one of the 5-mer oligomer blocks. Nucleic acid oligomers DNA U and DNA V comprise a mismatch (highlighted in bold text) as compared with the perfectly complementary oligomer DNA Q, wherein the mismatch is not centrally located with respect to one of the 5-mer oligomer blocks.

TABLE 3

Table Of Target Sequences

| I<br>Oligo<br>ID | II<br>Sequence | III<br>Description | IV<br>Seq.<br>ID No. |
|---|---|---|---|
| DNA P | TAGTTGGAGCTGGTGGC | Match with gap | 1 |
| DNA Q | TAGTTGGACTGGTGGC | Match contiguous | 2 |
| DNA R | TAGTTGGACTTGTGGC | MisMatch contiguous | 3 |
| DNA S | TAGTTGGACTAGTGGC | MisMatch contiguous | 4 |
| DNA T | TAGTTGGACTCGTGGC | MisMatch contiguous | 5 |
| DNA U | TAGTTGGACGGGTGGC | MisMatch contiguous | 6 |
| DNA V | TAGTTGGAGTGGTGGC | MisMatch contiguous | 7 |

Tm Experiments with Combination Oligomers Hybridized to the Nucleic Acid Target Sequences In a thermal melting experiment, a hybrid between two polymer strands is, by heating, melted into its component oligomers. The temperature at which the dissociation of the hybrid occurs is a function of thermodynamic properties that are characteristic of that particular hybrid. The temperature at which half of the hybrids remain double stranded, with the remaining half existing as single strands, is commonly referred to as the Tm of the hybrid.

In order to perform the Tm experiments, samples were prepared by mixing 0.5 μM of each of the native or combination oligomers (Table 2) with certain of the nucleic acid target sequences (Table 3) in 2.5 mL Tm Buffer (100 mM sodium chloride, 10 mM potassium phosphate, pH 7.1) in quartz cuvettes. The native and combination oligomers were also tested in the absence of target sequences ("No DNA" control) as a means to determine whether or not the combination oligomers were self-annealing or self-complementary. In no case was there a Tm in the absence of a target sequence, thereby indicating that the native and combination polymers do not self-anneal or self-hybridize. The Tm analyses were performed using the Cary 100 spectrometer, using the "Thermal" program supplied by the instrument manufacturer (Varian). All absorbance measurements were recorded with reference to a blank containing buffer. All analyses were performed in dual beam mode.

Prior to each measurement, samples were denatured by heating to 95° C. for 2 minutes, then cooled to 25° C. For all Tm determinations, the samples were heated and then cooled at a rate of 0.5 degrees per minute. The beginning and end points for each melt were determined empirically prior to each run, depending upon the Tm observed during the pre-melt. Throughout the experiments, absorbance data were recorded at 0.5 degree increments. The Tm values were then calculated using instrument software and a moving average taken over 10.5 degrees (corresponding to 21 data points at 1 point per 0.5 degree). The Tm data for various experiments are displayed in Tables 4 and 5. All Tm values presented are the average of the values obtained from the heating and cooling steps.

Discussion of Data Table 4; Determining Optimal Probe Design

TABLE 4

Table Of Tms For Determining Optimal Probe Design

| I<br>Probe ID | II<br>DNA P | III<br>DNA Q | IV<br>Δ Tm P − Q |
|---|---|---|---|
| PNA A | 29.0 | 37.4 | 8.3 |
| PNA B | 30.9 | 37.3 | 6.4 |
| PNA C | 25.2 | 41.5 | 16.3 |
| PNA D | 23.3 | 40.3 | 17.0 |
| PNA E | 21.2 | 36.1 | 14.9 |
| PNA F | 35.2 | 53.1 | 17.9 |
| PNA G | 30.4 | 37.1 | 6.7 |
| PNA H | 30.5 | 37.1 | 6.6 |
| PNA I | 23.6 | 41.8 | 18.2 |
| PNA J | 23.1 | 40.2 | 17.1 |
| PNA K | 19.6 | 36.1 | 16.5 |
| PNA L | 38.8 | 53.2 | 14.4 |

Table 4 summarizes Tm data for the hybridization of all of native and combination oligomers PNA A to PNA L with either of the gap or no gap nucleic acid target sequences DNA P and DNA Q, respectively (See: FIG. 1). With reference to Table 4, the native or combination oligomer used to determine the Tm is identified in column I. In column II, the Tm (° C.) for all hybrids formed with nucleic acid target sequence DNA P is recorded. In column III, the Tm for all hybrids formed with nucleic acid target sequence DNA Q is recorded. In column IV, the difference in Tm (ΔTm P-Q in ° C.) is recorded for hybrids using DNA P vs. DNA Q, respectively.

Again with reference to Table 4, for every hybrid the Tm value is greater if DNA Q is used as compared with DNA P. The absolute difference in Tm for a native or combination oligomer is found in column IV. Because the difference between DNA P and DNA Q is the presence or absence of a gap, respectively, it is clear that the more stable hybrid is always formed when the block oligomers hybridize juxtaposed to the target sequence such that there is no gap. Moreover, the substantial difference in Tm (6.4 to 17.9° C.) indicates that this is a substantially preferred hybrid as compared with hybrids comprising a gap.

Again with reference to Table 4, it is clear that the data for PNA A to PNA F is substantially the same as for PNA G to PNA L, respectively. The strong similarity in data for each unlabeled PNA as compared with the equivalent labeled PNA indicates that the labels do not substantially affect the hybridization properties of the various native and combination oligomers.

Discussion of Data Table 5; Determining Probe Discrimination/Selectivity

Because PNA C appeared to have the most preferred linker, we selected the combination oligomer PNA C for further comparison with the native oligomer PNA F. Table 5 summarizes Tm data for the hybridization of each of PNA C and PNA F with each of the nucleic acid target sequences DNA Q to DNAV; wherein in all cases the hybrid comprises no gap. With reference to Table 5, the nucleic acid target sequence used to determine the Tm is identified in column I. In column II, the Tm (° C.) for all hybrids formed with PNA C is recorded. In column III, the Tm for all hybrids formed with PNA F is recorded. In column IV, the difference in Tm (ΔTm in ° C.) for the hybridization between the perfect complement (DNA Q to PNA C) and the Tm recorded for a particular nucleic acid target comprising a mismatch (point mutation of single nucleotide polymorphism) and PNA C is recorded. In column V, the difference in Tm (ΔTm in ° C.) for the hybridization between the perfect complement (DNA Q to PNA F) and the Tm recorded for a particular nucleic acid target comprising a mismatch (point mutation of single nucleotide polymorphism) and PNA F is recorded. In column VI, the absolute difference in the values in column IV as compared to column V (ΔC-ΔF), is recorded.

TABLE 5

Table Of Tms For Determining Probe Discrimination/Selectivity

| I | II<br>PNA C | III<br>PNA F | IV<br>ΔC | V<br>ΔF | VI<br>ΔC − ΔF |
|---|---|---|---|---|---|
| DNA Q | 41.5 | 53.1 | — | — | 0.0 |
| DNA R | 21.0 | 34.0 | 20.5 | 19.1 | 1.3 |
| DNA S | 19.7 | 36.0 | 21.8 | 17.1 | 4.7 |
| DNA T | 19.5 | 35.0 | 22.0 | 18.1 | 3.9 |
| DNA U | 20.3 | 35.0 | 21.2 | 18.1 | 3.1 |
| DNA V | 21.8 | 32.0 | 19.7 | 21.1 | −1.4 |

Because the only perfectly complementary hybrid is formed using DNA Q, all data for each different PNA hybridizing to a mismatch containing nucleic acid target sequence is compared with DNA Q. This is why there is no data in columns IV to VI for DNA Q.

With reference to column IV of Table 5, the ΔC value for DNA R to DNA T is 20.5-22.0° C. This indicates that a mismatch centrally located in one of the block oligomers of the combination oligomer imparts a substantial destabilization effect to the hybrid. By comparison, the ΔF value for DNA R to DNA T is 17.1-19.1° C. (See column V). This indicates that a mismatch in the same position of a hybrid formed from a native oligomer and a target sequence imparts a lesser destabilization effect as compared with the most nearly equivalent hybrid formed using a combination oligomer (having a gly-gly dimer linker; See column VI) and a target sequence. Although there is clearly a small difference in ΔTm that occurs as a result of the nature of the particular nucleobase forming the mismatch, the data includes all possible natural mismatch combinations. The data indicates that in all cases, the destabilizing effect is greater for the combination oligomer as compared with the native oligomer (See column VI).

With reference to column IV of Table 5, the ΔC value for DNA U is 21.2° C. By comparison, the ΔF value for DNA U is 18.1° C. (See column V). This indicates that a mismatch located non-centrally in one of the block oligomers of the combination oligomer imparts a substantial destabilization effect to the hybrid that is again more significant as compared with the destabilizing effect resulting from the inclusion of the same mismatch in a hybrid using a native oligomer and the same target sequence (See column VI). This data suggests that the mismatch need not be centrally located within the oligomer block of the combination oligomer in order to achieve a benefit in discrimination/selectivity as compared with a native oligomer.

With reference to column IV of Table 5, the ΔC value for DNA V is 19.7° C. By comparison, the ΔF value for DNA U is 21.1° C. (See column V). This indicates that a mismatch located at the termini of one of the block oligomers of the combination oligomer imparts a lesser destabilization effect to the hybrid as compared with the destabilizing effect resulting from the inclusion of the same mismatch in a hybrid using a native oligomer and the same target sequence (See column VI). This data suggests that the mismatch located at the terminus of the oligomer block of the combination oligomer does not result in improved discrimination/selectivity as compared with a native oligomer.

Fluorescence Experiments with Self-Indicating Combination Oligomers

In order to evaluate whether or not the self-indicating combination oligomers (PNA G through L), could operate in the manner expected (based upon the label configuration), they were hybridized to the complementary nucleic acid, DNA Q, and the resulting fluorescence of each sample was measured.

The self-indicating combination oligomers were diluted to a final concentration of 1.0 µM in 100 µL of Tm Buffer and placed into individual wells of a 96 well polyethylene microtitre plate. The fluorescence of each self-indicating combination oligomer was then determined using a Wallac Victor fluorescent plate reader, using a filter set that is optimized for detecting the fluorescence of fluorescein. After recording this baseline value for each self-indicating combination oligomer, a 3 µL aliquot containing 35 µM DNA Q was added to each well thereby resulting in a final concentration of 1.0 µM. The sample in each well was then mixed and hybridization was allowed to proceed for 10 minutes. As a control, a non-complementary target was added in a similar way to another complete set of self-indicating combination oligomers. In every case, the fluorescent value for each self-indicating combination oligomer increased significantly when the complementary DNA was added but did not appreciably increase in the presence of the non-complementary DNA.

Summary

In summary, the data supports the following conclusions: 1) it is preferable that there be no gap between the oligomer blocks when hybridized to a target sequence since this embodiment results in the most stable hybrid and there is an improved selectivity/discrimination observed for such oligomers; 2) when labels are attached to the combination oligomers they do not appear to either: (i) substantially influence hybridization properties; or (ii) function in the manner that differs from that which they are typically designed; 3) although the Tm of combination oligomers tend to be lower than the native oligomers, the combination oligomer can be designed to exhibit a significantly enhanced selectivity/discrimination as compared with the native oligomers; and 4) the most preferred embodiment for a combination oligomer appears to be an oligomer comprising a amino acid dimer, and in particular the gly-gly dimer.

Example 2

Block Ligation in the Absence of a Template

Introduction & Purpose

The preceding example indicated that combination oligomers could be useful in hybridization reactions used, for example, to detect a target nucleic acid sequence. In this Example, the goal was to determine whether or not it would be possible to efficiently ligate two oligomer blocks in the absence of a template (i.e. non-template directed ligation) to thereby form a combination oligomer. The ligation reaction was intended to produce a gly-gly dimer linker.

Reagent Solutions:
  0.5M 2-(N-Morpholino)ethane sulfonic acid (MES) Buffer; pH 4.5
  HOAt Solution: prepared by mixing 21.4 mg of 1-Hydroxy-7-azabenzotriazole (HOAt) with 2 mL of 1:1, N,N'-dimethylformamide (DMF): 0.5M MES Buffer pH 4.5.
  EDC Solution was prepared by adding 10 mg 1-Ethyl-3-(3-Dimethylamino-propyl)carbodiimide hydrochloride (EDC) to 100 µL of 0.5 M MES Buffer (this solution should be prepared immediately before use).
  Quenching Solution was prepared by adding 10 mg of Glycinamide-HCl to 100 µL of 1M sodium bicarbonate solution (unbuffered).

General Reaction Conditions:

Final reaction conditions are generally 10 equivalents of HOAt and 500 equivalents of EDC in a reaction mixture that was 750 µM in each oligomer block to be ligated. It is noted that in these experiments, no template was used.

Experiment One:

About 19.1 nmol of each PNA oligomer (the oligomer blocks to be ligated) was added to a single 0.5 mL microcentrifuge tube and subsequently dried. To the dried PNA oligomer mixture was added 4.8 µL of 1:1 DMF:water. This solution was mixed by vortex and then 2.43 µL of HOAt Solution and 18.3 µL of EDC Solution was added. After 5 min, 10 µL of the reaction mixture was removed and quenched with 10 µL of the Quenching Solution. The product was then analyzed by Maldi-TOF mass spectrometry and HPLC. After one hour, 10 µL of the remaining reaction mixture was quenched in the same way and analyzed by Maldi-TOF mass spectrometry and HPLC. The remaining 5.5 µL of the reaction mixture was quenched with 30% aqueous ammonium hydroxide and analyzed by Maldi-TOF mass spectrometry and HPLC.

Experiment Two:

About 95.6 nmol of each PNA oligomer (the oligomer blocks to be ligated) was added to a single 0.5 mL eppendorf tube and subsequently dried. To the dried PNA oligomer was added 23.7 µL of 1:1 DMF:water. The solution was mixed by vortex and then 12.2 µL of HOAt Solution was added followed by the addition of 91.6 µL of EDC Solution. The reaction was quenched after one hour with 127.5 µL of Quenching Solution. The product was then analyzed by Maldi-TOF mass spectrometry and HPLC.

Results:

TABLE 6

Table Of Ligation Results

| Experiment # | % Product (5 min.) | % Product (1 hour) |
|---|---|---|
| 1 | 71.9 | 82 |
| 2 | No Data | 85 |

For both experiments the condensing block was capped with an acetyl moiety. Specifically, the condensing block (PNA) was Ac-ACC-AG-Gly-COOH and the terminal block was H-Gly-TCC-AA-NH$_2$ wherein Ac represents the acetyl cap, Gly represents that amino acid glycine and other abbreviations are well known in the field of peptide chemistry.

With reference to Table 6, the percent completion of the ligation reaction was measured based on the integration of peak area (excluding the peak representing the HOAt) of the HPLC analysis of the product. The results demonstrated that the two PNA oligomer blocks can, in the absence of a template, be successfully ligated in greater than 70% yield within 5 minutes but also show that a longer reaction time will lead to a greater percentage of product formation. The reaction occurring as experiment number two (Table 6) was not analyzed at 5 min so that the product could be purified by preparative HPLC. Nevertheless, the results demonstrate that two PNA oligomer blocks, one with a N-terminal glycine comprising a free N-terminal amine group and the other comprising a C-terminal glycine having a carboxylic acid functional group can be ligated rapidly and efficiently with a mixture of HOAt and EDC to thereby produce an unmodified gly-gly dimer that links the two PNA oligomer blocks. The product of the ligation reaction was Ac-ACC-AG-gly-gly-TCC-AA-NH$_2$. This was confirmed by Maldi-TOF mass spectrometry analysis of the final product.

Example 3

PNA-FISH

Introduction & Purpose

Prior experiments performed by Applicants have determined that certain probes will not definitively distinguish single point mutations in functional assays. For example, the PNA oligomer Flu-1 will not definitively distinguish between *S. enterica* (of which *S. cholerasuis* is a serovar) and *S. bongori*, despite the presence of a single point mutation (single nucleotide polymorphism or SNP) that exists in the rRNA of these two organisms.

TABLE 7

Table Of Combination Oligomers & Probes

| Probe ID | PNA Probe Sequence | S/N |
|---|---|---|
| Flu-1 | F-OEE-ACC-TAC-GTG-TCA-GCG-EE-NH$_2$ | 2.1 |
| Flu-2 | F-OEE-TAC-GTG-TCA-GCG-TG-EE-NH$_2$ | 5.3 |
| Flu-3 | F-OEE-TAC-GTG-T-O-CAG-CGT-G-EE-NH$_2$ | — |
| Flu-4 | F-OEE-TAC-GTG-T-Gly-Gly-CAG-CGT-G-EE-NH$_2$ | — |

All abbreviations are as previously defined (See Table 2). The position of the mismatch (single point mutation) in the rRNA or the *Salmonella* species to be distinguished in this assay are in bold text. Signal to noise ratios were obtained using an average based on single from 8 bacteria.

PNA-FISH Procedure:

Individual 3 mL cultures of bacteria were grown overnight in Tryptic Soy Broth (TSB) at 30° C. The broth was then analyzed for absorbance at 600 nm and then diluted into fresh TSB until the absorbance at 600 nm was 0.5 OD/mL. These diluted culture stocks were then allowed to double 3-4 times before harvesting. Cells from a 20 mL culture were pelleted by centrifugation at 10,000 rpm for 5 minutes, resuspended in 20 mL PBS, pelleted again and resuspended in Fixation Buffer (4% paraformaldehyde in PBS (7 mM Na$_2$HPO$_4$; 3 mM NaH$_2$PO$_4$; 130 mM NaCl)). The bacteria were incubated at room temperature for 30-60 minutes before they were pelleted again (centrifugation at 10,000 rpm for 5 minutes). After removal of the fixation solution, the cells were resuspended in 20 mL of 50% aqueous ethanol. The fixed bacteria were then used after 30 minutes of incubation or optionally stored at −20° C. for up to several weeks before being used in an experiment.

For each sample prepared, 100 μL of fixed cells in 50% aqueous ethanol was removed and centrifuged at 10,000 R.P.M. for 2 min. The ethanol was then remove from the sample and the pellet was resuspended in 100 μL of sterile PBS and pelleted again by centrifugation at 10,000 rpm for 2 min.

The PBS was then removed from the pellet, and the cells were resuspended in 100 μL of hybridization buffer (20 mM Tris-HCl, pH 9.0; 100 mM NaCl; 0.5% SDS) that contained the appropriate probe (e.g. Flu-1 though Flu-4) at a concentration of 40 pmol/mL. The hybridization was performed at 55° C. for 30 minutes.

The sample was then centrifuged at 10,000 R.P.M. for 2 min. The hybridization buffer was removed and the cells resuspended in 500 μL sterile TE-9.0 (10 mM Tris-HCl, pH 9.0; 1 mM EDTA). The solution was allowed to stand at 55° C. for 5 minutes. The sample was then centrifuged at 10,000 rpm for 5 minutes. The TE-9.0 was then removed from the pellet. The TE-9.0 wash was then repeated two more times.

After the final wash the cells were resuspended in 100 μL PBS. An aliquot of 2 μL of this suspension of cells was placed on a glass slide, spread and allowed to dry. Next, 1-2 μL of Vectashield (Vector Laboratories, P/NH-1000) and DAPI counterstain was deposited over the dried cells. A coverslip was added to the slide and its position fixed using a couple of drops of nail polish. Each of the two different bacterial strains, *Salmonella cholerasuis* and *Salmonella bongori*, were fixed and hybridized with each of probes Flu-1 through Flu-4 following the protocol described above. After hybridization and wash, each strain was spotted and mounted on a microscope slide (see above) and examined using a Nikon fluorescent microscope equipped with a 60× immersion oil objective, a 10× ocular (total enlargement is 600 fold), and an Omega Optical XF22 filter.

Results

The panels in FIG. 2 are color images taken with a CCD camera equipped microscope using a two second exposure time. With reference to FIG. 2, panels A1-D1 are images taken of a PNA-FISH experiment using *S. cholerasuis* (a serovar of *S. enterica*) and the PNA probes or combination oligomers Flu-1 to Flu-4, respectively. Similarly, panels A2-D2 are images taken of a PNA-FISH experiment using *S. bongori* and the PNA probes or combination oligomers Flu-1 to Flu-4, respectively.

With reference to FIG. 2, a comparison of panels A1 and A2 indicates that although the signal for *S. cholerasuis* is quite strong, the *S. bongori* is likewise detectable, albeit not as intensely positive. Therefore, this result indicates that the probe Flu-1 is not as highly discriminating as would be desirable despite there being a single point mutation in the rRNA of the two *Salmonella* species. In addition to the digital images, a signal to noise ratio was scored at 2.1 (Table 7).

With the probe Flu-2, the positioning of the mismatch was relocated to be more terminally located as compared with being centrally located. The probe was also reduced in size from a 15-mer to a 14-mer (nucleobase sequence). With reference to Panels B1 and B2, it is evident that again the signal for the *S. cholerasuis* is quite strong, while the signal for *S. bongori* is weaker, albeit still detectable. In addition to the digital images, a signal to noise ratio was scored at 5.3 (Table 7). Taken together, the data indicates that moving the mismatch to a more terminal position improves the discrimination of the assay.

The combination oligomers Flu-3 and Flu-4 utilize the same positioning of the mismatch as did Flu-2, and differ from each other only in the nature, but not the position, of the linker; the combination oligomer Flu-3 having a single O-linker bridge whereas the combination oligomer Flu-4 has the preferred gly-gly dimer bridge. With reference to panels C1 and C2 in combination with D1 and D2, it is clear that although the signal is weaker, under identical conditions, with the combination oligomers (Flu-3 and Flu-4), the level of discrimination has improved as compared with the native oligomer probe, Flu-2. Moreover, the signal to noise level was so high, it could not be determined since there was no visible non-specific signal (noise) to count, and dividing by zero would be meaningless.

Summary:

The discrimination between *S. enterica* serovar *cholerasuis* and *S. bongori* was greater with probes Flu-2, Flu-3 and Flu-4. Generally, the probes Flu-2, Flu-3 and Flu-4 exhibited an excellent discrimination between the two species of *Salmonella*. However, by introducing the use of a combination oligomer (e.g. Flu-3 and Flu-4). even greater single point mutation discrimination was possible as compared with native oligomers. Thus, the results demonstrate that the combination oligomers act in a more binary fashion (either hybridized or unhybridized) as compared with native oligomers.

Example 4

Cleavage Assay

Introduction & Purpose:

This experiment was performed to determine whether or not a combination oligomer comprising a cleavage site that was a substrate for an enzyme would be more or less apt to be cleaved by the operation of the enzyme depending on whether or not is was bound to a binding partner. A combination oligomer labeled as a Linear Beacon was used since it was envisioned that both hybridization and cleavage data could be determined.

Materials:

The following PNA combination oligomers were synthesized using commercially available reagents and instrumentation (Applied Biosystems, Foster City, Calif.). These probes were designed to have low fluorescence in the unhybridized state, medium fluorescence in the hybridized state and greatest fluorescence in the cleaved state.

```
PNA-Glu:  F-O-ACCAG-Gly-Glu-TCCAA-K(D)

PNA-Lys:  F-O-ACCAG-Gly-Lys-TCCAA-K(D)
```

(abbreviations have been previously defined; see Table 1)

The probes were purified by reversed-phase chromatography, and product fractions were identified by MALDI-TOF mass spectrometry, product fractions were combined and lyophilized. The dried material was dissolved in 50% aqueous DMF at a concentration of ~50 AU 260 units per mL.

An oligonucleotide target, DNA Q of Example 1, was obtained from Sigma Genosys (Woodlands, Tex.) dissolved in water at a concentration of 365 µM. Proteases were purchased from Roche Biochemicals, (Indianapolis, Ind.) and were formulated as follows:

Glu-C (Roche Cat. No. 1 420 399) was dissolved in Glu-C Buffer at a concentration of 0.1 µg/mL. Glu-C Buffer was 25 mM ammonium carbonate, pH 7.8, containing 5% v/v acetonitrile.

Lys-C (Roche Cat. No. 1 420 429) was dissolved in Lys-C Buffer at a concentration of 0.1 µg/µL. Lys-C Buffer was 25 mM Tris-HCl, 1 mM EDTA, pH 8.5, containing 5% v/v acetonitrile.

Trypsin (Roche Cat. No. 1418 475) was dissolved in Trypsin Buffer at a concentration of 0.1 µg/µL. Trypsin Buffer was 100 mM Tris-HCl, pH 8.5, containing 5% v/v acetonitrile.

Methods:

Reactions were set up in a microtiter plate as follows:

PNA-Glu was diluted 1:2000 in Glu-C buffer. To 100 µL aliquots of this solution in the wells of a microtiter plate was added:

PNA-Glu only
One µL of DNA Q
Two µL of Glu-C protease
One µl of DNA R, two µL of Glu-C protease The timing and order of addition was firstly PNA-Glu in Glu-C Buffer (all wells A through D), followed by DNA Q (wells B and D), then a five minute wait, then Glu-C protease (wells C and D). After each addition reactions were mixed thoroughly. Reaction fluorescence was then measured at 520 nm using a Wallac Victor plate reader (Wallac Oy, Turku Finland). Fluorescence was measured at time zero (after last addition) and two hours later.

Identical reactions were set up for PNA-Lys except that Lys-C Buffer and Trypsin Buffer was substituted for Glu-C Buffer, and Lys-C and Trypsin proteases were substituted for Glu-C protease, respectively.

Figure 3:
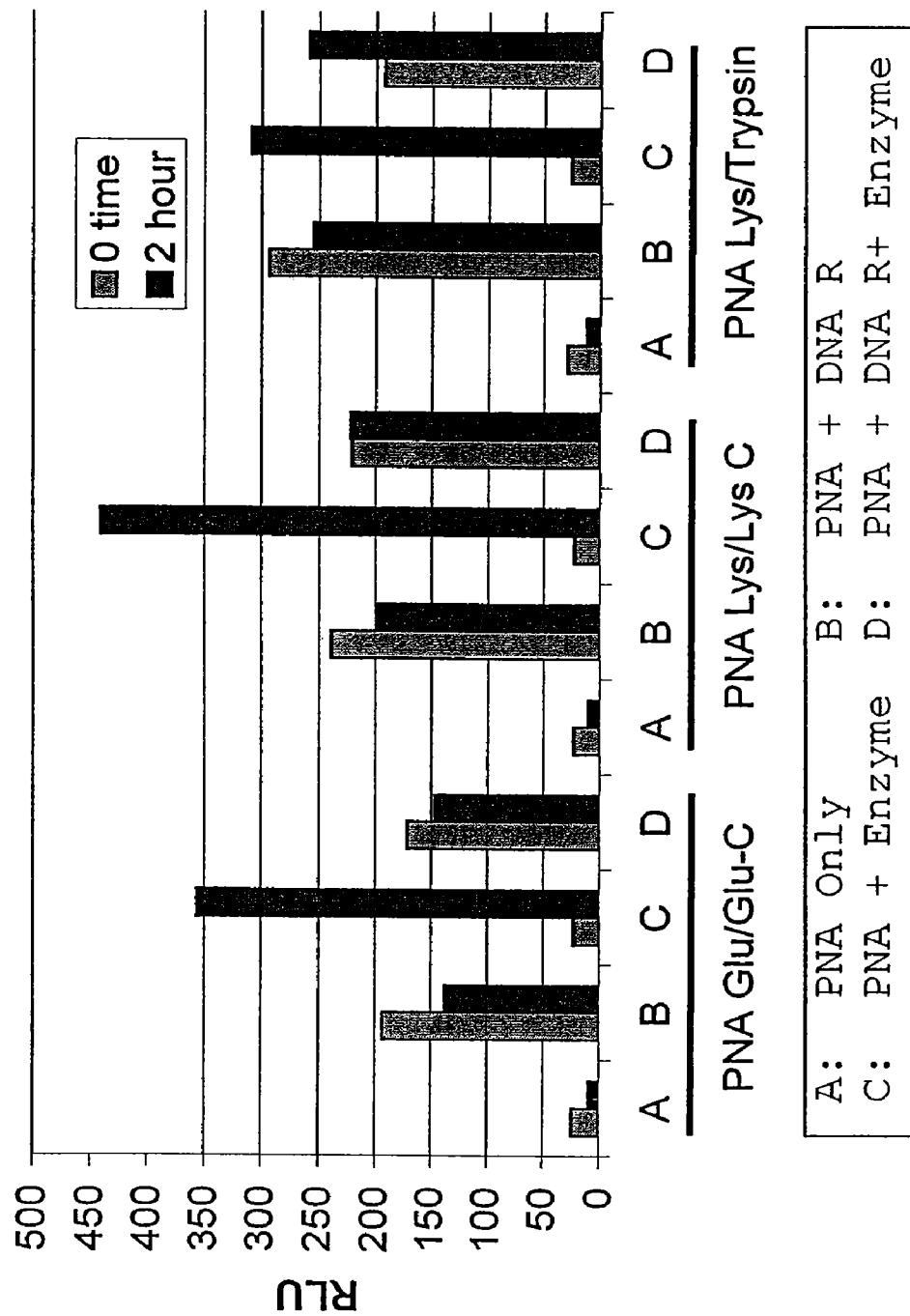
FIG. 3 is a graphical representation of data associated with the enzyme cleavage assay of Example 4.

Results:

The results are graphically illustrated in FIG. 3. In the absence of DNA target each protease was able to hydrolyze its respective PNA substrate (compare A and C in each set) whereas in the presence of target (DNA Q) the PNA was protected from digestion by the proteases (compare B and D in each set). Thus, the ability to discriminate between hybridized and unhybridized PNA combination oligomer with a protease was established since the enzyme cleaved the cleavage site only if the combination oligomer was not bound to the target sequence.

Example 5

SNP Scoring Using Independently Detectable Self-Indicating Combination Oligomers and End-Point Analysis Materials And Methods SNP selection. Information regarding SNP targets, human genomic sequence information, human genomic DNA samples, PCR primer designs, and SNP test results obtained via the TaqMan Assay (Applied Biosystems, Foster City, Calif.) were provided by the Whitehead Institute (Cambridge, Mass.). In view of the information provided, nine SNP targets, designated as 6874, 6802, 6806, 6834, 6837, 6848, 6876, 6879, and 6885, were chosen for evaluation.

DNA samples. The CEPH/Utah Pedigrees 1331, 1333, and 1341 (hereinafter "Coriell Pedigree" or "Pedigree"), consisting of purified, human genomic DNA samples of related individuals, were purchased from Coriell Institute for Medical Research (Camden, N.J.). Pedigree 1331 contained 17 DNA samples designated as F01, M02, D03, S04, D05, D06, D07, D08, S09, S10, S11, FF12, FM13, MF14, MM15, D16, and S17. Pedigree 1333 contained 15 DNA samples designated as F01, M02, S03, S04, S05, D06, S07, S08, S09, S10, FF11, FM12, MF13, MM14, and D15. Pedigree 1341 contained 14 DNA samples designated as F01, M02, D03, D04, D05, D06, S07, D08, D09, S10, FF11, FM12, MF13, and MM14. The DNA samples, as supplied by the Coriell Institute, were diluted to 25 ng/µL in Millipore Milli-Q water (Bedford, Mass.) and stored at 4° C.

PCR primers. The PCR primer designs offered by the Whitehead Institute were all modified by sequence deletion, sequence addition, and/or addition of guanine and/or cytosine bases at the 5' end. Modification of the primers was performed so that unequal Tm values, of approximately 66° C. and 80° C. for the two primers of the set as predicted at 200 nM concentration, were obtained so that the PCR protocol produced both double stranded and single stranded DNA amplicons with lower and higher annealing temperatures, respectively. The Tm predictions for primer design were performed using proprietary software based upon DNA nearest-neighbor parameters for predicting duplex stability as published by SantaLucia et al. *Biochemistry* 35: 3555-3562 (1996).

Once designed, all primers were purchased from Sigma Genosys (The Woodlands, Tex.). The primers, as received from Sigma Genosys, were diluted to approximately 200 µM in 1× TE, pH 8.0 (10 mM Tris, pH 8.0; 1 mM EDTA) and stored at 4° C. One M Tris, pH 8.0 and EDTA disodium salt, dihydrate (used to make the storage buffers), were purchased from Sigma (St. Louis, Mo.) and EM Science (Gibbstown, N.J.), respectively. Properties of the nine primer sets are described in Table 8.

TABLE 8

Oligonucleotide PCR Primer Sets For SNP Analysis

| SNP | Name | Length (bases) | Predicted Tm (° C.) | Sequence | Seq. Id No. |
|---|---|---|---|---|---|
| 6784 | 6784-5 | 24 | 67.1 | ACAAGTCTGGAGTGAGC | 8 |
|  | 6784-3 | 33 | 81.1 | GCGTGGCAGAGATCCCTGTTGC | 9 |
| 6802 | 6802-5 | 22 | 81.0 | GCCTCTGCAGGGTGCTGTCTTG | 10 |
|  | 6802-3 | 19 | 67.3 | AAATGTTGGCTGCCAACTA | 11 |
| 6806 | 6806-5 | 17 | 66.9 | CTTGGAGCATCGAGACT | 12 |
|  | 6806-3 | 22 | 80.1 | GCGTGGCCTGTTTGGAGGTCAA | 13 |
| 6834 | 6834-5 | 16 | 66.2 | GAGGAGTGGTGCTGAT | 14 |
|  | 6834-3 | 25 | 80.3 | GCGGAGGCCATAGCAGAAGAGAAGA | 15 |
| 6837 | 6837-5 | 23 | 66.6 | CCAAGATCTCCAAGTAAAATAAC | 16 |
|  | 6837-3 | 31 | 79.4 | CGCGCCAATAAATGTAAATGGCACAAATCCA | 17 |
| 6848 | 6848-5 | 20 | 65.7 | CCTCATCCAGATAATGTTGT | 18 |
|  | 6848-3 | 33 | 78.8 | GCGCGCAAGAAAATGAATTTTGGCATAAAAACT | 19 |
| 6876 | 6876-5 | 16 | 66.4 | TTCCTCAGCAACCCTG | 20 |
|  | 6876-3 | 24 | 79.8 | GCATAGTGGACCCCAAGTCACCAT | 21 |
| 6879 | 6879-5 | 24 | 65.8 | GGAAATTGAATTTACCTTTTCATT | 22 |
|  | 6879-3 | 33 | 79.8 | GGCGACATTCAAGTTGGAATAGTTCTGAGAGTA | 23 |
| 6885 | 6885-5 | 24 | 79.7 | GGCCAGGACCTGTTTGTGACATGA | 24 |
|  | 6885-3 | 22 | 67.3 | TTTGCTCAATGTGAAATGTTGT | 25 |

PNA probes. All PNA oligomers were synthesized using commercially available reagents and instrumentation except for labeling reagents and/or linkers, which were either supplied by Applied Biosystems or else prepared as described elsewhere (See: U.S. Pat. No. 6,355,421 based on application Ser. No. 09/179,289; herein incorporated by reference). The PNA probes were of design "Dye-NNNNN-Gly-Gly-NNNNN-Lys(Dabcyl)" where the dye was either fluorescein (Flu), (Tam short for Tamra)), Dye1, or Dye2 (the structure of Dye1 & Dye 2 are illustrated in FIG. 33; Dye 2 is also described in U.S. Pat. No. 6,221,604, herein incorporated by reference). In this configuration, the set of PNA oligomers for determining a particular SNP were independently detectable self-indicating combination oligomers (See Table 9).

Flu- and Tam-labeled PNA oligomers were synthesized de novo, whereas the Dye1- and Dye2-labeled PNA oligomer probes were each synthesized as two 5mer oligomer blocks that were subsequently condensed/ligated to thereby produce a 10mer PNA combination oligomer probe. For each set of probes, the nucleobase directed to the SNP target was located in the middle of either the N-terminal 5mer or the C-terminal 5mer. The Flu- and Tam-labeled probes were diluted to approximately 400 µM in 50% aqueous DMF, whereas the Dye1- and Dye2-labeled probes were diluted to 50 µM in 50% aqueous NMP. DMF and NMP were purchased from JT Baker (Philipsburg, N.J.) and Applied Biosystems, respectively. The ten PNA probe sets are described in Table 9. In all cases, the probes of a set were independently detectable.

TABLE 9

Combination Oligomer Probe Sets For SNP Analysis. The probe nucleobases directed to the SNP targets are in bold, underlined print.

| SNP | Name | Sequence | Comments |
|---|---|---|---|
| 6784 | 6784-1-A-Flu | Flu-TGACC-Gly-Gly-AGCAA-Lys(Dabcyl)-NH$_2$ |  |
|  | 6784-1-G-Tam | Tam-TGGCC-Gly-Gly-AGCAA-Lys(Dabcyl)-NH$_2$ |  |
| 6802 | 6802-1-A-Flu | Flu-GAGGT-Gly-Gly-CATGG-Lys(Dabcyl)-NH$_2$ |  |
|  | 6802-2-G-Tam | Tam-GAGGT-Gly-Gly-CACGG-Lys(Dabcyl)-NH$_2$ |  |
| 6806 | 6806-1-A-Flu | Flu-TGGTC-Gly-Gly-AAAGA-Lys(Dabcyl)-NH$_2$ |  |
|  | 6806-1-G-Tam | Tam-TGGTC-Gly-Gly-AAGGA-Lys(Dabcyl)-NH$_2$ |  |
| 6834 | 6834-2-A-Flu | Flu-AGGTA-Gly-Gly-AAAGA-Lys(Dabcyl)-NH$_2$ |  |
|  | 6834-2-G-Tam | Tam-AGGTA-Gly-Gly-AAGGA-Lys(Dabcyl)-NH$_2$ |  |
| 6837 | 6837-2-C-Flu | Flu-AGGAC-Gly-Gly-AGGGG-Lys(Dabcyl)-NH$_2$ |  |
|  | 6837-2-T-Tam | Tam-AGAAC-Gly-Gly-AGGGG-Lys(Dabcyl)-NH$_2$ |  |

TABLE 9-continued

Combination Oligomer Probe Sets For SNP Analysis. The probe nucleobases directed to the SNP targets are in bold, underlined print.

| SNP | Name | Sequence | Comments |
|---|---|---|---|
| 6848 | 6848-1-A-Flu | Flu-AGAAT-Gly-Gly-GAGAC-Lys(Dabcyl)-NH$_2$ | |
| | 6848-1-C-Tam | Tam-AGCAT-Gly-Gly-GAGAC-Lys(Dabcyl)-NH$_2$ | |
| 6876 | 6876-1-A-Flu | Flu-CTGGG-Gly-Gly-TTATA-Lys(Dabcyl)-NH$_2$ | |
| | 6876-1-G-Tam | Tam-TTGTA-Gly-Gly-ACCAC-Lys(Dabcyl)-NH$_2$ | |
| 6879 | 6879-1-C-Flu | Flu-GGATA-Gly-Gly-GTCGG-Lys(Dabcyl)-NH$_2$ | |
| | 6879-1-T-Tam | Tam-GTTGG-Gly-Gly-GTGAA-Lys(Dabcyl)-NH$_2$ | |
| 6885 | 6885-1-C-Flu | Flu-GCAAG-Gly-Gly-ACGAG-Lys(Dabcyl)-NH$_2$ | |
| | 6885-1-T-Tam | Tam-GCAAG-Gly-Gly-ACAAG-Lys(Dabcyl)-NH$_2$ | |
| | 6885-1-T-Dye1 | Dye1-GCAAG-Gly-Gly-ACAAG-Lys(Dabcyl)-NH$_2$ | Ligated PNA probe |
| | 6885-1-C-Dye2 | Dye2-GCAAG-Gly-Gly-ACGAG-Lys(Dabcyl)-NH$_2$ | Ligated PNA probe |

PCR protocol. The PCR was performed in triplicate for each sample using an ABI Prism 7700 Sequence Detector (Applied Biosystems). A No Target Control (NTC) (absence of human genomic DNA target) was also performed for each SNP tested. The PCR mixture contained 2 mM MgCl$_2$, 1× Gold Buffer, 0.25 mM dNTP with dTTP, 0.04 U/µL AmpliTaq Gold DNA Polymerase, 200 nM of each primer, 200 nM of each PNA probe, and 0.5 ng/µL human genomic DNA target. Millipore Milli-Q water was used as the PCR mixture diluent. One exception to this formulation included the PCR mixture for SNP 6834, which contained 2000 nM of the primer with the higher Tm value. This would permit the further generation of single stranded DNA amplicons by the PCR. Fifty µL of each sample were then loaded into a MicroAmp Optical 96-Well Reaction Plate and covered with an Optical Adhesive Cover. The MgCl$_2$, Gold Buffer, dNTP with dTTP, AmpliTaq Gold DNA Polymerase, MicroAmp Optical 96-Well Reaction Plates, and Optical Adhesive Covers were purchased from Applied Biosystems. The thermocycling consisted of one round of enzyme activation (95° C., 10 min); 30 rounds of denaturation (95° C., 15 s), annealing (60° C., 30 s), and extension (75° C., 15 s); and 15 rounds of denaturation (95° C., 15 s), annealing (70° C., 30 s), and extension (75° C., 15 s). The lower and higher annealing temperatures favored the generation of double and single stranded DNA amplicons, respectively, because of the unequal primer Tm values. Following the PCR, the single stranded DNA amplicons served as the targets for the PNA probes.

Detection of fluorescence. Following the PCR, the 50 µL samples were transferred to a 96 well, 250 µL, black polystyrene, V bottom Uniplate purchased from Whatman Polyfiltronics (Clifton, N.J.). The fluorescence of the dye-labeled PNA probes in each sample was then measured at room temperature in a Wallac Victor 1420 Multilabel Counter with Flu, Cy3, Dye1, and Dye2 filter sets (Wallac Oy, Turku, Finland). The Cy3 filter set was suitable for measuring Tam fluorescence. The Dye1 filter set consisted of a 460-40 excitation filter and 510-10 emission filter, whereas the Dye2 filter set consisted of a 530-25 excitation filter and 590-20 emission filter (Wallac Oy).

Data analysis. Bar graphs were generated by subtracting the fluorescent signal of the NTC from the fluorescent signal of each sample; the NTC then provided a signal of zero. Allele distribution plots (scatter plots) were generated by dividing the fluorescent signal of the NTC from the fluorescent signal of each sample; the NTC then provided a ratio of one. This ratio was referred to as the signal/noise ratio.

Results

SNP analysis with de novo synthesized, Flu- and Tam-labeled PNA probes. The bar graphs and allele distribution plots for each SNP evaluated are displayed in FIGS. 4-25. A DNA sample that displayed high signal of one dye and negligible signal of the other dye was described as a homozygote. The SNP variant of the homozygote was then determined by the dye that displayed the high signal. For example, the DNA sample M02 of pedigree 1333 was deemed a homozygote for SNP 6802 as high Flu signal and negligible Tam signal were displayed (FIGS. 6 and 7). The SNP site of that target was also deemed to contain the nucleobase adenine as the Flu-labeled PNA probe contained the nucleobase thymine at the SNP site (Table 9). In contrast, the other state of homozygosity was for the target containing the nucleobase guanine since the probe contained the nucleobase cytosine at the SNP site (See Table 9) and would have been determined if the Tamra-labeled probe (6802-2-G-Tam) produced the predominate signal.

DNA sample S03 of pedigree 1333 provided an ambiguous result for SNP 6806 (FIGS. 8 and 9). However, one replicate of the triplicates tested provided low signal (data not shown). If this outlier were removed, the SNP result would have been deemed a homozygote as detected by the Tam-labeled PNA probe and is described as such.

A DNA sample that displayed signals of both dyes of roughly equivalent intensity was described as a heterozygote. For example, the DNA sample F01 of pedigree 1333 was deemed a heterozygote for SNP 6802 as Flu and Tam signals were of roughly equivalent intensities (FIGS. 6 and 7). The SNP sites of those targets were also deemed to contain the nucleobases adenine and guanine as the Flu- and Tam-labeled PNA probes contained the nucleobases thymine and cytosine at the SNP sites, respectively (Table 9).

The SNP results are summarized in Table 10. A homozygotic DNA sample was illustrated by two adjacent plus signs under the same SNP target nucleobase heading, whereas a heterozygotic DNA sample was illustrated by single plus signs under both SNP target nucleobase headings. The results obtained in this study are in full agreement with the data provided by the Whitehead Institute for samples analyzed with the TaqMan Assay of Applied Biosystems, Foster City, Calif. (See: shaded rows of Table 10).

TABLE 10

Chart of SNP results.

| Pedigree | DNA Sample | 6784 A G | 6802 A G | 6806 A G | 6834 A G | 6837 A G | 6848 A C | 6876 A G | 6879 A G | 6885 A G |
|---|---|---|---|---|---|---|---|---|---|---|
| | | | | SNP and Deduced SNP Variants | | | | | | |
| 1331 | F01 | | | | ++ | + + | | | ++ | |
| 1331 | M02 | | | | + + | + + | | | ++ | |
| 1331 | D03 | | | | ++ | | + + | | ++ | |
| 1331 | S04 | | | | + + | | | ++ | ++ | |
| 1331 | D05 | | | | + + | | | ++ | ++ | |
| 1331 | D06 | | | | ++ | | ++ | | ++ | |
| 1331 | D07 | | | | ++ | + + | | | ++ | |
| 1331 | D08 | | | | ++ | + + | | | ++ | |
| 1331 | S09 | | | | ++ | + + | | | ++ | |
| 1331 | S10 | | | | + + | | | ++ | ++ | |
| 1331 | S11 | | | | + + | | | ++ | ++ | |
| 1331 | FF12 | | | | ++ | + + | | | ++ | |
| 1331 | FM13 | | | | + + | ++ | | | ++ | |
| 1331 | MF14 | | | | ++ | ++ | | | ++ | |
| 1331 | MM15 | | | | ++ | | ++ | | ++ | |
| 1331 | D16 | | | | + + | | | ++ | ++ | |
| 1331 | S17 | | | | + + | | | ++ | ++ | |
| 1333 | F01 | ++ | + + | ++ | + + | | | | ++ | + + |
| 1333 | M02 | ++ | ++ | ++ | | | | | + + | ++ |
| 1333 | S03 | ++ | + + | + + | | | | ++ | | + + |
| 1333 | S04 | ++ | + + | | ++ | | | + + | | + + |
| 1333 | S05 | ++ | ++ | + + | | | | + + | | + + |
| 1333 | D06 | ++ | + + | ++ | | | | | ++ | + + |
| 1333 | S07 | ++ | ++ | + + | | | | | ++ | + + |
| 1333 | S08 | ++ | ++ | + + | | | | + + | | + + |
| 1333 | S09 | ++ | ++ | + + | | | | + + | | + + |
| 1333 | S10 | ++ | + + | | ++ | | | ++ | | + + |
| 1333 | FF11 | ++ | + + | ++ | | | | | ++ | + + |
| 1333 | FM12 | ++ | ++ | ++ | | | | | + + | ++ |
| 1333 | MF13 | ++ | + + | | ++ | | | | ++ | + + |
| 1333 | MM14 | ++ | ++ | ++ | | | | | + + | + + |
| 1333 | D15 | ++ | + + | | ++ | | | + + | | + + |
| 1341 | F01 | | | | | ++ | | | ++ | + + |
| 1341 | M02 | | | | | + + | | | ++ | + + |
| 1341 | D03 | | | | | ++ | | + + | | + + |
| 1341 | D04 | | | | | ++ | | + + | | + + |
| 1341 | D05 | | | | | ++ | | + + | | + + |
| 1341 | D06 | | | | | ++ | | + + | | + + |
| 1341 | S07 | | | | | + + | | | ++ | + + |
| 1341 | D08 | | | | | ++ | | + + | | + + |
| 1341 | D09 | | | | | + + | | | ++ | + + |
| 1341 | S10 | | | | | ++ | | + + | | ++ |
| 1341 | FF11 | | | | | + + | | | ++ | ++ |
| 1341 | FM12 | | | | | + + | | | ++ | + + |
| 1341 | MF13 | | | | | ++ | | | ++ | + + |
| 1341 | MM14 | | | | | + + | | | + + | + + |

SNP analysis with ligated, Dye1- and Dye2-labeled PNA probes. The sequences of Dye1- and Dye2-labeled PNA probes for SNP 6885 corresponded to their Tam- and Flu-labeled counterparts, respectively (Table 10). The Coriell Pedigree 1341 chosen for evaluation displayed the anticipated zygosities (FIGS. 26 and 27) and these results were in full agreement with the results generated with the Flu- and Tam-labeled PNA probes (FIGS. 24, 25 and Table 10). Therefore, the fluorophores of Dye1 and Dye2 provided compatibility with the assay and signal upon hybridization to target. Furthermore, the results recorded demonstrate that the condensation/ligation process imposed no adverse consequences upon the function of the probes.

Example 6

Ligation in the Absence of a Template Using Two Labeled Oligomer Blocks

Introduction & Purpose

In Example 2 it was demonstrated that ligation of unlabeled oligomer blocks was possible. This Example was intended to confirm whether or not it was possible to ligate two labeled block oligomers and thereby produce independently detectable, self-indicating combination oligomers.

Reagent Solutions:

0.75M 2-(N-Morpholino)ethane sulfonic acid (MES) Buffer; pH 6.0

35 mM HOBt Solution: Prepared by mixing 23.7 mg of 1-Hydroxybenzotriazole (HOBt) with 4.42 mL of 0.75M MES Buffer pH 6.0.

EDC Solution was prepared by weighing out 1-Ethyl-3-(3-Dimethylamino-propyl)carbodiimide hydrochloride (EDC) then adding a volume of the HOBt Solution prepared above so that the final solution will deliver 0.8 mg EDC per 15 µL of this solution. (EDC Solution is thus 0.278 M)

Quenching Solution was prepared by adding 0.5 ml Trifluoroacetic acid to 49.5 mL de-ionized water.

PNA Solution was prepared by dissolving PNA oligomer blocks in 50% Acetonitrile:50% 0.1% aqueous Trifluoroacetic acid to a concentration of 2625 µM for the dye labeled block and 3000 µM for the Dabcyl-labeled block.

General Reaction Conditions:

Final reaction conditions are generally 10 equivalents of HOBt and ~160 equivalents of EDC in a reaction mixture that was approximately 750 µM in each dye labeled oligomer block to be ligated. It is noted that in these experiments, no template was used (i.e. non-template directed ligation).

Experiment One:

About 5 µL of PNA Solution of each PNA oligomer block (the two oligomer blocks to be ligated) was added to a single 0.5 mL microcentrifuge tube. To the PNA oligomer mixture was added 7.5 µL of the EDC Solution prepared as above. This solution was mixed by vortex and then placed in a heat block maintained at 80° C. After 60 min, 20 µL of the Quenching Solution was added. The product was then analyzed by Maldi-TOF mass spectrometry and HPLC.

Experiment Two:

About 5 µL of PNA Solution of each PNA oligomer block (the oligomer blocks to be ligated) was added to a single 0.5 mL microcentrifuge tube. To the PNA oligomer mixture was added 7.5 µL of the EDC Solution prepared as above. This solution was mixed by vortex and then placed in a heat block maintained at 80° C. After 60 min, 20 µL of the Quenching Solution was added. The product was then analyzed by Maldi-TOF mass spectrometry and HPLC.

Results:

TABLE 11

Table Of Ligation Results

| Experiment # | % Product (1 hour) |
|---|---|
| 1 | 61* |
| 2 | 66* |

*Average of two ligations with different oligomer blocks

For both experiments the amine terminal block (condensing block) was labeled with the dye (Dye1 or Dye2) and the carboxyl terminal block (terminal block) was labeled with dabcyl.

Specifically, the condensing block (PNA) was Dye1-TGG-TC-Gly-COOH and the terminal block was H-Gly-AAA-GA-Lys(Dabcyl)-$NH_2$ for experiment one and Dye2-TGG-TC-Gly with terminal block Gly-AAG-GA-Lys(Dabcyl)-$NH_2$ in experiment two wherein Lys(Dabcyl) represents a Dabcyl moiety attached to the γ amine of the amino acid Lysine, Gly represents that amino acid glycine and other abbreviations are well known in the field of peptide chemistry.

With reference to Table 11, the percent completion of the ligation reaction was measured based on the integration of peak area (excluding the peak representing the HOBt) of the HPLC analysis of the product. The results demonstrated that the two PNA oligomer blocks can, in the absence of a template, be successfully ligated in greater than 50% yield within 1 hour. The results demonstrate that two PNA oligomer blocks, one with a N-terminal glycine comprising a free N-terminal amine group and the other comprising a C-terminal glycine having a carboxylic acid functional group can be ligated rapidly and efficiently with a mixture of HOBt and EDC to thereby produce an unmodified gly-gly dimer that links the two PNA oligomer blocks. The products of the ligation reactions were Dye1-TGG-TC-gly-gly-AAA-GA-Lys(Dabcyl)-$NH_2$ and Dye2-TGG-TC-gly-gly-AAG-GA-Lys(Dabcyl)-$NH_2$. This was confirmed by Maldi-TOF mass spectrometry analysis of the final product. Accordingly, the Example confirms that it is possible to ligate two labeled oligomer blocks to thereby produce independently detectable, self-indicating combination oligomers using a library approach.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the invention.

We claim:

1. An array of at least two oligomers, wherein at least one of the oligomers is a combination oligomer that comprises a segment having the formula:

A-B-C wherein:
each of A and C is an oligomer block independently selected from the group consisting of a peptide nucleic acid, a PNA chimera and a PNA combination oligomer and each of A and C is optionally linked to other moieties; and B is a linker of at least three atoms in length that covalently links oligomer block A to oligomer block C;

wherein:
oligomer blocks A and C taken together encode a probing nucleobase sequence that is designed to sequence specifically hybridize juxtaposed to a target sequence of contiguous nucleobases, such that there is no gap or gap base, to thereby form a double stranded target sequence/combination oligomer complex.

2. The away of clam 1, wherein the linker is not part of a nucleobase containing backbone subunit of the polymer.

3. The array of claim 1, wherein the linker is selected from the group consisting of one amino acid residue, two amino acid residues, three amino acid residues, one E-linker residue, two E-Linker residues, one O-linker residue, two O-linker residues, one X-linker residue and two X-linker residues.

4. The array of claim 3, wherein the linker is selected from the group consisting of the amino acid glycine, the amino acid dimer gly-gly, the amino acid dimer gly-lys, the amino acid dimer lys-gly, the amino acid dimer glu-gly, the amino acid dimer gly-cys, the amino acid dimer cys-gly and the amino acid dimer asp-gly.

5. The array of claim 1, wherein at least one of the at least two oligomers comprises a third oligomer block that is linked covalently to the first or second oligomer block by a second linker that is at least three atoms in length, such that the second linker is the same or different in kind from the first said linker.

6. The array of claim 1, wherein the first and second oligomer blocks are peptide nucleic acids.

7. The array of claim 1, wherein at least one of the at least two oligomers further comprises at least one energy transfer set of labels such that at least one acceptor moiety of the energy transfer set is linked to one of the linked oligomer blocks of the combination oligomer whilst at least one donor moiety of the energy transfer set is linked to another of the linked oligomer blocks of the combination oligomer, wherein the labels of the set are linked to the oligomer blocks at positions that facilitate a change in detectable signal of at least one label when the combination oligomer is hybridized to the target sequence as compared to when the combination oligomer is in a non-hybridized state.

8. The array of claim 7, wherein the labels of the energy transfer set are linked to the distal-most termini of the oligomer blocks or to sites within the oligomer blocks.

9. The array of claim 8, wherein the energy transfer set of each combination oligomer comprises a single donor moiety and a single acceptor moiety.

10. The array of claim 9, wherein both the donor and acceptor moieties are fluorophores.

11. The array of claim 9, wherein the donor moiety is a donor fluorophore and the acceptor moiety is a non-fluorescent quencher moiety.

12. The array of claim 1, wherein each combination oligomer further comprises one or more reporter moieties.

13. The array of claim 1, wherein each combination oligomer is unlabeled.

14. A method comprising:
(a) reacting, at a site on a solid surface, a first oligomer block, a second oligomer block, and optionally a condensation reagent or reagents under condensation conditions to thereby form a combination oligomer having a linker of at least three atoms in length that covalently links the first oligomer block to the second oligomer block;
wherein:
(i) one of said two oligomer blocks is support bound;
(ii) each of the first and second oligomer blocks independently selected from the group consisting of a peptide nucleic acid, a PNA chimera and a PNA combination oligomer;
(iii) one or both oligomer blocks do not comprise nucleobase protecting groups; and
(iv) the combination oligomer forms in the absence of a template; and
(b) repeating step (a) at one or more sites until the array of combination oligomers is constructed,
with the further proviso that the first and second oligomer blocks taken together encode a probing nucleobase sequence that is designed to sequence specifically hybridize juxtaposed to a target sequence of contiguous nucleobases, such that there is no gap or gap base, to thereby form a double stranded target sequence/combination oligomer complex.

15. The method of claim 14, wherein the linker is not part of a nucleobase containing backbone subunit of the polymer.

16. A method comprising:
(a) reacting, at a site on a solid surface, a combination oligomer having a linker of at least three atoms in length that covalently links the first oligomer block to the second oligomer block with a surface functional group to thereby attached the combination oligomer to the surface of the array, wherein:
(i) each of the first and second oligomer blocks independently selected from the group consisting of a peptide nucleic acid, a PNA chimera and a PNA combination oligomer;
(ii) one or both oligomer blocks do not comprise nucleobase protecting groups; and
(b) repeating step (a) at one or more sites until the array of combination oligomers is constructed,
with the further proviso that the combination oligomer hybridizes juxtaposed to a target sequence of contiguous nucleobases, with no gap or gap base.

17. The method of claim 16, wherein the linker is not part of a nucleobase containing backbone subunit of the polymer.

18. An array of at least two oligomers, wherein at least one of the oligomers is a combination oligomer that comprises a segment having the formula:

A-B-C wherein:
each of A and C is an oligomer block independently selected from the group consisting of a peptide nucleic acid, a PNA chimera and a PNA combination oligomer and each of A and C is optionally linked to other moieties; and B is a linker of at least three atoms in length that covalently links oligomer block A to oligomer block C;

wherein:
oligomer blocks A and C taken together encode a probing nucleobase sequence that is designed to sequence specifically hybridize juxtaposed to a target sequence of contiguous nucleobases, such that there is no gap or gap base, to thereby form a double stranded target sequence/ combination oligomer complex, with the further proviso that the linker is not part of a nucleobase containing backbone subunit of the polymer.

19. An array of at least two oligomers, wherein at least one of the oligomers is a combination oligomer that comprises a segment having the formula:

A-B-C wherein:
each of A and C is an oligomer block independently selected from the group consisting of a peptide nucleic acid, a PNA chimera and a PNA combination oligomer and each of A and C is optionally linked to other moieties; and B is a linker of at least three atoms in length that covalently links oligomer block A to oligomer block C;

wherein:
oligomer blocks A and C taken together encode a probing nucleobase sequence that is designed to sequence specifically hybridize juxtaposed to a target sequence of contiguous nucleobases, such that there is no gap or gap base, to thereby form a double stranded target sequence/ combination oligomer complex, and wherein at least one of the at least two oligomers further comprises at least one energy transfer set of labels such that at least one acceptor moiety of the energy transfer set is linked to one of the linked oligomer blocks of the combination oligomer whilst at least one donor moiety of the energy transfer set is linked to another of the linked oligomer blocks of the combination oligomer, wherein the labels of the set are linked to the oligomer blocks at positions that facilitate a change in detectable signal of at least one label when the combination oligomer is hybridized to the target sequence as compared to when the combination oligomer is in a non-hybridized state.

20. The array of claim 19, wherein the labels of the energy transfer set are linked to the distal-most termini of the oligomer blocks or to sites within the oligomer blocks.

21. The array of claim 20, wherein the energy transfer set of each combination oligomer comprises a single donor moiety and a single acceptor moiety.

22. The array of claim 21, wherein both the donor and acceptor moieties are fluorophores.

23. The array of claim 21, wherein the donor moiety is a donor fluorophore and the acceptor moiety is a non-fluorescent quencher moiety.

24. A method comprising:
(a) reacting, at a site on a solid surface, a first oligomer block, a second oligomer block, and optionally a condensation reagent or reagents under condensation conditions to thereby form a combination oligomer having a linker of at least three atoms in length that covalently links the first oligomer block to the second oligomer block, wherein:
(i) one of said two oligomer blocks is support bound;
(ii) each of the first and second oligomer blocks independently selected from the group consisting of a peptide nucleic acid, a PNA chimera and a PNA combination oligomer;
(iii) one or both oligomer blocks do not comprise nucleobase protecting groups; and
(iv) the combination oligomer forms in the absence of a template; and
(b) repeating step (a) at one or more sites until the array of combination oligomers is constructed,
with the further proviso that the linker is not part of a nucleobase containing backbone subunit of the polymer.

25. The method of claim 24, wherein the first and second oligomer blocks taken together encode a probing nucleobase sequence that is designed to sequence specifically hybridize juxtaposed to a target sequence of contiguous nucleobases, such that there is no gap or gap base, to thereby form a double stranded target sequence/combination oligomer complex.

26. A method comprising:
(a) reacting, at a site on a solid surface, a combination oligomer having a linker of at least three atoms in length that covalently links the first oligomer block to the second oligomer block with a surface functional group to thereby attached the combination oligomer to the surface of the array, wherein:
(i) each of the first and second oligomer blocks independently selected from the group consisting of a peptide nucleic acid, a PNA chimera and a PNA combination oligomer;
(ii) one or both oligomer blocks do not comprise nucleobase protecting groups; and
(b) repeating step (a) at one or more sites until the array of combination oligomers is constructed,
with the further proviso that the linker is not part of a nucleobase containing backbone subunit of the polymer.

27. The method of claim 26, wherein the first and second oligomer blocks taken together encode a probing nucleobase sequence that is designed to sequence specifically hybridize juxtaposed to a target sequence of contiguous nucleobases, such that there is no gap or gap base, to thereby form a double stranded target sequence/combination oligomer complex.

* * * * *

SEQUENCE LISTING

<160> NUMBER OF SEQ ID NOS: 25

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 1
tagttggagc tggtggc                                                   17

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Target

<400> SEQUENCE: 2

-continued

```
tagttggact ggtggc                                                    16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Target

<400> SEQUENCE: 3
tagttggact tgtggc                                                    16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Target

<400> SEQUENCE: 4
tagttggact agtggc                                                    16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Target

<400> SEQUENCE: 5
tagttggact cgtggc                                                    16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Target

<400> SEQUENCE: 6
tagttggacg ggtggc                                                    16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Target

<400> SEQUENCE: 7
tagttggagt ggtggc                                                    16

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 8
acaagtctgg agtgagc                                                   17
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 9
gcgtggcaga gatccctgtt gc                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 10
gcctctgcag ggtgctgtct tg                                              22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 11
aaatgttggc tgccaacta                                                  19

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 12
cttggagcat cgagact                                                    17

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 13
gcgtggcctg tttggaggtc aa                                              22

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 14
gaggagtggt gctgat                                                     16

```
<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 15
gcggaggcca tagcagaaga gaaga                                          25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 16
ccaagatctc caagtaaaat aac                                            23

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 17
cgcgccaata aatgtaaatg gcacaaatcc a                                   31

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 18
cctcatccag ataatgttgt                                                20

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 19
gcgcgcaaga aaatgaattt tggcataaaa act                                 33

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 20
ttcctcagca accctg                                                    16
```

```
<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 21
gcatagtgga ccccaagtca ccat                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 22
ggaaattgaa tttaccttttt catt                                             24

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 23
ggcgacattc aagttggaat agttctgaga gta                                    33

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 24
ggccaggacc tgtttgtgac atga                                              24

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide Primer

<400> SEQUENCE: 25
tttgctcaat gtgaaatgtt gt                                                22
```